US011497735B2

(12) United States Patent
Sasikumar et al.

(10) Patent No.: US 11,497,735 B2
(45) Date of Patent: Nov. 15, 2022

(54) CONJOINT THERAPIES FOR IMMUNOMODULATION

(71) Applicants: Aurigene Discovery Technologies Limited, Bangalore (IN); Curis, Inc., Lexington, MA (US)

(72) Inventors: Pottayil Govindan N. Sasikumar, Bangalore (IN); Muralidhara Ramachandra, Bangalore (IN); Raghuveer K. Ramachandra, Bengaluru (IN); Adam S. Lazorchak, Arlington, MA (US); Timothy L. Wyant, Bellingham, MA (US)

(73) Assignees: Aurigene Discovery Technologies Limited, Bangalore (IN); Curis, Inc., Lexington, MA (US)

( * ) Notice: Subject to any disclaimer, the term of this patent is extended or adjusted under 35 U.S.C. 154(b) by 154 days.

(21) Appl. No.: 16/761,964

(22) PCT Filed: Oct. 31, 2018

(86) PCT No.: PCT/IB2018/058533
§ 371 (c)(1),
(2) Date: May 6, 2020

(87) PCT Pub. No.: WO2019/087092
PCT Pub. Date: May 9, 2019

(65) Prior Publication Data
US 2020/0289477 A1    Sep. 17, 2020

(30) Foreign Application Priority Data
Nov. 6, 2017   (IN) .............................. 201741039497

(51) Int. Cl.
*A61K 31/4245* (2006.01)
*A61P 35/00* (2006.01)
*A61K 45/06* (2006.01)

(52) U.S. Cl.
CPC .......... *A61K 31/4245* (2013.01); *A61P 35/00* (2018.01); *A61K 45/06* (2013.01)

(58) Field of Classification Search
CPC ...... A61P 35/00; A61K 31/4245; A61K 45/06
See application file for complete search history.

(56) References Cited

U.S. PATENT DOCUMENTS

| | | | |
|---|---|---|---|
| 3,227,725 A | 1/1966 | Fernand et al. | |
| 5,387,585 A | 2/1995 | Borer et al. | |
| 5,665,718 A | 9/1997 | Godel et al. | |
| 8,735,553 B1 | 5/2014 | Li et al. | |
| 9,771,338 B2 | 9/2017 | Sasikumar et al. | |
| 10,173,989 B2 | 1/2019 | Sasikumar et al. | |
| 10,590,093 B2 | 3/2020 | Sasikumar et al. | |
| 10,781,189 B2 * | 9/2020 | Sasikumar ............. | A61K 38/05 |
| 10,961,205 B2 * | 3/2021 | Sasikumar ............. | A61P 35/00 |
| 11,040,948 B2 | 6/2021 | Yu | |
| 11,136,300 B2 | 10/2021 | Sasikumar et al. | |
| 2005/0272779 A1 | 12/2005 | Edwards et al. | |
| 2007/0197522 A1 | 8/2007 | Edwards et al. | |
| 2007/0225332 A1 | 9/2007 | Gu et al. | |
| 2009/0099227 A1 | 4/2009 | Fyfe et al. | |
| 2011/0275673 A1 | 11/2011 | Xiang et al. | |
| 2013/0022629 A1 | 1/2013 | Sharpe et al. | |
| 2014/0199334 A1 | 7/2014 | Sasikumar et al. | |
| 2014/0235620 A1 | 8/2014 | Caferro et al. | |
| 2015/0073042 A1 | 3/2015 | Sasikumar et al. | |
| 2020/0061030 A1 | 2/2020 | Sasikumar et al. | |
| 2020/0239422 A1 | 7/2020 | Sasikumar et al. | |
| 2020/0247766 A1 | 8/2020 | Yu | |
| 2020/0289477 A1 | 9/2020 | Sasikumar et al. | |
| 2020/0368210 A1 | 11/2020 | Sasikumar et al. | |
| 2021/0380544 A1 | 12/2021 | Yu | |
| 2022/0048875 A1 | 2/2022 | Sasikumar et al. | |

FOREIGN PATENT DOCUMENTS

| | | |
|---|---|---|
| JP | 2016/539662 A | 12/2016 |
| KR | 20160081897 A | 7/2016 |
| WO | WO-2001/014557 A1 | 3/2001 |
| WO | WO-2002/079499 A1 | 10/2002 |
| WO | WO-2002/086083 A2 | 10/2002 |
| WO | WO-2003/042402 A2 | 5/2003 |
| WO | WO-03/070711 A1 | 8/2003 |
| WO | WO-2004/004771 A1 | 1/2004 |
| WO | WO-2004/056875 A1 | 7/2004 |
| WO | WO-2005/056550 A2 | 6/2005 |
| WO | WO-2006/121168 A1 | 11/2006 |
| WO | WO-2006/133216 A2 | 12/2006 |

(Continued)

OTHER PUBLICATIONS

Dempke; European Journal of Cancer 2017, 74, 55-72. http://dx.doi.org/10.1016/j.ejca.2017.01.001 (Year: 2017).*
Reitz; J. Med. Chem. 2021, 64, 19, 14757-14772. https://doi.org/10.1021/acs.jmedchem.1c01336 (Year: 2021).*
Wu; RSC Med. Chem., 2021,12, 1672-1679. https://doi.org/10.1039/D1MD00185J (Year: 2021).*
Anderson et al., "Lag-3, Tim-3, and TIGIT: Co-inhibitory Receptors with Specialized Functions in Immune Regulation," Immunity, 44(5): 989-1004 (2016).
Ardestani et al., "Cell death features induced in Leishmania major by 1,3,4-thiadiazole derivatives," Exp Parasitol, 132(2): 116-122 (2012).

(Continued)

*Primary Examiner* — Daniel R Carcanague
(74) *Attorney, Agent, or Firm* — Foley Hoag LLP; David P. Halstead; Alexander J. Chatterley

(57) ABSTRACT

The present disclosure relates to methods comprising administering compounds that inhibit VISTA and PD-1 (e.g., PD-1, PD-L1, or PD-L2) pathways with a compound that inhibits TIM-3 and PD-1 (e.g., PD-1, PD-L1, or PD-L2) pathways. The disclosure also relates to treatment of disorders by inhibiting an immunosuppressive signal induced by VISTA, TIM-3, PD-1, PD-L1, and/or PD-L2.

31 Claims, 5 Drawing Sheets

(56) References Cited

FOREIGN PATENT DOCUMENTS

| WO | WO-2007/075749 | A2 | 7/2007 | | |
|---|---|---|---|---|---|
| WO | WO-2008/011557 | A2 | 1/2008 | | |
| WO | WO-2008/039431 | A2 | 4/2008 | | |
| WO | WO-2008/156712 | A1 | 12/2008 | | |
| WO | WO-2009/006555 | A2 | 1/2009 | | |
| WO | WO-2009/059162 | A1 | 5/2009 | | |
| WO | WO-2009/105712 | A1 | 8/2009 | | |
| WO | WO-2010/051447 | A1 | 5/2010 | | |
| WO | WO-2010/077634 | A1 | 7/2010 | | |
| WO | WO-2011/066389 | A1 | 6/2011 | | |
| WO | WO-2011/082400 | A2 | 7/2011 | | |
| WO | WO-2011/137587 | A1 | 11/2011 | | |
| WO | WO-2011/161699 | A2 | 12/2011 | | |
| WO | WO-2012/129564 | A2 | 9/2012 | | |
| WO | WO-2012/168944 | A1 | 12/2012 | | |
| WO | WO-2013/132317 | A1 | 9/2013 | | |
| WO | WO-2013/144704 | A1 | 10/2013 | | |
| WO | WO-2014/055897 | A2 | 4/2014 | | |
| WO | WO-2014/059173 | A2 | 4/2014 | | |
| WO | WO-2014/100079 | A1 | 6/2014 | | |
| WO | WO-2014/110298 | A1 | 7/2014 | | |
| WO | WO-2014/141104 | A1 | 9/2014 | | |
| WO | WO-2014/147586 | A1 | 9/2014 | | |
| WO | WO-2015/033299 | A1 | 3/2015 | | |
| WO | WO-2015/033301 | A1 | 3/2015 | | |
| WO | WO-2016073470 | A1 | 5/2016 | | |
| WO | WO-2016/142833 | A1 | 9/2016 | | |
| WO | WO-2016/142852 | A1 | 9/2016 | | |
| WO | WO-2016/142886 | A2 | 9/2016 | | |
| WO | WO-2018/047143 | A1 | 3/2018 | | |
| WO | WO-2018073754 | A1 | * | 4/2018 | ........... A61K 31/422 |
| WO | WO-2019/067678 | A1 | 4/2019 | | |
| WO | WO-2019087087 | A1 | * | 5/2019 | ......... A61K 31/4245 |

OTHER PUBLICATIONS

Borg et al., "1,2,4-Oxadiazole Derivatives of Phenylalnine: Potential Inhibitors of Substance P Endopeptidase," Eur. J. Med. Chem., 28(10):801-810 (1993).
Brittain. "Polymorphism in pharmaceutical solids," edited by H.G Brittain, D.J.W. Grant (chapter 1) p. 1-10 and J.K. Guillory (Chapter 5) p. 183-226 (1999).
Byrn et al., "Pharmaceutical Solids: A Strategic Approach to Regulatory Considerations," Pharmaceutical Research, 12(7):945-954 (1995).
CAS Registry No. 1252104-30-5 (2013).
CAS Registry No. 1356744-17-6 (2012).
CAS Registry No. 146429-76-5 (2013).
CAS Registry No. 1494629-78-5 (2013).
CAS Registry No. 1496514-97-6 (2013).
CAS Registry No. 1496518-51-4 (2013).
CAS Registry No. 1557852-63-7 (2014).
CAS Registry No. 1848907-06-1 (2016).
CAS Registry No. 1848909-97-6 (2016).
CAS Registry No. 1857027-85-0 (2016).
CAS Registry No. 1868314-35-5 (2016).
CAS Registry No. 1868388-36-6 (2016).
CAS Registry No. 1868393-26-3 (2016).
CAS Registry No. 1869758-25-7 (2016).
CAS Registry No. 1870159-31-1 (2016).
CAS Registry No. 1875311-16-2 (2016).
CAS Registry No. 1875758-09-0 (2016).
CAS Registry No. 1878569-90-4 (2016).
CAS Registry No. 876710-85-9 (2006).
Database Registry Chemical Abstracts, STN Accession No. 172410-37-6. (1995).
Database Registry Chemical Abstracts, STN Accession No. 197083-27-5. (1996).
Extended European Search Report for EP Application No. 16761169.8 dated Jul. 2, 2019.
Extended European Search Report for EP Application No. 16761184 dated Jun. 26, 2018.
Extended European Search Report for European Application No. 18162983.3 dated Jun. 27, 2018.
Graham, "Clinical Trials of HIV Vaccines," HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM, pp. 1-20-38.
Guo et al., "Design of oxobenzimidazoles and oxindoles as novel androgen receptor antagonists," Bioorg Med Chem Letts 22(7):2572-2578 (2012).
Harvey, "Immunologic and Clinical Effects of Targeting PD-1 in Lung Cancer," Nature, 96: 214-223 (2014).
International Preliminary Reporton Patentability for International Application No. PCT/IB2018/058526 dated May 14, 2020.
International Search Report and Written Opinion for International Application No. PCT/CN2017/104485 dated Jun. 29, 2018.
International Search Report and Written Opinion for International Application No. PCT/IB2014/064279 dated Dec. 12, 2014.
International Search Report and Written Opinion for International Application No. PCT/IB2016/051266 dated Jul. 8, 2016.
International Search Report and Written Opinion for International Application No. PCT/IB2016/051343 dated Jul. 28, 2016.
International Search Report and Written Opinion for International Application No. PCT/IB2017/056462 dated Jan. 10, 2018.
International Search Report Written Opinion for International Application No. PCT/US2018/053052 dated Jan. 29, 2019.
Jin, "Role of PD-1 in Regulating T-Cell Immunity," Current Topics in Microbiology and Immunology, 350: 17-37 (2010).
Lazorchak et al., "Abstract A36: CA-170, an oral small molecule PD-L1 and VISTA immune checkpoint antagonist, promotes T cell immune activation and inhibits tumor growth in pre-clinical models of cancer," Cancer Immunology Research, 5(S3):A36 (2017).
Luo et al., "Principles of Cancer Therapy: Oncogene and Non-oncogene Addiction," Cell, 136(5): 823-837 (2009).
Marechal et al., "1,2,4-oxadiazoles identified by virtual screening and their non-covalent inhibition of the human 20S proteasome," Curr Med Chem 20(18):2351-2362 (2013).
Moussebois et al., "Synthese de Deux Nouveaux Acides Amines Phenoliques Comportant un Cycle 1,2,4-Oxadiazole," Helv. Chim. ACTA, 60(1):237-242 (1977).
Ozcan et al., "Oxadiazole-Isopropylamieds as Potent and Noncovalent Proteasome Inhibitors," J. Med. Chem., 56(10):3783-3805 (2013).
Palazzo et al., "1,2,4-Oxadiazoles—IV. Synthesis and Pharmacological Properties of a Series of Substituted Aminoalkyl—1,2,4-Oxadiazoles," J. Med. Chem., 351-367 (1961).
Patwardhan et al., "Structure-Activity Relationship Studies and in Vivo Activity of Guanidine-Based Sphingosine Kinase Inhibitors: Discovery of SphK1- and SphK2—Selective Inhibitors," J. Med. Chem., 58(4):1879-1899 (2015).
Pedoeem et al., "Programmed Death-1 Pathway in Cancer and Autoimmunity," Clinical Immunology, 153: 145-152 (2014).
Shi et al., "The Role of PD-1 and PD-L1 in T-cell Immune Suppression in Patients with Hematological Malignancies," Journal of Hematology & Oncology, 6(74): 1-6 (2013).
Sureshbabu et al., "Synthesis of 1,2,4-oxadiazole-linked Orthogonally Urethane-Protected Dipeptide Mimetics," Tetrahedron Letters, 49(35): 5133-5136 (2008).
Waldmann, "Effective Cancer Therapy Through Immunomodulation," T Annu Rev Med, 57: 65-81 (2006).
Censi et al., "Polymorph Impact on the Bioavailability and Stability of Poorly Soluble Drugs," Molecules, 20(10): 18759-18776 (2015).
Extended European Search Report for EP Application No. 17862427.6 dated Jun. 5, 2020.
Extended European Search Report for EP Application No. EP/US18/18863750 dated May 31, 2021.
Lee, "A practical guide to pharmaceutical polymorph screening & selection," Asian J Pharm Sci, 9(4): 163-175 (2014).
Liu et al., "Immune-checkpoint proteins VISTA and PD-1 nonredundantly regulate murine T-cell responses," PNAS, 112(21): 6682-6687 (2015).

(56) References Cited

OTHER PUBLICATIONS

Newman, "Specialized Solid Form Screening Techniques," Org Process Res Dev, 13(3): 457-471 (2012).
Sasikumar et al., "PD-1 derived CA-170 is an oral immune checkpoint inhibitor that exhibits preclinical anti-tumor efficacy," Communications Biology, 4: 12 pages (2021).

* cited by examiner

CONJOINT THERAPIES FOR IMMUNOMODULATION

RELATED APPLICATIONS

This application is the § 371 National Stage of PCT/IB2018/058533, filed Oct. 31, 2018, which claims the benefit of Indian provisional application number 201741039497, filed on Nov. 6, 2017; the contents of each of which are hereby incorporated by reference in their entirety.

STATEMENT OF JOINT RESEARCH AGREEMENT

The inventions disclosed herein were made as a result of activities undertaken within the scope of a joint research agreement between Aurigene Discovery Technologies Ltd. and Curis, Inc., which agreement was in effect on or before the effective filing date of the claimed invention.

BACKGROUND

The immune system in mammals sustains the ability to control the homeostasis between the activation and inactivation of lymphocytes through various regulatory mechanisms during and after an immune response. Among these mechanisms, there are mechanisms that specifically modulate the immune response as and when required.

PD-1 (or Programmed Cell Death 1 or PDCD1) is a ~55 kDa type I membrane glycoprotein and is a receptor of the CD28 superfamily proteins programmed death ligand 1 (PD-L1/B7-H1) and programmed death ligand 2 (PD-L2/B7-DC). These interactions negatively regulate T cell antigen receptor signaling and are suggested to play significant role in the maintenance of self-tolerance. The PD-1 protein's structure comprises an extracellular IgV domain followed by a trans-membrane region and an intracellular tail. The intracellular tail contains two phosphorylation sites located in an immunoreceptor tyrosine-based inhibitory motif (ITIM) and an immunoreceptor tyrosine-based switch motif (ITSM), which suggests that PD-1 negatively regulates TCR signals. Also, PD-1 is expressed on the surface of activated T cells, B cells, and macrophages, (Y. Agata et al., Int. Immunol. 1996, 8: 765) suggesting that compared to CTLA-4 [(Cytotoxic T-Lymphocyte Antigen 4), also known as CD152 (Cluster of differentiation 152), a protein that also plays an important regulatory role in the immune system], PD-1 more broadly negatively regulates immune responses.

Blockade of PD-1, an inhibitory receptor expressed by T cells, can overcome immune resistance. PD-1 is a key immune check point receptor expressed by activated T cells, and it mediates immune suppression. PD-1 functions primarily in peripheral tissues, where T cells may encounter the immune suppressive PD-1 ligands; PD-L1 and PD-L2, which are expressed by tumor cells, stromal cells or both. Inhibition of the interaction between PD-land PD-L1 can enhance T-cell responses in vitro and mediate preclinical antitumor activity (S. L. Topalian et al., N. Engl. J. Med. 2012, 366(26): 2443-2454).

However, some patients, over time, become unresponsive to therapies that solely target PD-1, PD-L1 or PD-L2. Strategies for providing more effective and more durable therapies are needed.

SUMMARY OF THE INVENTION

The present invention provides methods of modulating an immune response in a subject by contacting the subject with an inhibitor of the VISTA pathway and an inhibitor of the TIM-3 pathway. The present invention also provides methods of modulating an immune response in a cell by contacting the cell with an inhibitor of the VISTA pathway and an inhibitor of the TIM-3 pathway. V-domain immunoglobulin suppressor of T-cell activation (VISTA) and T-cell immunoglobulin and mucin-domain containing-3 (TIM-3) are immune checkpoints that respectively suppress T-cell activation, and limit T-cell function and survival. It has been demonstrated that these immune checkpoints also play a role in tumor growth and represent attractive therapeutic targets (S. L. Topalian. et al., Cancer Cell, 2015, 27, 450-461; M. J. Smyth et al. Nat. Rev. Clin. Oncol. 2016, 13, 143-158).

In certain embodiments, the methods comprise administering a compound that inhibits the VISTA and PD-1 (e.g., PD-1, PD-L1 or PD-L2) pathways with a compound that inhibits the TIM-3 and PD-1 (e.g., PD-1, PD-L1 or PD-L2) pathways. The present invention also provides compositions, such as pharmaceutical compositions, that comprise an inhibitor of the VISTA pathway and an inhibitor of the TIM-3 pathway, such as a compound that inhibits the VISTA and PD-1 (e.g., PD-1, PD-L1 or PD-L2) pathways and a compound that inhibits the TIM-3 and PD-1 (e.g., PD-1, PD-L1 or PD-L2) pathways.

Representative compounds that inhibit the VISTA pathway include compounds having a structure of formula (I) or a pharmaceutically acceptable salt thereof:

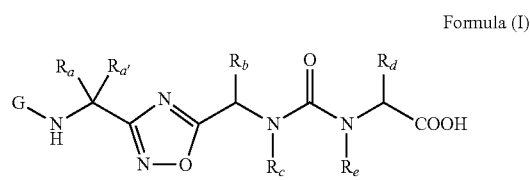

Formula (I)

wherein:
G represents hydrogen or $(C_1-C_6)$alkyl;
$R_a$ represents $(C_1-C_6)$alkyl substituted with —OH, —C(O)NR$_x$R$_y$, —NR$_x$R$_y$, guanidino, carboxylic acid, heteroaryl or aryl-OH;
$R_{a'}$ represents hydrogen; or $R_a$ and $R_{a'}$ taken together with the atom to which they are attached form a 5- to 6-membered ring;
$R_b$ represents $(C_1-C_6)$alkyl, optionally substituted with —OH, —C(O)NR$_x$R$_y$, —NR$_x$R$_y$, carboxylic acid, —C(NH$_2$)C(O)OH or heteroaryl; wherein the heteroaryl is optionally further substituted with hydroxyl;
$R_c$ represents hydrogen; or $R_b$ and $R_c$ taken together with the atoms to which they are attached form a 5- to 6-membered ring;
$R_d$ represents H, $(C_1-C_6)$alkyl substituted with —OH, —NR$_x$R$_y$, or carboxylic acid;
$R_e$ represents hydrogen; or $R_d$ and $R_e$ taken together with the atoms to which they are attached form a 5- to 6-membered ring optionally containing 1 to 3 heteroatoms selected from O, NH or S; and
$R_x$ and $R_y$ independently represent hydrogen, $(C_1-C_6)$alkyl, $(C_2-C_6)$acyl or $(C_1-C_6)$cycloalkyl; or
$R_x$ and $R_y$ taken together with the atom to which they are attached form a 5- to 6-membered ring.

Representative compounds that inhibit the VISTA and PD-1 (e.g., PD-1, PD-L1 or PD-L2) pathways include compounds having a structure of formula (I) or a pharmaceutically acceptable salt thereof:

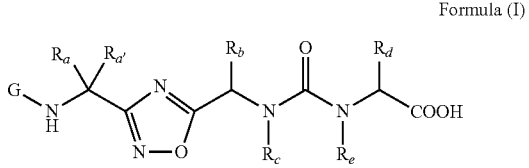

Formula (I)

wherein:

G represents hydrogen or $(C_1-C_6)$alkyl;

$R_a$ represents $(C_1-C_6)$alkyl substituted with —OH, —C(O)NR$_x$R$_y$, —NR$_x$R$_y$, guanidino, carboxylic acid, heteroaryl or aryl-OH;

$R_{a'}$ represents hydrogen; or $R_a$ and $R_{a'}$ taken together with the atom to which they are attached form a 5- to 6-membered ring;

$R_b$ represents $(C_1-C_6)$alkyl, optionally substituted with —OH, —C(O)NR$_x$R$_y$, —NR$_x$R$_y$, carboxylic acid, —C(NH$_2$)C(O)OH or heteroaryl; wherein the heteroaryl is optionally further substituted with hydroxyl;

$R_c$ represents hydrogen; or $R_b$ and $R_c$ taken together with the atoms to which they are attached form a 5- to 6-membered ring;

$R_d$ represents H, $(C_1-C_6)$alkyl substituted with —OH, —NR$_x$R$_y$ or carboxylic acid;

$R_e$ represents hydrogen; or $R_d$ and $R_e$ taken together with the atoms to which they are attached form a 5- to 6-membered ring optionally containing 1 to 3 heteroatoms selected from O, NH or S; and $R_x$ and $R_y$ independently represent hydrogen, $(C_1-C_6)$alkyl, $(C_2-C_6)$acyl or $(C_1-C_6)$cycloalkyl; or $R_x$ and $R_y$ taken together with the atom to which they are attached form a 5- to 6-membered ring.

Representative compounds that inhibit the TIM-3 pathway include compounds having a structure of formula (II) or a pharmaceutically acceptable salt thereof:

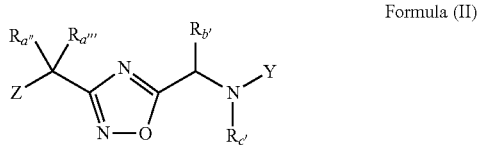

Formula (II)

wherein:

Z represents —OH or —NH-G';

G' represents hydrogen or $(C_1-C_6)$alkyl;

Y represents hydrogen or a group represented by the following structural formula

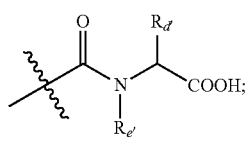

$R_{a''}$ represents $(C_1-C_6)$alkyl substituted with —OH, —NR$_x$R$_y$, —SR$_x$, carboxylic acid, guanidino or aryl, wherein the aryl group is optionally further substituted with hydroxyl; or $R_a$ and G taken together with the atom to which they are attached form a 5- to 6-membered ring containing 1 to 3 heteroatoms selected from O, N or S;

$R_{a'''}$ represents hydrogen; or $R_{a''}$ and $R_{a'''}$ taken together with the atom to which they are attached form a 5- to 6-membered ring, optionally containing 1 to 3 heteroatoms selected from O, N or S;

$R_{b'}$ represents $(C_1-C_6)$alkyl, optionally substituted with —C(O)NR$_x$R$_y$, —NR$_x$R$_y$ or carboxylic acid;

$R_{c'}$ represents hydrogen; or $R_{b'}$ and $R_{c'}$ taken together with the atoms to which they are attached form a 5- to 6-membered ring containing 1 to 3 heteroatoms selected from O, N or S, wherein the 5- to 6-membered ring is optionally further substituted with hydroxyl;

$R_{d'}$ represents $(C_1-C_6)$alkyl, optionally substituted with —OR$_x$, carboxylic acid or aryl-OH;

$R_{e'}$ represents hydrogen; or $R_{d'}$ and $R_{e'}$ taken together with the atoms to which they are attached form a 5- to 6-membered ring containing 1 to 3 heteroatoms selected from O, N or S; and $R_{x'}$ and $R_{y'}$ independently represent hydrogen, $(C_1-C_6)$alkyl or $(C_2-C_6)$acyl.

Accordingly, the present disclosure provides pharmaceutical composition comprising a compound of Formula (I) or a pharmaceutically acceptable salt thereof; and a compound of Formula (II) or a pharmaceutically acceptable salt thereof; and processes for preparing such compositions.

DETAILED DESCRIPTION OF THE INVENTION

Figure 1A:
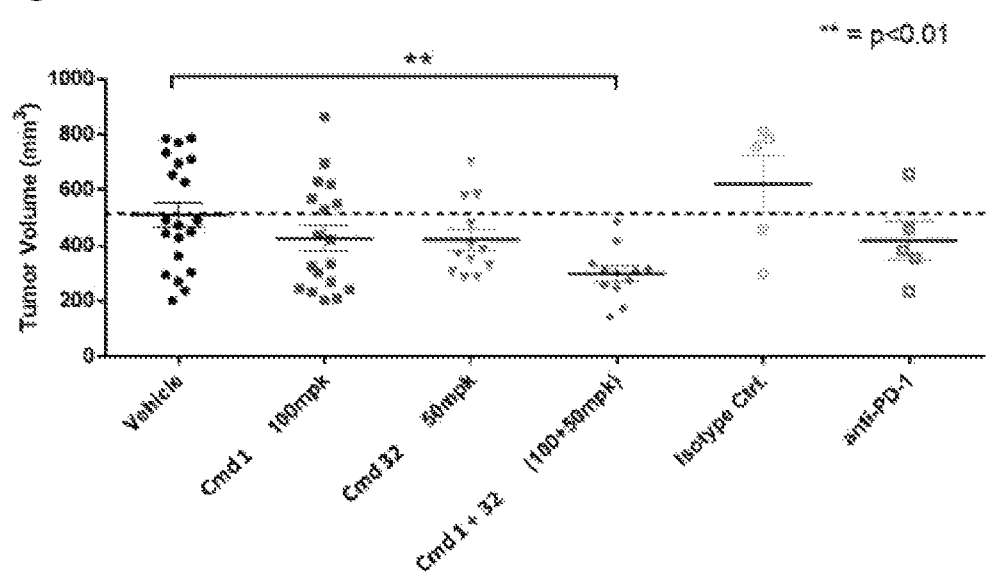
FIG. 1A. Tumor volume (mm$^3$) at day 20 following treatments with Cmd 1 (100 mg/kg), Cmd 32 (50 mg/kg), conjoint administration of Cmd 1 and Cmd 32 (100 and 50 mg/kg respectively), and an anti-PD-1 antibody.

The present invention provides methods of modulating an immune response in a subject by contacting the subject with an inhibitor of the VISTA pathway and an inhibitor of the TIM-3 pathway. The present invention provides methods of modulating a response in an immune cell by contacting the cell with an inhibitor of the VISTA pathway and an inhibitor of the TIM-3 pathway. In certain embodiments, the methods comprise administering a compound that inhibits the VISTA and PD-1 (e.g., PD-1, PD-L1 or PD-L2) pathways with a compound that inhibits the TIM-3 and PD-1 (e.g., PD-1, PD-L1 or PD-L2) pathways. The present invention also provides compositions, such as pharmaceutical compositions, that comprise an inhibitor of the VISTA pathway and an inhibitor of the TIM-3 pathway, such as a compound that inhibits the VISTA and PD-1 (e.g., PD-1, PD-L1 or PD-L2) pathways and a compound that inhibits the TIM-3 and PD-1 (e.g., PD-1, PD-L1 or PD-L2) pathways.

Each embodiment is provided by way of explanation of the disclosure, and not by way of limitation of the disclosure. In fact, it will be apparent to those skilled in the art that various modification and variations can be made in the present disclosure without departing from the scope or spirit of the disclosure. For instance, features illustrated or described as part of one embodiment can be used on another embodiment to yield a still further embodiment. Thus it is intended that the present disclosure cover such modifications and variations as come within the scope of the appended claims and their equivalents. Other objects, features, and aspects of the present disclosure are disclosed in or can be derived from, the following detailed description. It is to be understood by one of ordinary skill in the art that the present discussion is a description of exemplary embodiments only, and is not to be construed as limiting the broader aspects of the present disclosure.

VISTA functions as an immune checkpoint protein that suppresses T-cell activation. VISTA is primarily expressed on hematopoietic cells.

Both the VISTA and programmed cell death protein 1 (PD-1) proteins function as immune checkpoint proteins that suppress T-cell activation. VISTA and the PD-1/PD-L1 pathway nonredundantly regulate T-cell responses. VISTA and the PD-1 pathway have been implicated in a number of diseases and conditions, and VISTA and the PD-1 pathway are known to regulate various immune responses. Numerous studies have sought to activate immune response by targeting VISTA or the PD-1 pathway, thereby providing a therapy for certain conditions, such as cancers and autoimmune disorders. For example, combinatorial treatment using VISTA- and PD-L1-specific monoclonal antibodies achieved synergistic therapeutic efficacy in a colon cancer model showing tumor regression and improved survival (J. Liu et al. Proc. Natl. Acad. Sci. USA 2015, 112(21): 6682-6687). PD-1 activity has also been associated with autoimmune conditions, such as lupus erythematosus, juvenile idiopathic arthritis, and allergic encephalomyelitis.

TIM-3 functions as an immune checkpoint receptor that limits T-cell survival and function and TIM-3 is expressed on certain T cells. Programmed cell death protein 1 (PD-1) functions as an immune checkpoint protein that suppresses T-cell activation. TIM-3 and the PD-1/PD-L1 pathway likely nonredundantly regulate T-cell responses. TIM-3 and the PD-1 pathway have been implicated in a number of diseases and conditions, and TIM-3 and the PD-1 pathway are known to regulate various immune responses. Numerous studies have sought to activate immune response by targeting TIM-3 or the PD-1 pathway, thereby providing a therapy for certain conditions, such as cancers and autoimmune disorders. For example, combinatorial treatment using TIM-3-Fc fusion protein or gal-9 knock out mice combined with PD-L1-specific monoclonal antibodies achieved synergistic therapeutic efficacy in an acute myelogenous leukemia model showing tumor regression and improved survival (Q. Zhou et al., Blood, 2011, 117: 4501-4510). PD-1 activity has also been associated with autoimmune conditions, such as lupus erythematosus, juvenile idiopathic arthritis, and allergic encephalomyelitis. In addition, blockade of the PD-1 pathway and inhibition of TIM-3 restores function to dysfunctional CD8+ T cells (e.g., restoring tumor antigen-specific IFN-γ production) and deprograms potent intratumoral Tregs (e.g., drives the downmodulation of several genes associated with potent Treg-suppressor function) (A. C. Anderson, Cancer Immunol. Res., 2014, 2(5): 393-398). As demonstrated herein, simultaneously inhibiting the TIM-3, VISTA, and PD-1 (e.g., PD-1, PD-L1 or PD-L2) pathways has beneficial effects, even beyond the beneficial effects of inhibiting TIM-3 and PD-1 (e.g., PD-1, PD-L1 or PD-L2) alone or inhibiting VISTA and PD-1 (e.g., PD-1, PD-L1 or PD-L2) alone.

Representative inhibitors of VISTA and PD-1 (e.g., PD-1, PD-L1 or PD-L2) pathways include compounds having a structure of formula (I) or a pharmaceutically acceptable salt thereof:

Formula (I)

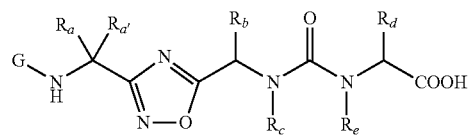

wherein:

G represents hydrogen or $(C_1-C_6)$alkyl;

$R_a$ represents $(C_1-C_6)$alkyl substituted with —OH, —C(O)NR$_x$R$_y$, —NR$_x$R$_y$, guanidino, carboxylic acid, heteroaryl or aryl-OH;

$R_{a'}$ represents hydrogen; or $R_a$ and $R_{a'}$ taken together with the atom to which they are attached form a 5- to 6-membered ring;

$R_b$ represents $(C_1-C_6)$alkyl, optionally substituted with —OH, —C(O)NR$_x$R$_y$, —NR$_x$R$_y$, carboxylic acid, —C(NH$_2$)C(O)OH or heteroaryl; wherein the heteroaryl is optionally further substituted with hydroxyl;

$R_c$ represents hydrogen; or $R_b$ and $R_c$ taken together with the atoms to which they are attached form a 5- to 6-membered ring;

$R_d$ represents H, $(C_1-C_6)$alkyl substituted with —OH, —NR$_x$R$_y$, or carboxylic acid;

$R_e$ represents hydrogen; or $R_d$ and $R_e$ taken together with the atoms to which they are attached form a 5- to 6-membered ring optionally containing 1 to 3 heteroatoms selected from O, NH or S; and $R_x$ and $R_y$ independently represent hydrogen($C_1-C_6$)alkyl, $(C_2-C_6)$acyl or $(C_1-C_6)$cycloalkyl; or $R_x$ and $R_y$ taken together with the atom to which they are attached form a 5- to 6-membered ring.

In certain embodiments of Formula (I), G represents hydrogen or methyl. In some embodiments, G represents hydrogen.

In certain embodiments, $R_a$ represents —(CH$_2$)$_2$C(O)OH or $(C_1-C_4)$alkyl, wherein $(C_1-C_4)$alkyl is substituted with —OH, —C(O)NR$_x$R$_y$, —NR$_x$R$_y$, guanidino, heteroaryl or aryl-OH. In certain embodiments of Formula (I), $R_a$ represents $(C_1-C_4)$alkyl substituted with —OH, —NH$_2$, —C(O)NH$_2$, —NH—C(=NH)—NH$_2$, carboxylic acid, imidazolyl or p-OH(phenyl); and $R_{a'}$ is hydrogen. In some embodiments of Formula (I), $R_a$ represents $(C_1-C_4)$alkyl substituted with —OH, —NH$_2$, —C(O)NH$_2$, —NH—C(=NH)—NH$_2$, imidazolyl or p-OH(phenyl); and $R_{a'}$ is hydrogen. In some embodiments, $R_a$ represents —CH$_2$OH, —CH(CH$_3$)OH, —CH$_2$-(p-OH(phenyl)), —(CH$_2$)$_4$—NH$_2$, —CH$_2$(imidazolyl) or —(CH$_2$)$_3$—NH—C(=NH)—NH$_2$. In some embodiments, $R_a$ represents —CH$_2$OH, —CH(CH$_3$)OH, —CH$_2$-(p-OH(phenyl)), —(CH$_2$)$_4$—NH$_2$, —(CH$_2$)$_2$C(O)OH, —(CH$_2$)$_2$C(O)NH$_2$, —CH$_2$(imidazolyl) or —(CH$_2$)$_3$—

NH—C(=NH)—NH$_2$. In certain embodiments, R$_a$ represents —CH$_2$OH or —CH(CH$_3$)OH. In some embodiments, R$_a$ represents —CH$_2$OH.

Alternatively, in certain embodiments, R$_a$ and R$_{a'}$ taken together with the atoms to which they are attached form a cyclopentyl ring or cyclohexyl ring.

In certain embodiments, R$_b$ represents —CH$_2$C(O)OH or (C$_1$-C$_6$)alkyl, wherein (C$_1$-C$_6$)alkyl is optionally substituted with —OH, —C(O)NR$_x$R$_y$, or heteroaryl, wherein the heteroaryl is optionally further substituted with hydroxyl. In certain embodiments, R$_b$ represents (C$_1$-C$_4$)alkyl, optionally substituted with —OH, —C(O)NH$_2$, carboxylic acid, indolyl, —NH—((C$_2$-C$_6$)acyl) or —C(O)NH—((C$_1$-C$_6$)alkyl); and R$_c$ represents hydrogen. In some embodiments, R$_b$ represents (C$_1$-C$_4$)alkyl, optionally substituted with —OH, —C(O)NH$_2$, indolyl, —NH—(COCH$_3$) or —C(O)NH—((C$_1$-C$_6$)alkyl); and R$_c$ represents hydrogen. In some embodiments, R$_b$ represents isopropyl, sec-butyl, —CH$_2$OH, —CH$_2$C(O)NH$_2$, —(CH$_2$)$_2$C(O)NH$_2$, —(CH$_2$)$_4$—NH(COCH$_3$), —CH$_2$C(O)OH, —(CH$_2$)$_2$C(O)OH, —CH$_2$(indolyl), —CH$_2$C(O)NH(hexyl) or —(CH$_2$)$_2$C(O)NH(hexyl). In some embodiments, R$_b$ represents isopropyl, sec-butyl, —CH$_2$OH, —CH$_2$C(O)NH$_2$, —(CH$_2$)$_2$C(O)NH$_2$, —(CH$_2$)$_4$—NH(COCH$_3$), —CH$_2$C(O)OH, —CH$_2$(indolyl), —CH$_2$C(O)NH(hexyl) or —(CH$_2$)$_2$C(O)NH(hexyl). In certain embodiments, R$_b$ represents —CH$_2$C(O)NH$_2$ or —CH$_2$C(O)OH. In some embodiments, R$_b$ represents —CH$_2$C(O)NH$_2$.

Alternatively, in certain embodiments, R$_b$ and R$_c$ taken together with the atoms to which they are attached form a pyrrolidine ring.

In certain embodiments, R$_d$ represents (C$_1$-C$_4$)alkyl substituted with —OH, —NH$_2$ or —C(O)OH; and R$_e$ represents hydrogen. In some embodiments, R$_d$ represents —CH$_2$OH, —CH(CH$_3$)OH, —(CH$_2$)$_4$—NH$_2$ or —(CH$_2$)$_2$C(O)OH. In some embodiments, R$_d$ represents —CH$_2$OH or —CH(CH$_3$)OH. In certain embodiments, R$_d$ represents —CH(CH$_3$)OH.

Alternatively, in certain embodiments, R$_d$ and R$_e$ taken together with the atoms to which they are attached form a pyrrolidine ring.

In some embodiments of Formula (I),
G represents hydrogen or (C$_1$-C$_6$)alkyl;
R$_a$ represents —(CH$_2$)$_2$C(O)OH or (C$_1$-C$_4$)alkyl, wherein (C$_1$-C$_4$)alkyl is substituted with —OH, —C(O)NR$_x$R$_y$, —NR$_x$R$_y$, guanidino, heteroaryl or aryl-OH;
R$_{a'}$ represents hydrogen; or R$_a$ and R$_{a'}$ taken together with the atom to which they are attached form a 5- to 6-membered ring;
R$_b$ represents —CH$_2$C(O)OH or —(C$_1$-C$_6$)alkyl, wherein (C$_1$-C$_6$)alkyl is optionally substituted with —OH, —C(O)NR$_x$R$_y$, —NR$_x$R$_y$, or heteroaryl; wherein the heteroaryl is optionally further substituted with hydroxyl;
R$_c$ represents hydrogen; or R$_b$ and R$_c$ taken together with the atoms to which they are attached form a 5- to 6-membered ring;
R$_d$ represents H, —(C$_1$-C$_6$)alkyl substituted with —OH, —NR$_x$R$_y$ or carboxylic acid;
R$_e$ represents hydrogen; or R$_d$ and R$_e$ taken together with the atoms to which they are attached form a 5- to 6-membered ring optionally containing 1 to 3 heteroatoms selected from O, NH or S; and
R$_x$ and R$_y$ independently represent hydrogen, (C$_1$-C$_6$)alkyl or (C$_2$-C$_6$)acyl.

In certain embodiments of Formula (I),
G represents hydrogen or methyl;
R$_a$ represents —CH$_2$OH, —CH(CH$_3$)OH, —CH$_2$-(p-OH(phenyl)), —(CH$_2$)$_4$—NH$_2$, —CH$_2$(imidazolyl) or —(CH$_2$)$_3$—NH—C(=N)—NH$_2$;
R$_{a'}$ represents hydrogen; or R$_a$ and R$_{a'}$ taken together with the atoms to which they are attached form cyclohexyl ring;
R$_b$ represents isopropyl, sec-butyl, —CH$_2$OH, —CH$_2$C(O)NH$_2$, —(CH$_2$)$_2$C(O)NH$_2$, —(CH$_2$)$_4$—NH(COCH$_3$), —CH$_2$C(O)OH, —(CH$_2$)$_2$C(O)OH, —CH$_2$(indolyl), —CH$_2$C(O)NH(hexyl) or —(CH$_2$)$_2$C(O)NH(hexyl);
R$_c$ represents hydrogen; or R$_b$ and R$_c$ taken together with the atoms to which they are attached to form a pyrrolidine ring;
R$_d$ represents H, —CH$_2$OH, —CH(CH$_3$)OH, —(CH$_2$)$_4$—NH$_2$ or —(CH$_2$)$_2$C(O)OH; and
R$_e$ represents hydrogen; or R$_d$ and R$_e$ taken together with the atoms to which they are attached to form a pyrrolidine ring.

In certain embodiments of Formula (I),
G represents hydrogen or methyl;
R$_a$ represents —CH$_2$OH, —CH(CH$_3$)OH, —CH$_2$-(p-OH(phenyl)), —(CH$_2$)$_2$C(O)NH$_2$, —(CH$_2$)$_4$—NH$_2$, —(CH$_2$)$_2$COOH, —CH$_2$(imidazolyl) or —(CH$_2$)$_3$—NH—C(=N)—NH$_2$;
R$_{a'}$ represents hydrogen; or R$_a$ and R$_{a'}$ taken together with the atoms to which they are attached form cyclopentyl ring or cyclohexyl ring;
R$_b$ represents isopropyl, sec-butyl, —CH$_2$OH, —CH$_2$C(O)NH$_2$, —(CH$_2$)$_2$C(O)NH$_2$, —(CH$_2$)$_4$—NH(COCH$_3$), —CH$_2$C(O)OH, —CH$_2$(indolyl), —CH$_2$C(O)NH(hexyl) or —(CH$_2$)$_2$C(O)NH(hexyl);
R$_c$ represents hydrogen; or R$_b$ and R$_c$ taken together with the atoms to which they are attached to form a pyrrolidine ring;
R$_d$ represents —CH$_2$OH, —CH(CH$_3$)OH, —(CH$_2$)$_4$—NH$_2$, —CH$_2$COOH or —(CH$_2$)$_2$C(O)OH; and
R$_e$ represents hydrogen; or R$_d$ and R$_e$ taken together with the atoms to which they are attached to form a pyrrolidine ring.

In certain embodiments of Formula (I),
G represents hydrogen or methyl;
R$_a$ represents —CH$_2$OH, —CH(CH$_3$)OH, —CH$_2$-(p-OH(phenyl)), —(CH$_2$)$_4$—NH$_2$, —(CH$_2$)$_2$COOH, —CH$_2$(imidazolyl) or —(CH$_2$)$_3$—N(=NH)—NH$_2$;
R$_{a'}$ represents hydrogen; or R$_a$ and R$_{a'}$ taken together with the atoms to which they are attached form cyclohexyl ring;
R$_b$ represents isopropyl, sec-butyl, —CH$_2$OH, —CH$_2$C(O)NH$_2$, —(CH$_2$)$_2$C(O)NH$_2$, —CH$_2$C(O)OH, —(CH$_2$)$_4$—NH(COCH$_3$), —CH$_2$(indolyl), —CH$_2$C(O)NH(hexyl) or —(CH$_2$)$_2$C(O)NH(hexyl);
R$_c$ represents hydrogen; or R$_b$ and R$_c$ taken together with the atoms to which they are attached to form a pyrrolidine ring;
R$_d$ represents —CH$_2$OH, —CH(CH$_3$)OH, —(CH$_2$)$_4$—NH$_2$ or —(CH$_2$)$_2$C(O)OH; and
R$_e$ represents hydrogen; or R$_d$ and R$_e$ taken together with the atoms to which they are attached to form a pyrrolidine ring.

In certain embodiments, R$_a$ represents —CH$_2$OH or —CH(CH$_3$)OH, R$_b$ represents —CH$_2$C(O)NH$_2$ or —CH$_2$C(O)OH, and R$_d$ represents —CH$_2$OH or —CH(CH$_3$)OH. In some embodiments, R$_a$ represents —CH$_2$OH or —CH(CH$_3$)OH, R$_b$ represents —CH$_2$C(O)NH$_2$, and R$_d$ represents —CH(CH$_3$)OH. In some embodiments, R$_a$ represents —CH$_2$OH, R$_b$ represents —CH$_2$C(O)NH$_2$, and R$_d$ represents —CH(CH$_3$)OH. In some embodiments, R$_a$ represents —CH(CH$_3$)OH, R$_b$ represents —CH$_2$C(O)NH$_2$, and R$_d$ represents —CH$_2$OH.

In certain embodiments, the compound of formula (I) or a pharmaceutically acceptable salt thereof, is selected from:

TABLE 1

Exemplary Compounds of the Present Invention

| Cmd No. | G | $R_a$ | $R_{a'}$ | $R_b$ | $R_c$ | $R_d$ | $R_e$ |
|---|---|---|---|---|---|---|---|
| 1 | H | —CH$_2$OH<br>Ser S | H | —CH$_2$C(O)NH$_2$<br>Asn N | H | —CH(CH$_3$)OH<br>Thr T | H |
| 2 | H | —CH(CH$_3$)OH<br>Thr T | H | —CH$_2$C(O)NH$_2$<br>Asn N | H | —CH(CH$_3$)OH<br>Thr T | H |
| 3 | H | —CH$_2$OH<br>Ser S | H | —CH$_2$C(O)OH<br>Asp D | H | —CH$_2$OH<br>Ser S | H |
| 4 | H | —CH$_2$OH<br>Ser S | H | —CH$_2$C(O)NH$_2$<br>Asn N | H | —(CH$_2$)$_4$—NH$_2$<br>Lys K | H |
| 5 | H | —CH$_2$-(p-OH(phenyl))<br>Tyr Y | H | —CH$_2$C(O)NH$_2$<br>Asn N | H | —CH(CH$_3$)OH<br>Thr T | H |
| 6 | Me | —CH$_2$OH<br>Ser S | H | —CH$_2$C(O)NH$_2$<br>Asn N | H | —CH(CH$_3$)OH<br>Thr T | H |
| 7 | H | —(CH$_2$)$_4$—NH$_2$<br>Lys K | H | —CH$_2$C(O)NH$_2$<br>Asn N | H | —CH(CH$_3$)OH<br>Thr T | H |
| 8 | H | —CH$_2$OH<br>Ser S | H | —CH$_2$(indolyl)<br>Trp W | H | —CH(CH$_3$)OH<br>Thr T | H |
| 9 | H | —CH$_2$OH<br>Ser S | H | Isopropyl<br>Val V | H | —CH(CH$_3$)OH<br>Thr T | H |
| 10 | H | —CH$_2$OH<br>Ser S | H | —CH$_2$C(O)NH(hexyl)<br>Asn N | H | —CH(CH$_3$)OH<br>Thr T | H |
| 11 | H | —(CH$_2$)$_2$C(O)NH$_2$<br>Gln Q | H | sec-butyl<br>Ile I | H | —(CH$_2$)$_2$C(O)OH<br>Glu E | H |
| 12 | H | —(CH$_2$)$_4$—NH$_2$<br>Lys K | H | —(CH$_2$)$_2$C(O)NH$_2$<br>Gln Q | H | —CH$_2$OH<br>Ser S | H |
| 13 | H | —CH$_2$OH<br>Ser S | H | —CH$_2$OH<br>Ser S | H | —CH$_2$OH<br>Ser S | H |
| 14 | H | —CH$_2$(imidazolyl)<br>His H | H | —CH$_2$C(O)OH<br>Asp D | H | —CH$_2$OH<br>Ser S | H |
| 15 | H | —(CH$_2$)$_3$—H(C=NH)—NH$_2$<br>Arg R | H | —CH$_2$C(O)OH<br>Asp D | H | —CH(CH$_3$)OH<br>Thr T | H |
| 16 | H | —(CH$_2$)$_3$—NH(C=NH)—NH$_2$<br>Arg R | H | —CH$_2$C(O)OH<br>Asp D | H | —CH$_2$OH<br>Ser S | H |
| 17 | H | —CH$_2$OH<br>Ser S | H | —(CH$_2$)$_4$—NH(COCH$_3$)<br>(acyl) Lys K | H | —CH(CH$_3$)OH<br>Thr T | H |
| 18 | H | —CH$_2$OH<br>Ser S | H | —(CH$_2$)$_2$C(O)NH(hexyl)<br>Gln Q | H | —CH(CH$_3$)OH<br>Thr T | H |
| 19 | H | Cyclohexyl ring | | —CH$_2$C(O)NH$_2$<br>Asn N | H | —CH(CH$_3$)OH<br>Thr T | H |
| 20 | H | —CH$_2$OH<br>Ser S | H | —CH$_2$C(O)NH$_2$<br>Asn N | H | —CH(CH$_3$)OH<br>D-Thr t | H |
| 21 | H | —CH$_2$OH<br>D-Ser s | H | —CH$_2$C(O)NH$_2$<br>Asn N | H | —CH(CH$_3$)OH<br>Thr T | H |
| 22 | H | —CH$_2$OH<br>D-Ser s | H | —CH$_2$C(O)NH$_2$<br>D-Asn n | H | —CH(CH$_3$)OH<br>D-Thr t | H |
| 23 | H | —CH$_2$OH<br>D-Ser s | H | —CH$_2$C(O)NH$_2$<br>Asn N | H | —CH(CH$_3$)OH<br>D-Thr t | H |
| 24 | H | —CH$_2$OH<br>D-Ser s | H | —CH$_2$C(O)NH$_2$<br>D-Asn n | H | —CH(CH$_3$)OH<br>Thr T | H |
| 25 | H | Cyclopentyl ring | | —CH$_2$C(O)NH$_2$<br>Asn N | H | —CH(CH$_3$)OH<br>Thr T | H |
| 26 | H | —(CH$_2$)$_2$COOH<br>Glu E | H | Pyrrolidine ring<br>Pro P | | —CH$_2$COOH<br>Asp D | H |
| 27 | H | —CH$_2$OH<br>Ser S | H | sec-butyl<br>Ile I | H | —CH(CH$_3$)OH<br>Thr T | H |

In some embodiments of the methods and compositions disclosed herein, the compound of formula (I) or a pharmaceutically acceptable salt thereof, is selected from:

TABLE 2

Exemplary Compounds of the Present Invention

| Cmd No. | G | $R_a$ | $R_{a'}$ | $R_b$ | $R_c$ | $R_d$ | $R_e$ |
|---|---|---|---|---|---|---|---|
| 1 | H | —CH$_2$OH<br>Ser S | H | —CH$_2$C(O)NH$_2$<br>Asn N | H | —CH(CH$_3$)OH<br>Thr T | H |
| 2 | H | —CH(CH$_3$)OH<br>Thr T | H | —CH$_2$C(O)NH$_2$<br>Asn N | H | —CH(CH$_3$)OH<br>Thr T | H |
| 3 | H | —CH$_2$OH<br>Ser S | H | —CH$_2$C(O)OH<br>Asp D | H | —CH$_2$OH<br>Ser S | H |
| 4 | H | —CH$_2$OH<br>Ser S | H | —CH$_2$C(O)NH$_2$<br>Asn N | H | —(CH$_2$)$_4$—NH$_2$<br>Lys K | H |
| 5 | H | —CH$_2$-(p-OH(phenyl))<br>Tyr Y | H | —CH$_2$C(O)NH$_2$<br>Asn N | H | —CH(CH$_3$)OH<br>Thr T | H |
| 6 | Me | —CH$_2$OH<br>Ser S | H | —CH$_2$C(O)NH$_2$<br>Asn N | H | —CH(CH$_3$)OH<br>Thr T | H |
| 7 | H | —(CH$_2$)$_4$—NH$_2$<br>Lys K | H | —CH$_2$C(O)NH$_2$<br>Asn N | H | —CH(CH$_3$)OH<br>Thr T | H |
| 8 | H | —CH$_2$OH<br>Ser S | H | —CH$_2$(indolyl)<br>Trp W | H | —CH(CH$_3$)OH<br>Thr T | H |
| 9 | H | —CH$_2$OH<br>Ser S | H | Isopropyl<br>Val V | H | —CH(CH$_3$)OH<br>Thr T | H |
| 10 | H | —CH$_2$OH<br>Ser S | H | —CH$_2$C(O)NH(hexyl)<br>Asn N | H | —CH(CH$_3$)OH<br>Thr T | H |
| 12 | H | —(CH$_2$)$_4$—NH$_2$<br>Lys K | H | —(CH$_2$)$_2$C(O)NH$_2$<br>Gln Q | H | —CH$_2$OH<br>Ser S | H |
| 13 | H | —CH$_2$OH<br>Ser S | H | —CH$_2$OH<br>Ser S | H | —CH$_2$OH<br>Ser S | H |
| 14 | H | —CH$_2$(imidazolyl)<br>His H | H | —CH$_2$C(O)OH<br>Asp D | H | —CH$_2$OH<br>Ser S | H |
| 16 | H | —(CH$_2$)$_3$—NH(C=NH)—NH$_2$<br>Arg R | H | —CH$_2$C(O)OH<br>Asp D | H | —CH$_2$OH<br>Ser S | H |
| 18 | H | —CH$_2$OH<br>Ser S | H | —(CH$_2$)$_2$C(O)NH(hexyl)<br>Gln Q | H | —CH(CH$_3$)OH<br>Thr T | H |
| 19 | H | Cyclohexyl ring | | —CH$_2$C(O)NH$_2$<br>Asn N | H | —CH(CH$_3$)OH<br>Thr T | H |
| 20 | H | —CH$_2$OH<br>Ser S | H | —CH$_2$C(O)NH$_2$<br>Asn N | H | —CH(CH$_3$)OH<br>D-Thr t | H |
| 21 | H | —CH$_2$OH<br>D-Ser s | H | —CH$_2$C(O)NH$_2$<br>Asn N | H | —CH(CH$_3$)OH<br>Thr T | H |
| 22 | H | —CH$_2$OH<br>D-Ser s | H | —CH$_2$C(O)NH$_2$<br>D-Asn n | H | —CH(CH$_3$)OH<br>D-Thr t | H |
| 23 | H | —CH$_2$OH<br>D-Ser s | H | —CH$_2$C(O)NH$_2$<br>Asn N | H | —CH(CH$_3$)OH<br>D-Thr t | H |

In certain embodiments of the methods and compositions disclosed herein, the compound of formula (I) or a pharmaceutically acceptable salt thereof, is selected from:

TABLE 3

Exemplary Compounds of the Present Invention

| Cmd No. | Structure |
|---|---|
| 1 | (structure shown) |
| 2 | (structure shown) |
| 3 | (structure shown) |

TABLE 3-continued

Exemplary Compounds of the Present Invention

| Cmd No. | Structure |
|---|---|
| 4 | 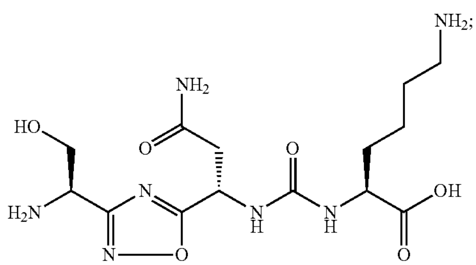 [SMILES: NCCCC[C@H](NC(=O)N[C@@H](CC(N)=O)c1nc([C@@H](N)CO)no1)C(=O)O] |
| 5 | 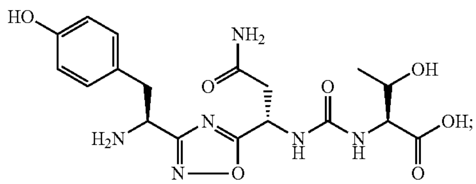 [SMILES: CC(O)[C@H](NC(=O)N[C@@H](CC(N)=O)c1nc([C@@H](N)Cc2ccc(O)cc2)no1)C(=O)O] |
| 6 | 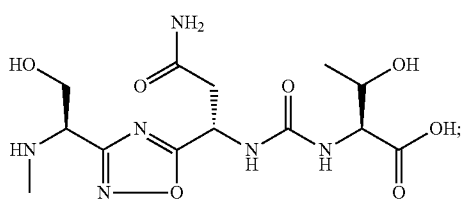 [SMILES: CN[C@@H](CO)c1noc([C@H](CC(N)=O)NC(=O)N[C@H](C(=O)O)C(C)O)n1] |
| 7 | 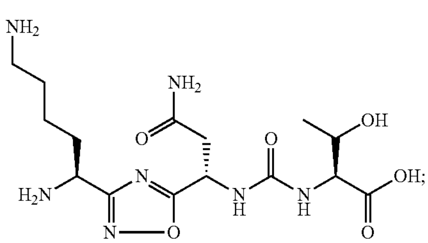 [SMILES: CC(O)[C@H](NC(=O)N[C@@H](CC(N)=O)c1nc([C@@H](N)CCCCN)no1)C(=O)O] |
| 8 | 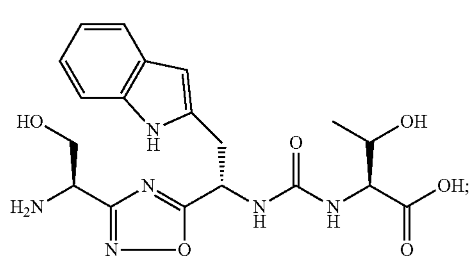 [SMILES: CC(O)[C@H](NC(=O)N[C@@H](Cc1cc2ccccc2[nH]1)c1nc([C@@H](N)CO)no1)C(=O)O] |
| 9 | 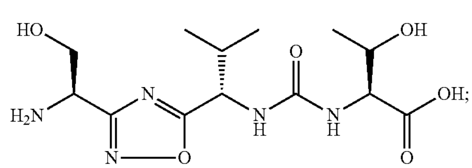 [SMILES: CC(O)[C@H](NC(=O)N[C@H](c1nc([C@@H](N)CO)no1)C(C)C)C(=O)O] |
| 10 | |
| 11 | |
| 12 | |
| 13 | |
| 14 | |
| 15 | |

TABLE 3-continued

Exemplary Compounds of the Present Invention

| Cmd No. | Structure |
|---|---|
| 16 | [structure] |
| 17 | [structure] |
| 18 | [structure] |
| 19 | [structure] |
| 20 | [structure] |
| 21 | [structure] |
| 22 | [structure] |
| 23 | [structure] |
| 24 | [structure] |
| 25 | [structure] |
| 26 | [structure]; or |
| 27 | [structure]. |

Dual inhibitors of VISTA and PD-1 (e.g., PD-1, PD-L1 or PD-L2) pathways are disclosed in International patent application PCT/IB2017/056463, which is hereby incorporated by reference in its entirety and in particular for the inhibitors disclosed therein.

In certain embodiments, the compound that inhibits the VISTA pathway is Cmd 1

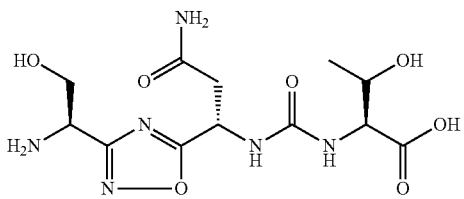 [SMILES: CC(O)[C@H](NC(=O)N[C@@H](CC(N)=O)c1nc([C@@H](N)CO)no1)C(=O)O]

or a pharmaceutically acceptable salt thereof.

In some embodiments, the Cmd 1 could also be written by showing all of the atoms,

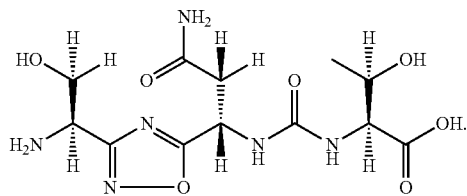

In certain embodiments, the compound that inhibits the TIM-3 pathway is Cmd 32

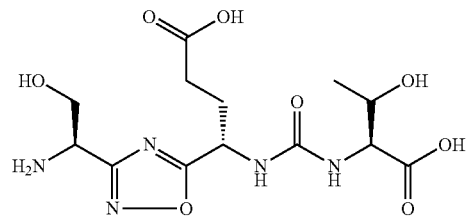

or a pharmaceutically acceptable salt thereof.

In some embodiments, the Cmd 32 could also be written by showing all of the atoms,

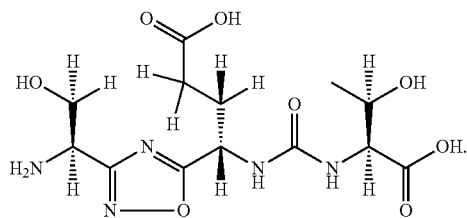

In certain embodiments of the methods and compositions disclosed herein, $R_a$ represents a side chain of an amino acid residue. In some embodiments, $R_c$ represents a side chain of an amino acid residue. In some embodiments, $R_d$ represents a side chain of an amino acid residue. In certain embodiments, $R_a$, $R_c$, and $R_d$ each represent a side chain of an amino acid residue.

Representative inhibitors of the TIM-3 pathway include compounds of having a structure formula (II) or a pharmaceutically acceptable salt thereof:

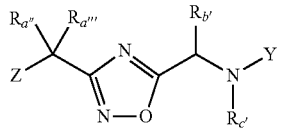

Formula (II)

wherein:
Z represents —OH or —NH-G';
G' represents hydrogen or $(C_1-C_6)$alkyl;
Y represents hydrogen or a group represented by the following structural formula

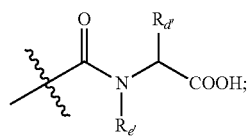

Ra" represents $(C_1-C_6)$alkyl substituted with —OH, —NRxRy, —SRx, carboxylic acid, guanidino or aryl, wherein the aryl group is optionally further substituted with hydroxyl; or Ra and G taken together with the atom to which they are attached form a 5- to 6-membered ring containing 1 to 3 heteroatoms selected from O, N or S;

Ra''' represents hydrogen; or Ra" and Ra''' taken together with the atom to which they are attached form a 5- to 6-membered ring, optionally containing 1 to 3 heteroatoms selected from O, N or S;

Rb' represents $(C_1-C_6)$alkyl, optionally substituted with —C(O)NRx'Ry', —NRxRy or carboxylic acid;

Rc' represents hydrogen; or Rb' and Rc' taken together with the atoms to which they are attached form a 5- to 6-membered ring containing 1 to 3 heteroatoms selected from O, N or S, wherein the 5- to 6-membered ring is optionally further substituted with hydroxyl;

Rd' represents $(C_1-C_6)$alkyl, optionally substituted with —ORx', carboxylic acid or aryl-OH;

Re' represents hydrogen; or Rd' and Re' taken together with the atoms to which they are attached form a 5- to 6-membered ring containing 1 to 3 heteroatoms selected from O, N or S; and Rx' and Ry' independently represent hydrogen, $(C_1-C_6)$alkyl or $(C_2-C_6)$acyl.

In some embodiments of Formula (II), Z represents —NH-G'. In some embodiments, G' represents hydrogen or methyl. In some embodiments, G' represents hydrogen.

Alternatively, in some embodiments of Formula (II), Z represents —OH.

In some embodiments, $R_{a''}$ represents $(C_1-C_4)$alkyl substituted with —OH, —NR$_x$R$_{y'}$, —NH(C=NH)—NH$_2$, —SR$_{x'}$, carboxylic acid or aryl, wherein the aryl group is optionally further substituted with hydroxyl. In certain embodiments of Formula (II), $R_{a''}$ represents $(C_1-C_4)$alkyl substituted with —OH, —NH$_2$, —NH(C=NH)—NH$_2$, —SCH$_3$, carboxylic acid, phenyl or p-OH(phenyl); and $R_{a'''}$ is hydrogen. In some embodiments of Formula (I), $R_{a''}$ represents $(C_1-C_4)$alkyl substituted with —OH, —NH$_2$, —NH(C=NH)—NH$_2$, carboxylic acid or phenyl; and $R_{a'''}$ is hydrogen. In some embodiments, $R_{a''}$ represents —CH$_2$OH, —CH(CH$_3$)OH, —(CH$_2$)$_4$—NH$_2$, —(CH$_2$)$_2$—SCH$_3$, —(CH$_2$)$_2$C(O)OH, —(CH$_2$)$_3$—NH—(C=NH)—NH$_2$, —CH$_2$-(phenyl) or —CH$_2$-(p-OH(phenyl)). In some embodiments, $R_{a''}$ represents —CH$_2$OH, —CH(CH$_3$)OH, —(CH$_2$)$_4$—NH$_2$, —(CH$_2$)$_2$C(O)OH, —(CH$_2$)$_3$—NH(C=NH)—NH$_2$ or —CH$_2$-(phenyl). In certain embodiments, R$_{a''}$ represents —CH$_2$OH or —CH(CH$_3$)OH. In some embodiments, R$_{a''}$ represents —CH$_2$OH.

Alternatively, in some embodiments, R$_{a''}$ and G' taken together with the atoms to which they are attached form a 5- to 6-membered ring containing 1 to 3 heteroatoms selected from O, N or S. In some embodiments, the 5- to 6-membered ring is a morpholine ring.

Alternatively, in certain embodiments, R$_{a''}$ and R$_{a'''}$ taken together with the atoms to which they are attached form a 5- to 6-membered ring, optionally containing 1 to 3 heteroatoms selected from O, N or S. In some embodiments, the 5- to 6-membered ring is a cyclopentyl ring.

In some embodiments, R$_{b'}$ represents (C$_1$-C$_4$)alkyl optionally substituted with —C(O)NR$_x$R$_{y'}$, —NR$_x$R$_{y'}$ or carboxylic acid. In some embodiments, R$_{b'}$ represents (C$_1$-C$_4$)alkyl, optionally substituted with —C(O)NH$_2$, —NH$_2$, —NH(C(O)CH$_3$) or carboxylic acid; and R$_{c'}$ represents hydrogen. In some embodiments, R$_{b'}$ represents (C$_1$-C$_4$)alkyl, optionally substituted with —C(O)NH$_2$, —NH(C(O)CH$_3$) or carboxylic acid; and R$_{c'}$ represents hydrogen. In some embodiments, R$_{b'}$ represents sec-butyl, —CH$_2$C(O)NH$_2$, —(CH$_2$)$_4$—NH$_2$, —(CH$_2$)$_4$—NH(C(O)CH$_3$), —CH$_2$C(O)OH or —(CH$_2$)$_2$C(O)OH. In some embodiments, R$_{b'}$ represents —CH$_2$C(O)NH$_2$, —(CH$_2$)$_4$—NH$_2$, —(CH$_2$)$_4$—NH(C(O)CH$_3$), —CH$_2$C(O)OH or —(CH$_2$)$_2$C(O)OH. In certain embodiments, R$_{b'}$ represents —CH$_2$C(O)NH$_2$, —CH$_2$C(O)OH or —(CH$_2$)$_2$C(O)OH. In some embodiments, R$_{b'}$ represents —CH$_2$C(O)OH or —(CH$_2$)$_2$C(O)OH.

Alternatively, in certain embodiments, R$_{b'}$ and R$_{c'}$ taken together with the atoms to which they are attached form a 5- to 6-membered ring containing 1 to 3 heteroatoms selected from O, N or S, wherein the 5- to 6-membered ring is optionally further substituted with hydroxyl. In some embodiments, the 5- to 6-membered ring is a pyrrolidine ring or piperdine ring, wherein the pyrrolidine ring is optionally further substituted with hydroxyl.

In some embodiments, Y represents a group represented by the following structural formula

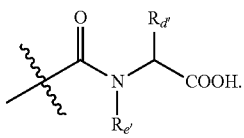

In certain embodiments, R$_{d'}$ represents (C$_1$-C$_4$)alkyl, optionally substituted with —OH, —OCH$_3$, —C(O)OH or p-OH(phenyl); and R$_{e'}$ represents hydrogen. In some embodiments, R$_{d'}$ represents isopropyl, sec-butyl, —CH$_2$OH, —CH(CH$_3$)OH, —CH(CH$_3$)OCH$_3$, —CH$_2$C(O)OH or —CH$_2$-(p-OH(phenyl)). In some embodiments, R$_{d'}$ represents sec-butyl, —CH$_2$OH or —CH(CH$_3$)OH. In certain embodiments, R$_{d'}$ represents —CH(CH$_3$)OH.

Alternatively, in certain embodiments, R$_{d'}$ and R$_{e'}$ taken together with the atoms to which they are attached form a 5- to 6-membered ring containing 1 to 3 heteroatoms selected from O, N or S. In some embodiments, the 5- to 6-membered ring is a pyrrolidine ring.

Alternatively, in some embodiments, Y represents hydrogen.

In some embodiments of Formula (II),
Z represents —OH or —NH-G';
G' represents hydrogen or (C$_1$-C$_6$)alkyl;
Y represents a group represented by the following structural formula

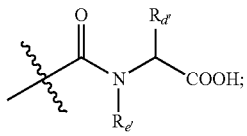

R$_{a''}$ represents (C$_1$-C$_6$)alkyl substituted with —OH, —NH$_2$, carboxylic acid, guanidino or aryl;
R$_{a'''}$ represents hydrogen; or R$_{a''}$ and R$_{a'''}$ taken together with the atom to which they are attached form a 5- to 6-membered ring, optionally containing 1 to 3 heteroatoms selected from O, N or S;
R$_{b'}$ represents (C$_1$-C$_6$)alkyl, optionally substituted with —C(O)NR$_x$R$_{y'}$ or carboxylic acid;
R$_{c'}$ represents hydrogen; or R$_{b'}$ and R$_{c'}$ taken together with the atoms to which they are attached form a 5- to 6-membered ring containing 1 to 3 heteroatoms selected from O, N or S;
R$_{d'}$ represents (C$_1$-C$_6$)alkyl, optionally substituted with —OR$_x$;
R$_{e'}$ represents hydrogen; or R$_{d'}$ and R$_{e'}$ taken together with the atoms to which they are attached form a 5- to 6-membered ring containing 1 to 3 heteroatoms selected from O, N or S; and
R$_x$ and R$_y$ independently represent hydrogen, (C$_1$-C$_6$)alkyl or (C$_2$-C$_6$)acyl.

In some embodiments of Formula (II),
Z represents —OH or —NH-G';
G' represents hydrogen or methyl;
Y represents hydrogen or a group represented by the following structural formula

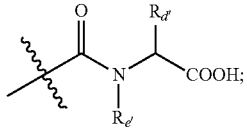

R$_{a''}$ represents —CH$_2$OH, —CH(CH$_3$)OH, —(CH$_2$)$_4$—NH$_2$, —(CH$_2$)$_2$—SCH$_3$, —(CH$_2$)$_2$C(O)OH, —(CH$_2$)$_3$—NH(C=NH)—NH$_2$, —CH$_2$-(phenyl) or —CH$_2$-(p-OH (phenyl)); or R$_a$ and G taken together with the atom to which they are attached form a morpholine ring;
R$_{a'''}$ represents hydrogen; or R$_{a''}$ and R$_{a''}$ taken together with the atoms to which they are attached form cyclopentyl ring;
R$_{b'}$ represents sec-butyl, —CH$_2$C(O)NH$_2$, —(CH$_2$)$_4$—NH$_2$, —(CH$_2$)$_4$—NH(C(O)CH$_3$), —CH$_2$C(O)OH or —(CH$_2$)$_2$C(O)OH;
R$_{c'}$ represents hydrogen; or R$_{b'}$ and R$_{c'}$ taken together with the atoms to which they are attached to form a pyrrolidine ring or piperdine ring, wherein the pyrrolidine ring is optionally further substituted with hydroxyl;
R$_{d'}$ represents isopropyl, sec-butyl, —CH$_2$OH, —CH(CH$_3$)OH, —CH(CH$_3$)OCH$_3$, —CH$_2$C(O)OH or —CH$_2$-(p-OH (phenyl)); and $R_{e'}$ represents hydrogen; or $R_{d'}$ and $R_{e'}$ taken together with the atoms to which they are attached to form a pyrrolidine ring.

In certain embodiments of Formula (II),

Z represents —OH or —NH-G';

G' represents hydrogen or methyl;

Y represents a group represented by the following structural formula

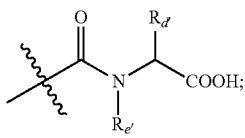

$R_{a''}$ represents —CH$_2$OH, —CH(CH$_3$)OH, —(CH$_2$)$_4$—NH$_2$, —(CH$_2$)$_2$C(O)OH, —(CH$_2$)$_3$—NH(C=NH)—NH$_2$ or —CH$_2$-(phenyl);

$R_{a'''}$ represents hydrogen;

$R_{b'}$ represents —CH$_2$C(O)NH$_2$, —CH$_2$C(O)OH or —(CH$_2$)$_2$C(O)OH;

$R_{c'}$ represents hydrogen; or $R_{b'}$ and $R_{c'}$ taken together with the atoms to which they are attached to form a pyrrolidine ring or piperdine ring;

$R_{d'}$ represents sec-butyl, —CH$_2$OH or —CH(CH$_3$)OH; and $R_{e'}$ represents hydrogen.

In certain embodiments, $R_{a''}$ represents —CH$_2$OH, —CH(CH$_3$)OH or —(CH$_2$)$_3$—NH(C=NH)—NH$_2$, $R_{b'}$ represents —CH$_2$C(O)NH$_2$, —CH$_2$C(O)OH or —(CH$_2$)$_2$C(O)OH; and $R_{d'}$ represents —CH$_2$OH or —CH(CH$_3$)OH. In some embodiments, $R_{a''}$ represents —CH$_2$OH or —CH(CH$_3$)OH; $R_{b'}$ represents —CH$_2$C(O)OH or —(CH$_2$)$_2$C(O)OH; and $R_{d'}$ represents —CH(CH$_3$)OH. In some embodiments, $R_{a''}$ represents —CH$_2$OH; $R_{b'}$ represents —CH$_2$C(O)OH or —(CH$_2$)$_2$C(O)OH; and $R_{d'}$ represents —CH(CH$_3$)OH. In some embodiments, $R_{a''}$ represents —CH(CH$_3$)OH; $R_{b'}$ represents —CH$_2$C(O)NH$_2$; and $R_{d'}$ represents —CH$_2$OH. In some embodiments, $R_{a''}$ represents —(CH$_2$)$_3$—NH(C=NH)—NH$_2$; $R_{b'}$ represents —CH$_2$C(O)NH$_2$; and $R_{d'}$ represents —CH$_2$OH.

In certain embodiments of the methods and compositions disclosed herein, the compound of Formula (II) or a pharmaceutically acceptable salt, is selected from:

TABLE 4

Exemplary Compounds of the Present Invention

| Cmd No. | Z | G' | $R_{a''}$ | $R_{a'''}$ | $R_{b'}$ | $R_{c'}$ | $R_{d'}$ | $R_{e'}$ |
|---|---|---|---|---|---|---|---|---|
| 28 | —NH-G' | H | —(CH$_2$)$_2$C(O)OH<br>Glu E | H | —CH$_2$C(O)NH$_2$<br>Asn N | H | —CH(CH$_3$)OH<br>Thr T | H |
| 29 | —NH-G' | H | —CH$_2$OH<br>Ser S | H | —CH$_2$C(O)NH$_2$<br>Asn N | H | sec-butyl<br>Ile I | H |
| 30 | —NH-G' | H | —CH$_2$-(phenyl)<br>Phe F | H | —CH$_2$C(O)NH$_2$<br>Asn N | H | —CH(CH$_3$)OH<br>Thr T | H |
| 31 | —NH-G' | H | —CH$_2$OH<br>Ser S | H | —CH$_2$C(O)OH<br>Asp D | H | —CH(CH$_3$)OH<br>Thr T | H |
| 32 | —NH-G' | CH$_3$ | —CH$_2$OH<br>Ser S | H | —(CH$_2$)$_2$C(O)OH<br>Glu E | H | —CH(CH$_3$)OH<br>Thr T | H |
| 33 | —NH-G' | H | —(CH$_2$)$_4$—NH$_2$<br>Lys K | H | —(CH$_2$)$_2$C(O)OH<br>Glu E | H | —CH(CH$_3$)OH<br>Thr T | H |
| 34 | —NH-G' | H | —CH$_2$OH<br>Ser S | H | —CH$_2$C(O)NH$_2$<br>D-Asn n | H | —CH(CH$_3$)OH<br>Thr T | H |
| 35 | —NH-G' | H | —CH(CH$_3$)OH<br>D-Thr t | H | —CH$_2$C(O)NH$_2$<br>D-Asn n | H | —CH$_2$OH<br>D-Ser s | H |
| 36 | —NH-G' | H | —(CH$_2$)$_4$—NH$_2$<br>Lys K | H | —CH$_2$C(O)NH$_2$<br>Asn N | H | isopropyl<br>Val V | H |
| 37 | —NH-G' | H | —(CH$_2$)$_2$SCH$_3$<br>Met M | H | —CH$_2$C(O)NH$_2$<br>Asn N | H | —CH$_2$C(O)OH<br>Asp D | H |
| 38 | —NH-G' | H | —(CH$_2$)$_4$—NH$_2$<br>Lys K | H | —(CH$_2$)$_2$C(O)OH<br>Glu E | H | —CH$_2$OH<br>Ser S | H |
| 39 | —NH-G' | H | —(CH$_2$)$_4$—NH$_2$<br>Lys K | H | —CH$_2$C(O)NH$_2$<br>Asn N | H | —CH$_2$OH<br>Ser S | H |
| 40 | —NH-G' | H | —CH$_2$OH<br>Ser S | H | —(CH$_2$)$_4$—NH$_2$<br>Lys K | H | —CH(CH$_3$)OH<br>Thr T | H |
| 41 | —NH-G' | H | —CH$_2$OH<br>Ser S | H | —CH$_2$C(O)NH$_2$<br>Asn N | H | —CH(CH$_3$)OMe<br>Thr T(OMe) | H |
| 42 | —NH-G' | H | —CH$_2$OH<br>Ser S | H | sec-butyl<br>Ile I | H | —CH(CH$_3$)OH<br>Thr T | H |
| 43 | —NH-G' | | Morpholine | | —CH$_2$C(O)NH$_2$<br>Asn N | H | —CH(CH$_3$)OH<br>Thr T | |
| 44 | —NH-G' | | Morpholine | | —(CH$_2$)$_2$C(O)OH<br>Glu E | H | —CH(CH$_3$)OH<br>Thr T | |
| 45 | —NH-G' | H | —CH$_2$-(p-OH(phenyl))<br>Tyr Y | H | -(4-OH-(pyrrolidine ring))<br>Hydroxy-Pro | | —CH$_2$-(p-OH(phenyl))<br>Tyr Y | H |
| 46 | —NH-G' | H | —CH$_2$-(p-OH(phenyl))<br>Tyr Y | H | -(piperdine) | | —CH$_2$-(p-OH(phenyl))<br>Tyr Y | H |
| 47 | —NH-G' | H | —CH$_2$OH<br>Ser S | H | —(CH$_2$)$_4$—NH(C(O)CH$_3$)<br>Lys K(acyl) | H | —CH(CH$_3$)OH<br>Thr T | H |
| 48 | —NH-G' | H | —CH$_2$-(p-OH(phenyl))<br>Tyr Y | H | —CH$_2$C(O)NH$_2$<br>Asn N | H | —CH(CH$_3$)OH<br>Thr T | H |
| 49 | —NH-G' | H | —CH$_2$OH<br>Ser S | H | —CH$_2$C(O)NH$_2$<br>Asn N | H | —CH(CH$_3$)OH<br>D-Thr t | H |

TABLE 4-continued

Exemplary Compounds of the Present Invention

| Cmd No. | Z | G' | $R_{a''}$ | $R_{a'''}$ | $R_{b'}$ | $R_{c'}$ | $R_{d'}$ | $R_{e'}$ |
|---|---|---|---|---|---|---|---|---|
| 50 | —NH-G' | H | Cyclopentyl ring | | —CH$_2$C(O)NH$_2$<br>Asn N | H | —CH(CH$_3$)OH<br>Thr T | H |
| 51 | —OH | — | —CH$_2$OH<br>Ser S | H | —CH$_2$C(O)NH$_2$<br>Asn N | H | —CH(CH$_3$)OH<br>Thr T | H |
| 52 | —NH-G' | H | —(CH$_2$)$_3$—NH(C=NH)—NH$_2$<br>Arg R | H | —CH$_2$C(O)NH$_2$<br>Asn N | H | —CH$_2$OH<br>Ser S | H |
| 53 | —NH-G' | CH$_3$ | —CH$_2$OH<br>Ser S | H | —CH$_2$C(O)NH$_2$<br>Asn N | H | — | — |

In some embodiments of the methods and compositions disclosed herein, the compound of Formula (II) or a pharmaceutically acceptable salt, is selected from:

TABLE 4A

Exemplary Compounds of the Present Invention

| Cmd No. | Z | G | $R_a$ | $R_{a'}$ | $R_b$ | $R_c$ | $R_d$ | $R_e$ |
|---|---|---|---|---|---|---|---|---|
| 28 | —NH-G | H | —(CH$_2$)$_2$C(O)OH<br>Glu E | H | —CH$_2$C(O)NH$_2$<br>Asn N | H | —CH(CH$_3$)OH<br>Thr T | H |
| 29 | —NH-G | H | —CH$_2$OH<br>Ser S | H | —CH$_2$C(O)NH$_2$<br>Asn N | H | sec-butyl<br>Ile I | H |
| 30 | —NH-G | H | —CH$_2$-(phenyl)<br>Phe F | H | —CH$_2$C(O)NH$_2$<br>Asn N | H | —CH(CH$_3$)OH<br>Thr T | H |
| 31 | —NH-G | H | —CH$_2$OH<br>Ser S | H | —CH$_2$C(O)OH<br>Asp D | H | —CH(CH$_3$)OH<br>Thr T | H |
| 32 | —NH-G | H | —CH$_2$OH<br>Ser S | H | —(CH$_2$)$_2$C(O)OH<br>Glu E | H | —CH(CH$_3$)OH<br>Thr T | H |
| 33 | —NH-G | H | —(CH$_2$)$_4$—NH$_2$<br>Lys K | H | —(CH$_2$)$_2$C(O)OH<br>Glu E | H | —CH(CH$_3$)OH<br>Thr T | H |
| 34 | —NH-G | H | —CH$_2$OH<br>Ser S | H | —CH$_2$C(O)NH$_2$<br>D-Asn n | H | —CH(CH$_3$)OH<br>Thr T | H |
| 35 | —NH-G | H | —CH(CH$_3$)OH<br>D-Thr t | H | —CH$_2$C(O)NH$_2$<br>D-Asn n | H | —CH$_2$OH<br>D-Ser s | H |
| 36 | —NH-G | H | —(CH$_2$)$_4$—NH$_2$<br>Lys K | H | —CH$_2$C(O)NH$_2$<br>Asn N | H | isopropyl<br>Val V | H |
| 37 | —NH-G | H | —(CH$_2$)$_2$SCH$_3$<br>Met M | H | —CH$_2$C(O)NH$_2$<br>Asn N | H | —CH$_2$C(O)OH<br>Asp D | H |
| 38 | —NH-G | H | —(CH$_2$)$_4$—NH$_2$<br>Lys K | H | —(CH$_2$)$_2$C(O)OH<br>Glu E | H | —CH$_2$OH<br>Ser S | H |
| 39 | —NH-G | H | —(CH$_2$)$_4$—NH$_2$<br>Lys K | H | —CH$_2$C(O)NH$_2$<br>Asn N | H | —CH$_2$OH<br>Ser S | H |
| 40 | —NH-G | H | —CH$_2$OH<br>Ser S | H | —(CH$_2$)$_4$—NH$_2$<br>Lys K | H | —CH(CH$_3$)OH<br>Thr T | H |
| 41 | —NH-G | H | —CH$_2$OH<br>Ser S | H | —CH$_2$C(O)NH$_2$<br>Asn N | H | —CH(CH$_3$)OMe<br>Thr T(OMe) | H |
| 42 | —NH-G | | Morpholine | | —CH$_2$C(O)NH$_2$<br>Asn N | H | —CH(CH$_3$)OH<br>Thr T | H |
| 43 | —NH-G | | Morpholine | | —(CH$_2$)$_2$C(O)OH<br>Glu E | H | —CH(CH$_3$)OH<br>Thr T | H |
| 44 | —NH-G | H | —CH$_2$-(p-OH(phenyl))<br>Tyr Y | H | -(4-OH-(pyrrolidine ring))<br>Hydroxy-Pro | | —CH$_2$-(p-OH(phenyl))<br>Tyr Y | H |
| 45 | —NH-G | H | —CH$_2$-(p-OH(phenyl))<br>Tyr Y | H | -(piperidine) | | —CH$_2$-(p-OH(phenyl))<br>Tyr Y | H |
| 46 | —NH-G | H | —CH$_2$OH<br>Ser S | H | —(CH$_2$)$_4$—NH(C(O)CH$_3$)<br>Lys K(acyl) | H | —CH(CH$_3$)OH<br>Thr T | H |
| 51 | —OH | — | —CH$_2$OH<br>Ser S | H | —CH$_2$C(O)NH$_2$<br>Asn N | H | —CH(CH$_3$)OH<br>Thr T | H |
| 52 | —NH-G | H | —(CH$_2$)$_3$—NH—C(=NH)—NH$_2$<br>Arg R | H | —CH$_2$C(O)NH$_2$<br>Asn N | H | —CH$_2$OH<br>Ser S | H |
| 53 | —NH-G | CH$_3$ | —CH$_2$OH<br>Ser S | H | —CH$_2$C(O)NH$_2$<br>Asn N | H | — | — |

In some embodiments of the methods and compositions disclosed herein, the compound of Formula (II) or a pharmaceutically acceptable salt, is selected from:

TABLE 5

Exemplary Compounds of the Present Invention

| Cmd No. | Z | G' | $R_{a''}$ | $R_{a'''}$ | $R_{b'}$ | $R_{c'}$ | $R_{d'}$ | $R_{e'}$ |
|---|---|---|---|---|---|---|---|---|
| 28 | —NH-G' | H | —$(CH_2)_2C(O)OH$<br>Glu E | H | —$CH_2C(O)NH_2$<br>Asn N | H | —$CH(CH_3)OH$<br>Thr T | H |
| 29 | —NH-G' | H | —$CH_2OH$<br>Ser S | H | —$CH_2C(O)NH_2$<br>Asn N | H | sec-butyl<br>Ile I | H |
| 30 | —NH-G' | H | —$CH_2$-(phenyl)<br>Phe F | H | —$CH_2C(O)NH_2$<br>Asn N | H | —$CH(CH_3)OH$<br>Thr T | H |
| 31 | —NH-G' | H | —$CH_2OH$<br>Ser S | H | —$CH_2C(O)OH$<br>Asp D | H | —$CH(CH_3)OH$<br>Thr T | H |
| 32 | —NH-G' | $CH_3$ | —$CH_2OH$<br>Ser S | H | —$(CH_2)_2C(O)OH$<br>Glu E | H | —$CH(CH_3)OH$<br>Thr T | H |
| 33 | —NH-G' | H | —$(CH_2)_4$—$NH_2$<br>Lys K | H | —$(CH_2)_2C(O)OH$<br>Glu E | H | —$CH(CH_3)OH$<br>Thr T | H |
| 34 | —NH-G' | H | —$CH_2OH$<br>Ser S | H | $CH_2C(O)NH_2$<br>D-Asn n | H | —$CH(CH_3)OH$<br>Thr T | H |
| 35 | —NH-G' | H | —$CH(CH_3)OH$<br>D-Thr t | H | $CH_2C(O)NH_2$<br>D-Asn n | H | —$CH_2OH$<br>D-Ser s | H |
| 51 | —OH | — | —$CH_2OH$<br>Ser S | H | —$CH_2C(O)NH_2$<br>Asn N | H | —$CH(CH_3)OH$<br>Thr T | H |
| 52 | —NH-G' | H | —$(CH_2)_3$—$NH(C=NH)$—$NH_2$<br>Arg R | H | —$CH_2C(O)NH_2$<br>Asn N | H | —$CH_2OH$<br>Ser S | H |

In certain embodiments of the methods and compositions disclosed herein, the compound of Formula (II) or a pharmaceutically acceptable salt, is selected from:

TABLE 6

Exemplary Compounds of the Present Invention

| Cmd No. | Structure |
|---|---|
| 28 | (structure) |
| 29 | (structure) |
| 30 | (structure) |
| 31 | (structure) |
| 32 | (structure) |
| 33 | (structure) |

TABLE 6-continued

Exemplary Compounds of the Present Invention

| Cmd No. | Structure |
|---|---|
| 34 | (chemical structure) |
| 35 | (chemical structure) |
| 36 | (chemical structure) |
| 37 | (chemical structure) |
| 38 | (chemical structure) |
| 39 | (chemical structure) |
| 40 | (chemical structure) |
| 41 | (chemical structure) |
| 42 | (chemical structure) |
| 43 | (chemical structure) |
| 44 | (chemical structure) |
| 45 | (chemical structure) |

TABLE 6-continued

Exemplary Compounds of the Present Invention

| Cmd No. | Structure |
|---|---|
| 46 | [structure] |
| 47 | [structure] |
| 48 | [structure] |
| 49 | [structure] |
| 50 | [structure] |
| 51 | [structure] |

TABLE 6-continued

Exemplary Compounds of the Present Invention

| Cmd No. | Structure |
|---|---|
| 52 | [structure]; and |
| 53 | [structure]. |

In certain embodiments of the methods and compositions disclosed herein, the compound or a pharmaceutically acceptable salt thereof, is selected from:

TABLE 6A

Exemplary Compounds of the Present Invention

| Cmd No. | Structure |
|---|---|
| 1 | [structure]; |
| 2 | [structure]; |
| 3 | [structure]; |
| 4 | [structure]; |

TABLE 6A-continued

Exemplary Compounds of the Present Invention

| Cmd No. | Structure |
|---|---|
| 5 | (chemical structure) |
| 6 | (chemical structure) |
| 7 | (chemical structure) |
| 8 | (chemical structure) |
| 9 | (chemical structure) |
| 10 | (chemical structure) |
| 11 | (chemical structure) |
| 12 | (chemical structure) |
| 13 | (chemical structure) |
| 14 | (chemical structure) |
| 16 | (chemical structure) |

TABLE 6A-continued

Exemplary Compounds of the Present Invention

| Cmd No. | Structure |
|---|---|
| 17 | [structure] |
| 18 | [structure] |
| 19 | [structure] |
| 20 | [structure] |
| 24 | [structure]; and |
| 25 | [structure]. |

Dual inhibitors of TIM-3 and PD-1 (e.g., PD-1, PD-L1 or PD-L2) pathways are disclosed in Indian patent application 201741039298, which is hereby incorporated by reference in its entirety and in particular for the inhibitors disclosed therein.

In certain embodiments of the methods and compositions disclosed herein, $R_a$ represents a side chain of an amino acid residue. In some embodiments, $R_b$ represents a side chain of an amino acid residue. In some embodiments, $R_d$ represents a side chain of an amino acid residue. In certain embodiments, $R_a$, $R_b$, and $R_d$ each represent a side chain of an amino acid residue.

An amino acid residue is understood in the art to mean a carboxylic acid, substituted at the alpha, beta or gamma carbon by an amino (—NH$_2$) group. In the group —CO-Aaa, the amino acid residue Aaa is connected to the carbonyl group CO via a covalent bond between the carbonyl carbon and the amino group of the amino acid residue. In preferred embodiments, the amino acid is an alpha-amino acid, and the amino acid residue Aaa is connected to the carbonyl group CO via a covalent bond between the carbonyl carbon and the alpha-amino group of the amino acid residue.

In accordance with any of the foregoing embodiments, in certain embodiments, one, more than one or all amino acid residues are D amino acid residues. In some embodiments, one, more than one or all amino acid residue side chains correspond to the stereochemistry of D amino acid residues.

In certain embodiments, one, more than one or all amino acid residues are L amino acid residues. In some embodiments, one, more than one or all amino acid residue side chains correspond to the stereochemistry of L amino acid residues.

In certain embodiments of the methods and compositions disclosed herein, the compounds may be prodrugs of the compounds of Formula (I) and Formula (II), e.g., wherein a hydroxyl in the parent compound is presented as an ester or a carbonate or carboxylic acid present in the parent compound is presented as an ester. In a further embodiment, the prodrug is metabolized to the active parent compound in vivo (e.g., the ester is hydrolyzed to the corresponding hydroxyl or carboxylic acid).

Throughout this specification and claims, the 'L-threonine residue' mentioned in compound of formula (I) or compounds of the present invention and/or preparation thereof can be represented by any one of the following formulae.

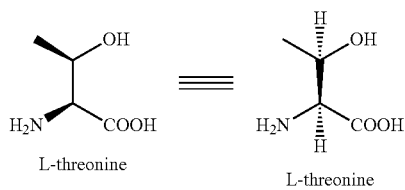 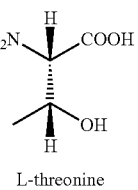 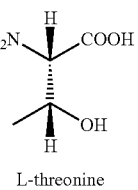 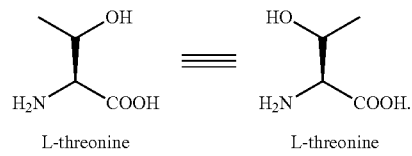 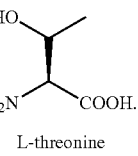

In certain embodiments of the methods and compositions disclosed herein, the compounds of the present disclosure can also contain unnatural proportions of atomic isotopes at one or more of the atoms that constitute such compounds. For example, the present disclosure also embraces isotopically-labeled variants of the present disclosure which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the disclosure, and their uses. Exemplary isotopes that can be incorporated in to compounds of the disclosure include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{35}$S, $^{18}$F, $^{36}$Cl, $^{123}$I and $^{125}$I. Isotopically labeled compounds of the present disclosures can generally be prepared by following procedures analogous to those disclosed in the schemes and/or in the examples herein below, by substituting an isotopically labeled reagent for a non-isotopically labeled reagent.

Methods of Use

In some embodiments, the present disclosure provides a method of modulating an immune response mediated by VISTA and TIM-3 activity in a cell, comprising contacting the cell with a compound of Formula (I) and a compound of Formula (II) or a pharmaceutically acceptable salt thereof, according to any of the above embodiments. In some embodiments, the present disclosure provides a method of modulating an immune response mediated by the PD-1 (e.g., PD-1, PD-L1 or PD-L2) signaling pathway, VISTA and TIM-3 activity in a cell, comprising contacting the cell with a compound of Formula (I) and a compound of Formula (II) or a pharmaceutically acceptable salt thereof, according to any of the above embodiments.

In certain embodiments, the present disclosure provides uses of a compound of Formula (I) and a compound of Formula (II) for the preparation of a medicament, e.g., for the treatment of cancer, immune disorders, immunodeficiency disorders, inflammatory disorders, infectious diseases, and transplant rejection.

In accordance with any of the foregoing embodiments, in certain embodiments, contacting the cell occurs in a subject in need thereof, thereby treating a disease or disorder selected from cancer, immune disorders, immunodeficiency disorders, inflammatory disorders, infectious diseases, and transplant rejection.

In certain embodiments, the present disclosure provides methods for treating cancer, wherein the method comprises conjoint administration of a therapeutically effective amount of a compound of Formula (I) and a compound of Formula (II) to the subject in need thereof.

In certain embodiments, the present disclosure provides methods for inhibiting growth of tumor cells and/or metastasis by conjointly administering a therapeutically effective amount of a compound of Formula (I) and a compound of Formula (II) to the subject in need thereof.

In certain embodiments, the tumor cells are from a cancer selected from small cell lung cancer, multiple myeloma, bladder carcinoma, primary ductal carcinoma, ovarian carcinoma, Hodgkin's lymphoma, gastric carcinoma, acute myeloid leukemia, and pancreatic cancer.

Representative tumor cells include cells of a cancer such as, but not limited to, blastoma (e.g., glioblastoma), breast cancer (e.g., breast carcinoma, primary ductal carcinoma, triple negative breast cancer, estrogen receptor positive (ER+), progesterone receptor positive (PR+), and/or human epidermal growth factor receptor 2 positive (HER2+)), epithelial cancer (e.g., carcinomas), colon cancer, lung cancer (e.g., small cell lung cancer, non-small cell lung cancer (NSCLC), lung adenocarcinoma, and lung squamous cell carcinoma), melanoma (e.g., cutaneous melanoma, ocular melanoma, cutaneous or intraocular malignant melanoma, and lymph node-associated melanoma), prostate cancer (e.g., prostate adenocarcinoma), renal cancer (e.g., renal cell cancer (RCC) and kidney cancer), bone cancer (e.g., osteosarcoma), pancreatic cancer (e.g., pancreatic adenocarcinoma), skin cancer, cancer of the head or neck (e.g., head and neck squamous cell carcinoma), uterine cancer, ovarian cancer (e.g., ovarian carcinoma), colorectal cancer (e.g., microsatellite instability high colorectal cancer and colorectal adenocarcinoma), rectal cancer, cancer of the anal region, cancer of the peritoneum, stomach cancer (e.g., gastric carcinoma and gastrointestinal cancer), testicular cancer, carcinoma of the fallopian tubes, carcinoma of the endometrium, cervical cancer (e.g., carcinoma of the cervix), vaginal cancer (e.g., carcinoma of the vagina), vulval cancer (e.g., carcinoma of the vulva), cancer of the esophagus, cancer of the small intestine, cancer of the endocrine system, thyroid cancer (e.g., cancer of the thyroid gland), cancer of the parathyroid gland, cancer of the adrenal gland, sarcoma (e.g., sarcoma of soft tissue and Kaposi's sarcoma), cancer of the urethra, cancer of the penis, chronic or acute leukemia, (e.g., acute myeloid leukemia, chronic myeloid leukemia, acute lymphoblastic leukemia, chronic lymphocytic leukemia, Hairy cell leukemia, and chronic myeloblastic leukemia), solid tumors of childhood, Hodgkin's lymphoma (HL) (e.g., lymphocyte-rich (LRCHL), nodular sclerosis (NSHL), mixed cellularity (MCHL) and lymphocyte depleted (LDHL)), B-cell lymphomas (e.g., diffuse large B-cell lymphoma (DLBCL)), non-Hodgkin's lymphoma (NEIL) (e.g., low grade/follicular non-Hodgkin's lymphoma, small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Burkitt's lymphoma, mantle cell lymphoma), AIDS-related lymphoma, cutaneous T-cell lymphoma (e.g., mycosis fundoides) and Waldenstrom's Macroglobulinemia, post-transplant lymphoproliferative disorder (PTLD), lymphocytic lymphoma, primary CNS lymphoma, and T-cell lymphoma), mesothelioma, thymic carcinoma, myeloma (e.g., multiple myeloma), cancer of the bladder (e.g., bladder carcinoma), cancer of the ureter, carcinoma of the renal pelvis, liver cancer (e.g., hepatocellular cancer, hepatic carcinoma, hepatoma), pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, environmentally induced cancers (including those induced by asbestos), and combinations of said cancers.

In some embodiments, for example, the tumor cells may include cells of a cancer selected from prostate cancer, melanoma, breast cancer, colon cancer, prostate cancer, lung cancer, renal cancer, pancreatic cancer, gastric carcinoma, bladder cancer, esophageal cancer, mesothelioma, thyroid cancer, thymic carcinoma, sarcoma, glioblastoma, chronic or acute leukemia, lymphoma, myeloma, Merkel cell carcinoma, epithelial cancer, colorectal cancer, vaginal cancer, cervical cancer, ovarian cancer, and cancer of the head and neck.

In some embodiments, for example, the tumor cells may include cells of a cancer selected from melanoma, triple negative breast cancer, non-small cell lung cancer, renal cell carcinoma, pancreatic cancer, gastric carcinoma, bladder cancer, mesothelioma, Hodgkins's lymphoma, cervical cancer, ovarian cancer, and head and neck squamous cell carcinoma.

In some embodiments, the tumor cells are, and/or the subject is, naïve to immunooncology therapy. Immunooncology uses the subject's immune system to help fight cancer. For example, an immunooncology therapy includes, but is not limited to, alemtumzuamb, atezolizumab (human monoclonal antibody that targets PD-L1), avelumab (human monoclonal antibody that targets PD-L1), brentuximab vedotin (antibody-drug conjugate that targets CD30), durvalamab (human monoclonal antibody that targets PD-L1), ipilimumab (human monoclonal antibody that targets CTLA-4), nivolumab (human monoclonal antibody that targets PD-L1), pembrolizumab (also referred to as lambrolizumab, human monoclonal antibody that targets PD-L1), rituxan, tremelimumab (human monoclonal antibody that targets CTLA-4), CT-011 (antibody that targets PD-1), MDX-1106 (antibody that targets PD-1), MK-3475 (antibody that targets PD-1), YW243.55.S70 (antibody that targets PD-L1), MPDL3280A (antibody that targets PD-L1), MDX-1105 (antibody that targets PD-L1), and MEDI4736 (antibody that targets PD-L1). In some embodiments, the immunooncology therapy is selected from an anti-CTLA-4 antibody, an anti-PD-1 antibody, an anti-PD-L1 antibody, an anti-PD-L2 antibody, an anti-TIGIT antibody (e.g., antibodies disclosed in WO 2015/009856). In some embodiments, the immunooncology therapy is an indoleamine 2,3-dioxygenase (IDO) inhibitor (e.g. INCB24360 (Epacadostat). In some embodiments, the immunooncology therapy is an arginase inhibitor (e.g., CB-1158). In some embodiments, the immunooncology therapy is interleukin 2 (IL-2). In some embodiments, the immunooncology therapy is a vaccine (e.g., Sipuleucel-T). In some embodiments, the immunooncology therapy is a chimeric antigen T cell receptor (CAR-T) therapy (e.g., Tisagenlecleucel, Axicabtagene Ciloleuce).

In some embodiments, a biological sample comprises tumor cells of a cancer where response to immune checkpoint therapy has been demonstrated, either by testing of a sampling of representative tumors of that type or by testing a patient's own tumor. In some embodiments, the cancer has shown response to anti-PD1 therapy, e.g., by testing of a sampling of representative tumors of that type. For example, the cancer may include non-small cell lung cancer (NSCLC), melanoma, renal cell cancer (RCC), cancer of the bladder, Hodgkin's lymphoma, and head and neck squamous cell carcinoma.

In some embodiments, a biological sample comprises tumor cells that are refractory or resistant to one or more PD-1 antagonists.

In certain embodiments, a biological sample comprises tumor cells of a cancer where VISTA and TIM-3 are expressed in the absence of PD-L1 and PD-L2. In some embodiments, the biological sample comprises tumor cells, stroma, and immune infiltrate. For example, in some embodiments where VISTA and TIM-3 are expressed in the absence of PD-L1 and PD-L2, the biological sample comprises tumor cells of a cancer such as small cell lung cancer, multiple myeloma, bladder carcinoma, primary ductal carcinoma, ovarian carcinoma, Hodgkin's lymphoma, gastric carcinoma, acute myeloid leukemia, and pancreatic cancer.

In some embodiments, a biological sample comprises tumor cells of a cancer where there is not a correlation between VISTA, TIM-3 and PD-L1 expression. For example, the biological sample may include tumor cells of a cancer such as carcinoma of the endometrium, ovarian cancer, Hodgkin's lymphoma, non-Hodgkin's lymphoma, and chronic or acute leukemias including acute myeloid leukemia, chronic myeloid leukemia, acute lymphoblastic leukemia, chronic lymphocytic leukemia, lymphocytic lymphoma, and multiple myeloma.

In some embodiments, a biological sample comprises tumor cells of a cancer where the tumor cells express VISTA, TIM-3 and PD-L1. For example, tumor cells include cells of a cancer such as prostate adenocarcinoma, lung adenocarcinoma, lung squamous cell carcinoma, pancreatic adenocarcinoma, breast cancer and colorectal adenocarcinoma. In certain embodiments, tumor cells are from breast cancer. In some embodiments, the tumor cells are from a breast cancer selected from triple negative breast cancer, estrogen receptor positive (ER+), progesterone receptor positive (PR+), and/or human epidermal growth factor receptor 2 (HER2+). In some embodiments, the tumor cells are from a PAM50+ breast cancer assay panel (Parker, J. S., et al., J. Clin. Oncol., 2009, 27(8): 1160-1167), breast cancer selected from luminal A, luminal B, HER2-enriched, basal-like and normal-like.

In some embodiments, a biological sample comprises tumor cells of a cancer where tumor clearance is dependent on myeloid cells, natural killer (NK) cells or NKT cells. In some embodiments, a biological sample comprises tumor cells of a cancer where clearance is dependent on CD8+ T cells. For example, the cancer may include triple negative breast cancer, microsatellite instability high colorectal cancer, gastric carcinoma, mesothelioma, pancreatic cancer, and cervical cancer.

In some embodiments of the present disclosure provide a method of treatment of infection by inhibition of the VISTA and TIM-3 pathways or by inhibition of the VISTA, TIM-3, and PD-1 (e.g., PD-1, PD-L1 or PD-L2) pathways.

In some embodiments of the present disclosure provide a method of treatment of infection by blockade of the PD-1 (e.g., PD-1, PD-L1 or PD-L2) pathway with conjoint inhibition of VISTA and TIM-3, e.g., by conjoint administration of a therapeutically effective amount of a compound of Formula (I) and a compound of Formula (II) to the subject in need thereof.

In certain embodiments, the present disclosure provides uses of a compound of the present disclosure for the preparation of a medicament for the treatment of infectious disease, as well as methods of conjointly administering a therapeutically effective amount of a compound of Formula (I) and a compound of Formula (II) for the treatment of infectious disease.

In some embodiments, the infectious disease is bacterial infection, viral infection, fungal infection or parasitic infection, as well as methods of conjointly administering a therapeutically effective amount of a compound of Formula (I) and a compound of Formula (II) for the treatment of bacterial infection, viral infection, fungal infection or parasitic infection.

In some embodiments, for example, bacterial infection may be caused by at least one bacterium selected from anthrax, Bacilli, *Bordetella, Borrelia*, botulism, *Brucella, Burkholderia, Campylobacter, Chlamydia*, cholera, *Clostridium, Conococcus, Corynebacterium*, diptheria, *Enterobacter, Enterococcus, Erwinia, Escherichia, Francisella, Haemophilus, Heliobacter, Klebsiella, Legionella, Leptospira*, leptospirosis, *Listeria*, Lyme's disease, *Meningococcus, Mycobacterium, Mycoplasma, Neisseria, Pasteurella, Pelobacter*, plague, *Pneumonococcus, Proteus, Pseudomonas, Rickettsia, Salmonella, Serratia, Shigella, Staphylococcus, Streptococcus*, tetanus, *Treponema, Vibrio, Yersinia* and *Xanthomonas*.

In some embodiments, for example, viral infection may be caused by at least one virus selected from Adenoviridae, Papillomaviridae, Polyomaviridae, Herpesviridae, Poxviridae, Hepadnaviridae, Parvoviridae, Astroviridae, Caliciviridae, Picornaviridae, Coronoviridae, Flaviviridae, Retroviridae, Togaviridae, Arenaviridae, Bunyaviridae, Filoviridae orthomyxoviridae, Paramyxoviridae, Rhabdoviridae, and Reoviridae. In certain embodiments, the virus may be arboviral encephalitis virus, adenovirus, herpes simplex type I, herpes simplex type 2, Varicella-zoster virus, Epstein-ban virus, cytomegalovirus, herpesvirus type 8, papillomavirus, BK virus, coronavirus, echovirus, John Cunningham (JC) virus, smallpox, Hepatitis B, bocavirus, parvovirus B19, astrovirus, Norwalk virus, coxsackievirus, Hepatitis A, poliovirus, rhinovirus, severe acute respiratory syndrome virus, Hepatitis C, yellow fever, dengue virus, West Nile virus, rubella, Hepatitis E, human immunodeficiency virus (HIV), human T-cell lymphotropic virus (HTLV), influenza, guanarito virus, Junin virus, Lassa virus, Machupo virus, Sabia virus, Crimean-Congo hemorrhagic fever virus, ebola virus, Marburg virus, measles virus, molluscum virus, mumps virus, parainfluenza, respiratory syncytial virus, human metapneumovirus, Hendra virus, Nipah virus, rabies, Hepatitis D, rotavirus orbivirus, coltivirus, vaccinia virus, and Banna virus.

In some embodiments, for example, fungal infection may be caused by at least one fungus selected from thrush, *Aspergillus* (*fumigatus, niger*, etc.), *Blastomyces dermatitidis, Candida* (*albicans, krusei, glabrata, tropicalis*, etc.), *Coccidioides immitis, Cryptococcus* (*neoformans*, etc.), *Histoplasma capsulatum, Mucorales* (*mucor, absidia, rhizophus*), *Paracoccidioides brasiliensis*, sporotrichosis, *Sporothrix schenkii*, zygomycosis, chromoblastomycosis, lobomycosis, mycetoma, onychomycosis, piedra pityriasis versicolor, tinea barbae, tinea capitis, tinea corporis, tinea cruris, tinea favosa, tinea nigra, tinea pedis, otomycosis, phaeohyphomycosis, and rhinosporidiosis.

In some embodiments, for example, parasitic infection may be caused by at least one parasite selected from *Acanthamoeba, Babesia microti, Balantidium coli, Entamoeba hystolytica, Giardia lamblia, Cryptosporidium muris, Trypanosomatida gambiense, Trypanosomatida rhodesiense, Trypanosoma brucei, Trypanosoma cruzi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Pneumocystis carinii, Trichomonas vaginalis, Histomonas meleagridis, Secementea, Trichuris trichiura, Ascaris lumbricoides, Enterobius vermicularis, Ancylostoma duodenale, Naegleria fowleri, Necator americanus, Nippostrongylus brasiliensis, Strongyloides stercoralis, Wuchereria bancrofti, Dracunculus medinensis*, blood flukes, liver flukes, intestinal flukes, lung flukes, *Schistosoma mansoni, Schistosoma haematobium, Schistosoma japonicum, Fasciola hepatica, Fasciola gigantica, Heterophyes heterophyes*, and *Paragonimus westermani*.

In certain embodiments, the present disclosure provides methods of treating or preventing cancer in a subject, comprising conjointly administering to the subject an inhibitor of the VISTA pathway and the TIM-3 pathway or by conjointly administering to the subject an inhibitor of the VISTA and PD-1 (e.g., PD-1, PD-L1 or PD-L2) pathways and an inhibitor of the TIM-3 and PD-1 (e.g., PD-1, PD-L1 or PD-L2) pathways.

In some embodiments, the cancer is breast cancer, colon cancer, lung cancer, melanoma, prostate cancer, and renal cancer.

In some embodiments, the cancer is blastoma, breast cancer, epithelial cancer, colon cancer, lung cancer, melanoma, prostate cancer, renal cancer, bone cancer, pancreatic cancer, skin cancer, cancer of the head or neck, uterine cancer, ovarian cancer, colorectal cancer, rectal cancer, cancer of the anal region, cancer of the peritoneum, stomach cancer, testicular cancer, carcinoma of the fallopian tubes, carcinoma of the endometrium, cervical cancer, vaginal cancer, vulval cancer, cancer of the esophagus, cancer of the small intestine, cancer of the endocrine system, cancer of the thyroid gland, cancer of the parathyroid gland, cancer of the adrenal gland, sarcoma, cancer of the urethra, cancer of the penis, chronic or acute leukemia, solid tumors of childhood, Hodgkin's lymphoma, non-Hodgkin's lymphoma, mesothelioma, thymic carcinoma, myeloma, cancer of the bladder, cancer of the ureter, carcinoma of the renal pelvis, liver cancer, pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, edema (such as that associated with brain tumors), Meigs' syndrome, Merkel cell carcinoma, and environmentally induced cancers.

In certain embodiments, the present disclosure provides methods of treating or preventing an infectious disease in a subject, comprising conjointly administering to the subject an inhibitor of the VISTA pathway and the TIM-3 pathway or by conjointly administering to the subject an inhibitor of the VISTA and PD-1 (e.g., PD-1, PD-L1 or PD-L2) pathways and an inhibitor of the TIM-3 and PD-1 (e.g., PD-1, PD-L1 or PD-L2) pathways.

In certain embodiments, the infectious disease is a bacterial infection, viral infection, fungal infection or parasitic infection.

In some embodiments, the infectious disease is anthrax, Bacilli, *Bordetella, Borrelia*, botulism, *Brucella, Burkholderia, Campylobacter, Chlamydia*, cholera, *Clostridium, Conococcus, Corynebacterium*, diptheria, *Enterobacter, Enterococcus, Erwinia, Escherichia, Francisella, Haemophilus, Heliobacter, Klebsiella, Legionella*, Leptospira, leptospirosis, *Listeria*, Lyme's disease, *Meningococcus, Mycobacterium, Mycoplasma, Neisseria, Pasteurella, Pelobacter*, plague, *Pneumonococcus, Proteus, Pseudomonas, Rickettsia, Salmonella, Serratia, Shigella, Staphylococcus, Streptococcus*, tetanus, *Treponema, Vibrio, Yersinia*, and *Xanthomonas*; at least one virus selected from arboviral encephalitis virus, adenovirus, herpes simplex type I, herpes simplex type 2, Varicella-zoster virus, Epstein-barr virus, cytomegalovirus, herpesvirus type 8, papillomavirus, BK virus, coronavirus, echovirus, John Cunningham (JC) virus, smallpox, Hepatitis B, bocavirus, parvovirus B19, astrovirus, Norwalk virus, coxsackievirus, Hepatitis A, poliovirus, rhinovirus, severe acute respiratory syndrome virus, Hepatitis C, yellow fever, dengue virus, West Nile virus, rubella, Hepatitis E, human immunodeficiency virus (HIV), human T-cell lymphotropic virus (HTLV), influenza, guanarito virus, Junin virus, Lassa virus, Machupo virus, Sabia virus, Crimean-Congo hemorrhagic fever virus, ebola virus, Marburg virus, measles virus, molluscum virus, mumps virus, parainfluenza, respiratory syncytial virus, human metapneumovirus, Hendra virus, Nipah virus, rabies, Hepatitis D, rotavirus orbivirus, coltivirus, vaccinia virus, and Banna virus; a fungal infection selected from thrush, *Aspergillus* (*fumigatus, niger*, etc.), *Blastomyces dermatitidis, Candida* (*albicans, krusei, glabrata, tropicalis*, etc.), *Coccidioides immitis, Cryptococcus* (*neoformans*, etc.), *Histoplasma capsulatum, Mucorales* (*mucor, absidia, rhizophus*), *Paracoccidioides brasiliensis*, sporotrichosis, *Sporothrix schenkii*, zygomycosis, chromoblastomycosis, lobomycosis, mycetoma, onychomycosis, piedra pityriasis versicolor, tinea barbae, tinea capitis, tinea corporis, tinea cruris, tinea favosa, tinea nigra, tinea pedis, otomycosis, phaeohyphomycosis, and rhinosporidiosis; and at least one parasite selected from *Acanthamoeba, Babesia microti, Balantidium coli, Entamoeba hystolytica, Giardia lamblia, Cryptosporidium muris, Trypanosomatida gambiense, Trypanosomatida rhodesiense, Trypanosoma brucei, Trypanosoma cruzi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Pneumocystis carinii, Trichomonas vaginalis, Histomonas meleagridis, Secementea, Trichuris trichiura, Ascaris lumbricoides, Enterobius vermicularis, Ancylostoma duodenale, Naegleria fowleri, Necator americanus, Nippostrongylus brasiliensis, Strongyloides stercoralis, Wuchereria bancrofti, Dracunculus medinensis*, blood flukes, liver flukes, intestinal flukes, lung flukes, *Schistosoma mansoni, Schistosoma haematobium, Schistosoma japonicum, Fasciola hepatica, Fasciola gigantica, Heterophyes heterophyes*, and *Paragonimus westermani*.

In some embodiments the inhibitor of the VISTA pathway and the TIM-3 pathway or the inhibitor of the VISTA and PD-1 (e.g., PD-1, PD-L1 or PD-L2) pathways and the inhibitor of the TIM-3 and PD-1 (e.g., PD-1, PD-L1 or PD-L2) pathways, are administered simultaneously. In some embodiments the one compound is administered within about 5 minutes to within about 168 hours prior to or after administration of the other compound.

Biomarker Screening

Gene expression profiles of a tissue of interest, such as a tumor tissue, can be obtained and therapeutic treatments can be selected based on the gene expression profile. In other words, if an anti-tumor agent acts by inhibiting a particular oncoprotein, it may be desirable to know whether a particular cancer expresses that oncogene before attempting to treat the cancer with the anti-tumor agent. The expression of a particular gene can be assessed in many ways. The level of gene transcript or the level of encoded protein may be determined. The presence of a protein may be determined directly, through methods such as antibody binding, mass spectroscopy and two-dimensional gel electrophoresis or indirectly, by detecting an activity of the protein, be it a biochemical activity or an effect on the levels of another protein or expression of one or more genes.

A number of methodologies are currently used for the measurement of gene expression. In some embodiments, these methodologies utilize the polymerase chain reaction (PCR) technique, the details of which are provided in U.S. Pat. Nos. 4,683,195, 4,683,202, and 4,965,188, all to Mullis et al., all of which are specifically incorporated herein by reference in its entirety. In some embodiments, methodologies utilize digital detection of a transcript by a probe hybridized to a segment of DNA that is attached to a unique string of colored fluorophones (also referred to as the molecular barcode).

Methodologies also include comparative genomic hybridization (CGH); fluorescence in situ hybridization (FISH); immunohistochemistry (IHC); and next-generation sequencing (NGS), and other molecular profiling techniques assessing DNA levels (e.g., genomic arrays), RNA quantification, proteomic assays, and the like.

As used herein, a "signature" is a pattern of expression of a defined subset of genes or biomarkers.

As used herein, a "highly immune signature positive" sample represents immune cell tumor infiltration by specific types of immune cells, such as cytotoxic T cells.

For example, in certain methods of treating cancer disclosed herein, the method may comprise determining whether a biological sample comprising tumor cells express (or overexpress, relative to normal tissue of that tissue type) a biomarker such as VISTA, TIM-3, PD-L1 or PD-L2. Similarly, the methods may comprise determining whether the biological sample is VISTA positive, TIM-3 positive, myeloid signature positive, natural killer signature positive, and/or highly immune signature positive. A patient's tumor may be biopsied to obtain a sample for testing, although the sample may be obtained in any other suitable way, such as by identifying shed or metastatic tumor cells or nucleic acid in the subject's bloodstream. In some embodiments, the sample may be tested in situ in the patient. Alternatively, the sample may be a blood sample, and determining whether the tumor overexpresses a marker may comprises measuring the level of the marker in the blood sample to determine whether the level is indicative of normal expression of the marker or of elevated expression of the marker. Alternatively, the sample may be a blood sample, and determining whether the tumor expresses a immune signature, may comprise measuring the level of an immune signature in the blood sample to determine whether the level is indicative of normal expression of the signature or of elevated expression of the signature.

In some embodiments, a biological sample may exhibit elevated expression of VISTA, TIM-3 or other markers of activation of the immune system. For example, a biological sample may exhibit a certain signature, e.g., be highly immune signature positive. In some embodiments, a patient who exhibits a particular gene signature may then be treated with conjoint administration of a compound of Formula (I) and a compound of Formula (II).

In some embodiments, a patient who exhibits elevated expression of VISTA, TIM-3, PD-L1, and/or PD-L2, may then be treated with a compound as disclosed herein.

Accordingly, provided herein are methods of modulating an immune response in a subject, comprising
a) determining whether a biological sample from a subject overexpresses VISTA, TIM-3, PD-L1, and/or PD-L2; and
b) contacting the subject with a compound of Formula (I) and a compound of Formula (II) as disclosed herein if the sample overexpresses VISTA, TIM-3, PD-L1, and/or PD-L2.

In some embodiments, provided herein are methods of modulating an immune response in a subject, comprising
a) determining whether a biological sample from a subject overexpresses VISTA and TIM-3; and
b) contacting the subject with a compound of Formula (I) and a compound of Formula (II) as disclosed herein if the sample overexpresses VISTA and TIM-3.

In some embodiments, the method further comprises determining whether the sample also overexpresses PD-L1 or PD-L2. In some embodiments, the methods disclosed herein further comprise determining whether the sample also overexpresses a marker of activation of the immune system. In alternative embodiments, the methods disclosed herein comprise determining whether the sample overexpresses genes that are co-expressed with TIM-3 or VISTA. In certain embodiments, the sample comprises one or more tumor cells.

Another application of assessing gene expression is in the development of companion diagnostic (CDx) tools for determining whether a drug or other therapeutic agent will be beneficial to the subject having a disease or condition modulated by that gene's activity. A CDx can guide the use of a drug to only patients having the gene, gene signature or protein affected by the therapy and can be a required element in an FDA approved therapy. Subjects benefit from not being prescribed drugs that will not have a beneficial effect for a disease, e.g. a certain cancer, and allow the physician to tailor therapy on a patient by patient basis. Thus, it is paramount that the CDx be analytically and clinically validated to minimize any false positive or negative effects. For this reason, CDx tests are often developed in parallel with the drug development. An effective CDx must have a high and reproducible correlation with the disease or condition being assessed.

In certain embodiments, provided herein is a method of identifying the likelihood of modulating an immune response in a subject with a compound of Formula (I) and a compound of Formula (II), the method comprising:
a) obtaining or providing a biological sample from a subject;
b) measuring the amount or activity of VISTA and TIM-3 in the subject sample; and
c) comparing the measured amount or activity to an amount or activity of the VISTA and TIM-3 in a control sample,
wherein a significantly increased amount or activity of VISTA and TIM-3 in the subject sample relative to the control sample identifies the subject as being more likely to be responsive to the conjoint administration of a compound of Formula (I) and a compound of Formula (II), and
wherein a similar or decreased amount or activity of VISTA and TIM-3 in the subject sample relative to the control sample identifies the subject as being less likely to be responsive to the conjoint administration of a compound of Formula (I) and a compound of Formula (II).

In some embodiments, provided herein is a method of identifying the likelihood of modulating an immune response in a subject with a conjoint administration of a compound Formula (I) and a compound of Formula (II), the method comprising:
a) obtaining or providing a biological sample from a subject;
b) measuring the amount or activity of VISTA and TIM-3 in the subject sample; and
c) comparing the measured amount or activity to an amount or activity of the VISTA and TIM-3 in a control sample,
wherein a similar or decreased activity of VISTA and TIM-3 in the subject sample relative to the control sample identifies the subject as being more likely to the conjoint administration of a compound of Formula (I) and a compound of Formula (II), and
wherein a high amount or activity of VISTA and TIM-3 in the subject sample relative to the control sample identifies the subject as being less likely to be responsive to the conjoint administration of a compound of Formula (I) and a compound of Formula (II).

In certain embodiments, the biological sample is selected from serum, whole blood, plasma, urine, cells (e.g., tumor cells), cell lines, surgically recessed tumor tissue, and tissue biopsies. In some embodiments, the sample is selected from whole blood or a tissue biopsy. In certain embodiments, the sample comprises biomarkers, e.g., VISTA, TIM-3, PD-L1, and/or PD-L2, from the subject. In some embodiments, the subject exhibits a particular gene signature as the biomarker. In some embodiments, the gene signature includes VISTA and/or TIM-3 expression. In some embodiments, the subject has cancer as described herein. In some embodiments, the method further comprises recommending, conjointly prescribing or conjointly administering a compound of Formula (I) and a compound of Formula (II) if the subject is determined likely to be responsive to the conjoint administration of a compound of Formula (I) and a compound of Formula (II) or administering a therapy other than a compound of Formula (I) and a compound of Formula (II) if the subject is determined be less likely to be responsive to a compound of Formula (I) and a compound of Formula (II).

In certain embodiments, the control sample is a sample from either the subject or a member of the same species to which the patient belongs or even a healthy tissue sample obtained from the same subject. The control sample may comprise cells or not comprise cells. The control sample may comprise cancer cells known to be responsive or non-responsive to a compound of Formula (I) and a compound of Formula (II).

In certain embodiments, the amount of VISTA and/or TIM-3 is detected using a reagent which specifically binds with the protein. In certain embodiments, the reagent is selected from an antibody, an antibody derivative, and an antibody fragment. In certain embodiments, VISTA and/or TIM-3 expression is assessed by detecting the presence in the sample of a transcribed polynucleotide or portion thereof. In certain embodiments, the transcribed polynucleotide is an mRNA or a cDNA. In certain embodiments, detecting further comprises amplifying the transcribed polynucleotide. In certain embodiments, the transcribed polynucleotide is detected by identifying a nucleic acid that anneals with the biomarker nucleic acid or a portion thereof, under stringent hybridization conditions. In some embodiments, the detection of a gene signature as a biomarker may be based on methods including, but not limited to, next-generation sequencing (NGS), hybridization, and digital detection. For example, multiplex sequencing is an NGS method that uses parallel sequencing and unique index tags allowing pooled samples to be analyzed simultaneously. Digital detection relies on discrete units for measurement rather than relying on relative levels of signals. For example, a transcript is detected by a probe hybridized to a segment of DNA that is attached to a unique string of colored fluorophores (molecular barcode), and the total number of transcripts in the sample is quantified by counting the number of times a particular molecular barcode is detected.

The expression of VISTA and/or TIM-3 in a subject is "significantly" higher or lower than the normal amount of the biomarker, if the amount of VISTA and/or TIM-3 is greater or less, respectively, than the normal level by an amount greater than the standard error of the assay employed to assess amount, and preferably at least about 0.2×, 0.3×, 0.4×, 0.5×, 0.6×, 0.7×, 0.8×, 0.9×, 1×, 1.5×, 2×, 2.5×, 3×, 3.5×, 4×, 5×, 6×, 7×, 8×, 9× or 10× than that amount. Alternatively, the amount of VISTA and/or TIM-3 in the subject can be considered "significantly" higher or lower than the normal amount if the amount is at least about two, and preferably at least about three, four or five times, higher or lower, respectively, than the normal amount of VISTA and/or TIM-3. Such "significance" can also be applied to any measured parameter described herein, such as for expression, inhibition, cytotoxicity, cell growth, and the like.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody.

The term "control" refers to any reference standard suitable to provide a comparison to the expression products in the test sample. In certain embodiments, the control comprises obtaining a "control sample" from which expression product levels are detected and compared to the expression product levels from the test sample. Such a control sample may comprise any suitable sample, including but not limited to a sample from a control subject (can be stored sample or previous sample measurement) with a known outcome; normal tissue or cells isolated from a subject, cultured primary cells/tissues isolated from a subject, adjacent normal cells/tissues obtained from the same organ or body location of the subject, a tissue or cell sample isolated from a normal subject or a primary cells/tissues obtained from a depository. In certain embodiments, the control may comprise a reference standard expression product level from any suitable source, including but not limited to housekeeping genes, an expression product level range from normal tissue (or other previously analyzed control sample), a previously determined expression product level range within a test sample from a group of patients or a set of patients with a certain outcome or receiving a certain treatment. It will be understood by those of skill in the art that such control samples and reference standard expression product levels can be used in combination as controls in the methods of the present invention.

The "normal" level of expression of VISTA and/or TIM-3 is the level of expression of VISTA and/or TIM-3 in cells of a subject, e.g., a human patient, not in need of immune response modulation. An "over-expression" or "significantly higher level of expression" of a biomarker refers to an expression level in a test sample that is greater than the standard error of the assay employed to assess expression, and is preferably at least about 10%, and more preferably about 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of VISTA and/or TIM-3 in a control sample (e.g., sample from a healthy subject not in need of immune modulation or from a healthy tissue sample obtained from the same subject) and preferably, the average expression level of the biomarker in several control samples. A "significantly lower level of expression" of a biomarker refers to an expression level in a test sample that is at least about 10%, and more preferably about 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not in need of immune modulation) and preferably, the average expression level of the biomarker in several control samples.

The term "sample" used for detecting or determining the presence or level of the VISTA and/or TIM-3 gene is typically whole blood, plasma, serum, saliva, urine, stool (e.g., feces), tears, and any other bodily fluid (e.g., as described above under the definition of "body fluids") or a tissue sample (e.g., biopsy) such as a small intestine, colon sample, a tumor sample or surgical resection tissue. In some embodiments, the disclosed methods further comprise obtaining the sample from the subject prior to detecting or determining the presence or level of the VISTA and/or TIM-3 gene.

Methods of Administration

The compounds of the present disclosure may be formulated for administration separately or together. The compounds may be formulated, individually or together, in a pharmaceutical composition in which the compound is mixed with one or more pharmaceutically acceptable materials.

The pharmaceutical composition may be administered by oral or inhalation routes or by parenteral administration route. For example, compositions can be administered orally, by intravenous infusion, topically, intraperitoneally, intravesically, intrathecally or as a suppository. Examples of parenteral administration includes but not limited to intraarticular (in the joints), intravenous, intramuscular, intradermal, intraperitoneal, and subcutaneous routes. Suitable liquid compositions may be aqueous or non-aqueous, isotonic sterile injection solutions, and may contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Oral administration, parenteral administration, subcutaneous administration and intravenous administration are preferred methods of administration.

The dosage of the compounds of the present disclosure varies depending on a patient's age, weight or symptoms, as well as the compound's potency or therapeutic efficacy, the dosing regimen and/or treatment time. Generally, suitable routes of administration may, for example, include oral, eyedrop, rectal, transmucosal, topical or intestinal administration; parenteral delivery, including intramuscular, subcutaneous, intramedullary injections, as well as intrathecal, direct intraventricular, intravenous, intraperitoneal, intranasal or intraocular injections. The compounds of the disclosure may be administered in an amount of 0.5 mg or 1 mg up to 500 mg, 1 g or 2 g per dosage regimen. The dosage may be administered once per week, once per three days, once per two days, once per day, twice per day, three times per day or more often. In alternative embodiments, in certain adults the compound can be continuously administered by intravenous administration for a period of time designated by a physician. Since the dosage is affected by various conditions, an amount less than or greater than the dosage ranges contemplated about may be implemented in certain cases. A physician can readily determine the appropriate dosage for a patient undergoing therapeutic treatment.

Combination Therapy

Two therapeutic compounds, such as a compound of Formula (I) and a compound of Formula (II), may be administered in combination (1) to complement and/or enhance effects of the two compounds administered separately, (2) to modulate pharmacodynamics, improve absorption or reduce dosage of the two compounds, and/or (3) to reduce or ameliorate the side effects of the two compounds. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 8 hours, 12 hours, 24 hours, 36 hours, 48 hours, 72 hours or a week of one another. Thus, an individual who receives such treatment can benefit from a combined effect of different therapeutic compounds. The respective compounds may be administered by the same or different route and the same or different method. In some embodiments, the combined effect of conjoint therapy is detectable through immune effects.

The dosage of the other drug can be a dosage that has been clinically used or may be an altered dosage such that the dosage is effective when administered in combination with a compound of the present disclosure. The ratio of the compound of the present disclosure and the other drug can vary according to age and weight of a subject to be administered, administration method, administration time, disorder to be treated, symptom and combination thereof. For example, the other drug may be used in an amount of 0.01 to 100 parts by mass, based on 1 part by mass of the compound of the present disclosure.

Conjoint therapy can be employed to treat any diseases discussed herein. In certain embodiments, a compound of Formula (I) and a compound of Formula (II) may be conjointly administered with yet another therapeutic agent, e.g., an anti-cancer agent, an anti-viral agent, a cytokine or an immune agonist. In some embodiments, the other therapeutic agent is selected from CTLA-4 antagonists, PD-1 antagonists, PD-L1 antagonists or PD-L2 antagonists, and EGFR antagonists.

Agents for Combination Therapies

In certain embodiments, a combination of agents that inhibit the VISTA and TIM-3 pathways or the VISTA, TIM-3, and PD-1 (e.g., PD-1, PD-L1 or PD-L2) pathways, such as a compound of Formula (I) and a compound of Formula (II), can be conjointly administered with yet another therapeutic agent, e.g., 1) an aldosterone synthase inhibitor;
2) an ALK inhibitor; an apoptosis inducer;
3) an aromatase inhibitor;
4) a CART cell (e.g., a CART cell targeting CD19);
5) a BCR-ABL inhibitor;
6) a BRAF inhibitor;
7) a CDK4/6-inhibitor;
8) a CEACAM (e.g., CEACAM-1, -3 and/or -5) inhibitor;
9) a c-KIT inhibitor;
10) a c-MET inhibitor;
10) a cRAP inhibitor;
11) a CTLA4 inhibitor;
12) a cytochrome P450 inhibitor (e.g., a CYP17 inhibitor);
13) an EGF inhibitor;
14) an ERK1/2 ATP inhibitor;
15) an FGF inhibitor (e.g., a FGFR2 or FGFR4 inhibitor);
16) a Flt3 inhibitor (e.g., FLK2/STK1);
17) a P-Glycoprotein 1 inhibitor;
18) a HDAC inhibitor;
19) a HDM2 inhibitor;
20) a HER3 inhibitor;
21) a histamine release inhibitor;
22) an HSP90 inhibitor:
23) an IAP inhibitor;
24) an IDH inhibitor;
25) an IDO inhibitor
26) an IGF-1R inhibitor;
27) an iron chelating agent;
28, a Janus inhibitor;
29) a LAG-3 inhibitor;
30) an M-CSF inhibitor;
31) a MEK inhibitor;
32) an mTOR inhibitor;
33) a p53 inhibitor (e.g., an inhibitor of a p53/Mdm2 interaction);
34) a PDGFRβ inhibitor;
35) a PKC inhibitor;
36) a PI3K inhibitor;
37) a PIM inhibitor;
38) a PRLR inhibitor;
39) a Raf kinase C inhibitor;
40) a smoothened (SMO) receptor inhibitor;
41) a somatostatin agonist and/or a growth hormone release inhibitor;
42) a transduction modulator and/or angiogenesis inhibitor;
43) a VEGFR-2 inhibitor (e.g., FLK-1/KDR);
44) a tyrosine kinase inhibitor (e.g., CSF-1R tyrosine kinase);
45) a Wnt signaling inhibitor
46) a Bcl-2 inhibitor;
47) a Mcl-1 inhibitor;
48) a BTK inhibitor;
49) dual active molecules such as CUDC-907 (a dual PI3K/HDAC inhibitor);
50) BET bromodomain inhibitor; and
51) an arginase inhibitor;
52) LXR agonist;

53) ROR gamma agonist;
54) CHK1/2 inhibitor;
55) Cbl-b inhibitor;
56) Csk inhibitor; and
57) c-Rel inhibitor including pentoxifylline;

Additional therapeutic agents suitable for conjoint administration with the compounds and compositions disclosed herein have been described, for example, in the following publications: WO2016/100882; WO2016/054555; WO2016/040892; WO2015/097536; WO2015/088847; WO2015/069770; WO2015/026634; WO 2015/009856; EP 1377609 B1; Antonia, et al. Clin. Cancer Res. 2014 20:6258-6268; and Melero, et al. Nature Reviews Cancer 2015 15:457-472. Each publication is incorporated herein by reference in its entirety.

For example, in the methods of the disclosure directed to the treatment of cancer, the compound of the present disclosure can be used with another chemotherapeutic conjointly as a single pharmaceutical composition or a combination of different pharmaceutical compositions. Non-limiting examples of the chemotherapeutic agent include an alkylation agent, nitrosourea agent, antimetabolites, anticancer antibiotics, vegetable-origin alkaloids, topoisomerase inhibitors, hormone drugs, hormone antagonists, leucopenia (neutropenia) treatment drugs, thrombocytopenia treatment drugs, antiemetics, aromatase inhibitors, P-glycoprotein inhibitors, platinum complex derivatives, other immunotherapeutic drugs and other anticancer drugs.

Exemplary cytotoxic agents that can be administered conjointly include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation).

Non-limiting examples of additional therapeutic agents include, but are not limited to, peptides, polypeptides, proteins, fusion proteins, nucleic acid molecules, small molecules, mimetic agents, synthetic drugs, inorganic molecules, and organic molecules.

The pharmaceutical composition can contain or the conjoint therapy can include, other compatible agents, e.g., a chemotherapeutic agent, a DNA-alkylating agent, an auristatin, a cytokine therapy, an interferon therapy (e.g., interferon-α, β or γ; interferon α-2a; interferon α-2b; interferon α-m; interferon α-n3; interferon β-Ia; and interferon γ-Ib), an interlukin therapy (e.g., IL-1, IL-2, IL-2Rβ, IL-2Rγ, IL-3, IL-7, IL7Rα, IL-11, IL-12, IL-15, and IL-21), a cluster of differentiation (CD) protein (e.g., CD2, CD4, CD7, CD8a, CD11a/CD18, CD11b, CD11c, CD11d, CD18, CD19, CD19a, CD20, CD27, CD28, CD29, CD30, CD40, CD40L, CD49a, CD49D, CD49f, CD69, CD84, CD96, CD100, CD103, CD137, CD160, CD226, CD229, CD278) a co-stimulatory modulator, e.g., an agonist (e.g., an agonistic antibody or antigen-binding fragment thereof or soluble fusion) of an MHC class I molecule, a TNF receptor protein, an immunoglobulin-like protein, a Toll ligand receptor, a CD83 ligand, a cytokine receptor, an integrin, signaling lymphocytic activation molecules (SLAM proteins), an activating NK cell receptor such as NKGD2, an antibody therapy, a viral therapy, gene therapy or a combination thereof.

Chemotherapeutic and other therapeutic agents that may be conjointly administered with compounds of the disclosure include, but are not limited to: abiraterone, abraxane, aceglatone, acivicin, aclacinomysin, actimid, actinomycin, aflibercept, aldesleukin, aldophosphamide glycoside alectinib, alendronate, alitretinoin, altretamine, aminoglutethimide, aminolevulinic acid, aminopterin, amsacrine, anastrozole, ancitabine, angiostatin, angiozyme, anguidine, ansamitocin, anthramycin, antithrombin III, apatinib, arabinoside, arboplatin, asparaginase, authramycin, axitinib, azacitidine, azaserine, azetepa, azotomycin, 6-azauridine, baricitinib, batimastat, bendamustine, benimetinib, benzodopa, bestrabucil, bexarotene, bicalutamide, bisantrene, bleomycin, bortezomib, bosutinib, brequinar, brivanib, bryostatin, bropirimine, bullatacin, bullatacinone, buserelin, busulfan, cactinomycin, calicheamicin, callystatin, calusterone, caminomycin, campothecin, capecitabine, carabicin, carboplatin, carboquone, carfilzomib, carmofur, carmustine, carubicin, carzelesin, carzinophilin, cedefingol, cediranib, chlomaphazine, chlorambucil, chloroquine, chlorozotocin, cholophosphamide, chromomycin, cirolemycin, cisplatin, cisdichlorodiamine platinum (II), cisplatin, cladribine, clodronate, cobimetinib, colchicine, crisnatol, crizotinib, cryptophycin 1, cryptophycin 8, cyclophosphamide, cyproterone, cytarabine, cytochalasin B, cytosine arabinoside, dabrafenib, dacarbazine, dactinomycin, danoprevir, dasatinib, diaziquone, dibromomannitol, daunorubicin, decitabine, defofamine, degarelix, 1-dehydrotestosterone, delanzomib, demecolcine, demethoxyviridin, denileukin, denenicokin, denopterin, desacetylravidomycin, detorubicin, dexamethasone, dexormaplatin, dezaguanine, diaziquone, 6-diazo-5-oxo-L-norleucine, dichloroacetate, dideoxyuridine, dienestrol, diethylstilbestrol, diftitox, difluoromethylomithine, dihydroxyanthracindione, dinaciclib, docetaxel, dolastatin, dovitinib, doxifluridine, doxorubicin, doxycycline, droloxifene, dromostanolone, duazomycin, duocarmycin, dynemicin, edatrexate, eflomithine, elliptinium acetate, eleutherobin, emetine, emsirolimus, encorafenib, enloplatin, enocitabine, enpromate, epipropidine, epirubicin, epithilone, epitiostanol, erbulozole, erismodegib, erlotinib, esorubicin, esperamicin, estradiol, estramustine, etanidazole, ethidium bromide, 2-ethylhydrazide, etidronate, etoglucid, etoposide, everolimus, exemestane, fadrozole, fazarabine, fenretinide, filgrastim, floxuridine, fludarabine, fludrocortisone, fluorouracil, fluoxymesterone, flurocitabine, flutamide, foretinib, formestane, fosquidone, fotemustine, frolinic acid, gacytosine, gallium nitrate, galunisertib, gandotinib, gefitinib, geldanamycin, gemcitabine, genistein, glucocorticoids, goserelin, gramicidin D, herbimycin, hiltonol, 4-hydroxytamoxifen, hydroxyurea, ibandronate, idarubicin, ifosfamide, ilmofosine, imatinib, imiquimod, improsulfan, indoximod, interferon, iproplatin, irinotecan, ironotecan, ixazomib, keoxifene, laherparepvec, lameotide, lapatinib, lenalidomide, lestaurtinib, letrozole, leucovorin, leuprolide, lentinan, levamisole, liarozole, lidocaine, linifanib, lometrexo, lomustine, lonidamine, losoxantrone, marcellomycin, marizomib, masitinib, masoprocol, maytansyne, maytansinol, mechlorethamine, mechlorethamine oxide hydrochloride, mannomustine, medroxyprogesterone, megestrol, melengestrol, menogaril, melphalan, mepitiostane, mercaptopurine, mesna, metformin, methotrexate, metoprine, meturedopa, mithramycin, mitobronitol, mitoguazone, mitolactol, mitomycin, mitosper, mitotane, mitoxantrone, momelotinib, montanide, monomethyl auristatin E, mopidamol, motesanib, motolimod, mycophenolic acid, mylotarg, nab-paclitaxel, navelbine, neratinib, nilotinib, nilutamide, nimustine, nitracrine, nocodazole, nogalamycin, novantrone, novembichin, obinutuzumab, octreotide, olivomycin, onapristone ormaplatin, oxaliplatin, paclitaxel, pacritinib, palbociclib, pamidronate, pancratistatin, panobinostat, pazopanib, pegaptanib, pegaspargase, pegfilgrastim, peginterferon α-2b, pelitinib, pemetrexed, pentostatin, N4-pentoxycarbonyl-5-deoxy-5-fluorocytidine, peplomycin, perifosine, phenamet, phenesterine, pimasertib, pipobroman, piposulfan, pirarubicin, plicamycin, podophyllinic acid, polifeprosan, pomalidomide, porfimer, porfiromycin, potfiromycin, prednimustine, procaine, procarbazine, propranolol, pteropterin, puromycin, quelamycin, raltitrexed, raloxifene, ranimustine, rapamycin, ravidomycin, razoxane, regorafenib, risedronate, resiquimod, rituximab, rodorubicin, rogletimide, roridin, ruxolitinib, safingol, sarcodictyin, selumetinib, semaxanib, semustine, simapimod, simtrazene, sirolimus, sizofiran, sorafenib, sparfosate, sparsomycin, spirogermanium, spiromustine, spiroplatin, spongistatin, streptonigrin, streptozocin, sulofenur, sunitinib, suramin, talisomycin, tamoxifen, talimogene, tasocitinib, taxol, tegafur, telatinib, teloxantrone, temoporfin, temozolomide, temsirolimus, teniposide, tenuazonic acid, teroxirone, testolactone, testosterone, tetracaine, tezacitibine, thalidomide, thiamiprine, thioguanine, thiotepa, tiazofurin, tiludronate, tirapazamine, titanocene, tivozanib, toceranib, tofacitinib, topoisomerase inhibitor RFS 2000, topotecan, toremifene, tozasertib, trametinib, trastuzumab, triaziquone, tretinoin, 2,2',2"-trichlorotriethylamine, triethylenemelamine, triethylenephosphoramide, triethylenethiophosphaoramide, trilostane, trimethylolomelamine, trimetrexate, triptorelin, trofosfamide, tubercidin, tuvizanib, uracil mustard, ubenimex, uredopa, urethane, vandetanib, vapreotide, vargatef, vatalanib, vemurafenib, verrucurin, verteporfin, vinblastine, vincristine, vindesine, vinepidine, vinglycinate, vinleurosine, vinorelbine, vinrosidine, vinzolidine, vorozole, vismodegib, xeloda, zactima, zeniplatin, zinostatin, Ziv-aflibercept, zoledronate, and zorubicin.

In certain embodiments, exemplary chemotherapeutic agents include, but are not limited to, cytokines such as ABT-869, ACP-196, ADXS11-001, ADXS31-142, AEE788, AG-490, AM0010, AMN-107, AMP-224, AMP-514, AP24534, ARRY-142886, AST-6, AZD1480, AZD4547, AZD6094, AZD6244, AZD8055, AZD9291, B7-H3, BAFFR, 4-1BB, BEZ235, BGT 226, BHG712, BIBF 1120, BIBW2992, BIX 02188, BJG398, BKM-120, BMS-599626, BMS-690154, BMS-777607, BMS-911543, BMS-936558, BMS-936559, BMS-986016, BRAF-V600E, BTLA, BUW078, BYL719, CAL-101, CAL-263, CBI-TMI, CC-1065, CC-4047, CC-5013, CDS, CDX-1127, CEACAM1, CEP-701, CEP-11981, CGM097, Chi Lob 7/4, CI-1040, CO-1686, CP-673451, CP-870,893, CpG 7909, CPT-11, CRTAM, CT-011, CTL019, CTLA-4, CUDC-101, CYC116, CYT 387, DCC-2036, DNAM1, E6201, E7080, EGF816, FOLFOX6, G02443714, G-38963, GADS, GC1008, G-CSF, GDC-0032, GDC-0973, GDC-0980, GITR, GM-CSF, GR-MD-02, GSK1059615, GVAX, HVEM (LIGHTR), IA4, ICAM-1, ICOS, IMC-TR1, IMP321, INC280, INC424, INCB18424, INCB024360, INCB028050, IPH2012, IPI926, IRX-2, ISA 51VG, ITGA4, ITGA6, ITGAD, ITGAE, ITGAL, ITGAM, ITGAX, ITGB1, ITGB2, ITGB7, JNJ-26483327, Ki8751, KIRDS2, KU-0063794, KW-289LAT, LBH589, LCL161, LGH447, LTBR, LDK378, LEE011, LGX818, LIGHT, LJM716, LY117018, LY2157299, LY294002, LY2940680, M-CSF, MARTI, MDX-1105, MDX-1106, MEDI0562, MEDI4736, MEDI4737, MEDI6383, MEDI6469, MEK162, MG-132, MGCD265, MK-3475, MK-4166, MM-121, MOXR0916, MP470, MPDL3280A, MSB-0010718C, NKG2C, NKG2D, NKp30, NKp44, NKp46, NKp80 (KLRF1), NY-ESO-1, ODC-0879, ODC-0980, ONX-0912, ODC-0941, OSI-027, OSI-930, OSK-1120212, OSK 2118436, OSK 2126458, OX40, P529, PAG/Cbp, PD153035, PD173074, PD0325901, PF-299804, PF-02341066, PF-04217903, PF-046915032, PF-05082566, PD98059, Poly(I:C), PKI-587, PLX4032, PLX4720, PSGL1, PSK, PX-886, Rad-001, RAF265, rHIgM12B7, R07204, R04987655, R06895882, R07009789, SAR 245408, SAR 245409, SB-1317, SB-1518, SB-1578, SELPLG, SF1126, SGX523, SLAM, SLAMF4, SLAMF6, SLAMF7, SLAML_BLAME, SLP-76, SU 5402, T2 toxin, TEW 7197, TGN1412, TNFR2, TRANCE/RANKL, TriMix-DC, TRP-2, TRX518, TSU-68, VLA1, VLA-6, WYE-354, WZ3146, WZ4002, WZ8040, XL-147, XL-184, XL-228, XL-281, XL-647, XL-756, XL-765, XL-880, Yttrium90/MX-DTPA, and YW243.55.570.

Exemplary paclitaxel agents that can be used conjointly with compounds disclosed herein include, but are not limited to, nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG 105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'paclitaxel methyl 2-glucopyranosyl succinate, see Liu et al., Bioorganic & Medicinal Chemistry Letters (2007) 17:617-620).

In certain embodiments, exemplary chemotherapeutic agents include, but are not limited to:
1) (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide;
2) ((1R,9S,12S,15R,16E,18R,19R,21R,23S,24E,26E,28E, 30S,32S,35R)-1,18-dihydroxy-12-{(1R)-2-[(1S,3R,4R)-4-(2-hydroxyethoxy)-3-methoxycyclohexyl]-1-methylethyl}-19,30-dimethoxy-15,17,21,23,29,35-hexamethyl-11,36-dioxa-4-azatricyclo[30.3.1.04,9]hexatriaconta-16, 24,26,28-tetraene-2,3,10,14,20-pentaone);
3) (S)-1-(4-chlorophenyl)-7-isopropoxy-6-methoxy-2-(4-{methyl-[4-(4-methyl-3-oxopiperazin-1-yl)-trans-cyclohexylmethyl]-amino}phenyl)-1,4-dihydro-2H-isoquinolin-3one;
4) N-(4-((1R,3S,5S)-3-amino-5-methylcyclohexyl)pyridin-3-yl)-6-(2,6-difluorophenyl)-5-fluoropicolinamide;
5) anti-HER3 monoclonal antibody or antigen binding fragment thereof, that comprises a VH of SEQ ID NO: 141 and VL of SEQ ID NO: 140, as described in U.S. Pat. No. 8,735,551;
6) (E)-N-hydroxy-3-(4-(((2-(2-methyl-1H-indol-3-yl)ethyl) amino)methyl)phenyl) acrylamide;
7) (3R)-3-cyclopentyl-3-[4-(7H-pyrrolo-[2,3-d]pyrimidin-4-yl)-1H-pyrazol-1-yl]propanenitrile; and/or
8) 8-(2,6-difluoro-3,5-dimethoxy-phenyl)-quinoxaline-5-carboxylic acid (4-dimethylaminomethyl-1H-imidazol-2-yl)-amide.

In some embodiments, exemplary chemotherapeutic agents include, but are not limited to,
1) 3-(1H-indol-3-yl)-4-[2-(4-methyl-1-piperazinyl)-4-quinazolinyl]-1H-pyrrole-2,5-diane;
2) 5-(2,4-dihydroxy-5-isopropylphenyl)-N-ethyl-4-(4-(morpholinomethyl)phenyl)isoxazole-3-carboxamide;
3) 2-methyl-2-(4-(3-methyl-2-oxo-8-(quinolin-3-yl)-2,3-dihydro-1H-imidazo[4,5-c]quinolin-1-yl)phenyl)propanenitrile (dactolisib);
4) Compound D (CYP17 inhibitor);
5) 4-[3,5-bis(2-hydroxyphenyl)-1H-1,2,4-triazol-1-yl]-benzoic acid (defeasirox);

6) 4,4'-(1H-1,2,4-triazol-1-ylmethylene)bis-benzonitrile (letrozole);
7) (4S,5R)-3-(2'-amino-2-morpholino-4'-(trifluoromethyl)-[4,5'-bipyrimidin]-6-yl)-4-(hydroxymethyl)-5-methyl-oxazolidin-2-one;
8) (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one;
9) 4-[(4-methyl-1-piperazinyl)methyl]-N-[4-methyl-3-[[4-(3-pyridinyl)-2-pyrimidinyl]amino]phenyl]-methane-sulfonate-benzamide;
10) 4-[(R)-6,7-dihydro-5H-pyrrolo[1,2-c]imidazol-5-yl]-3-fluorobenzonitrile (osilodrostat);
11) N-[6-[(2R,6S)-2,6-dimethyl-4-morpholinyl]-3-pyridinyl]-2-methyl-4'(trifluoromethoxy)-[1,1'-biphenyl]-3-carboxamide, diphosphate (sonidegib phosphate);
12) (R)-2-(5-(4-(6-benzyl-4,5-dimethylpyridazin-3-yl)-2-methylpiperazin-1-yl) pyrazin-2-yl)propan-2-ol;
13) Compound M (human monoclonal antibody to PRLR);
14) 2-(2',3-dimethyl-[2,4'-bipyridin]-5-yl)-N-(5-(pyrazin-2-yl)pyridin-2-yl) acetamide;
15) 7-cyclopentyl-N,N-dimethyl-2-((5-((1R,6S)-9-methyl-4-oxo-3,9-diaza bicyclo[4.2.1]nonan-3-yl)pyridin-2-yl)amino)-7H-pyrrolo[2,3-d]pyrimidine-6-carboxamide;
16) Compound P (FGFR2 and/or FGFR4 antibody drug conjugate, mAb 12425);
17) Compound Q (monoclonal antibody of Fab to M-CSF);
18) N-[(9S,10R,11R,13R)-2,3,10,11,12,13-hexahydro-10-methoxy-9-methyl-1-oxo-9,13-epoxy-1H,9H-diindolo[1,2,3m]pyrrolo[3,4-j][1,7]benzodiazonin-11-yl]-N-methyl-benzamide (midostaurin);
19) 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine;
20) cyclo((4R)-4-(2-aminoethylcarbamoyloxy)-L-prolyl-L-phenylglycyl-D-tryptophyl-L-lysyl-4-O-benzyl-L-tyrosyl-L-phenylalanyl-) (pasireotide diaspartate);
21) 1-amino-5-fluoro-3-[6-(4-methyl-1-piperazinyl)-1H-benzimidazol-2-yl]-2 (1H)-quinolinone (dovitinib);
22) 8-(6-methoxy-pyridin-3-yl)-3-methyl-1-(4-piperazin-1-yl-3-trifluoromethyl-phenyl)-1,3-dihydro-imidazo[4,5-c]quinolin-2-one;
23) N6-(2-isopropoxy-5-methyl-4-(1-methylpiperidin-4-yl)phenyl)-N4-(2-(isopropylsulfonyl)phenyl)-1H-pyrazolo[3,4-d]pyrimidine-4,6-diamine;
24) 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide;
25) 5-chloro-N2-(2-fluoro-5-methyl-4-(1-(tetrahydro-2H-pyran-4-yl)piperidin-4-yl)phenyl)-N4-(5-methyl-1H-pyrazol-3-yl)pyrimidine-2,4-diamine;
26) 5-chloro-N2-(4-(1-ethylpiperidin-4-yl)-2-fluoro-5-methylphenyl)-N4-(5-methyl-1Hpyrazol-3-yl)pyrimidine-2,4-diamine;
27) 6-[(2S,4R,6E)-4-methyl-2-(methylamino)-3-oxo-6-octenoic acid]cyclosporine D. Amdray, PSC833, [3'-Desoxy-3'-oxo-MeBmt]1-[Val]2-cyclosporin (valspodar);
28) N-(4-chlorophenyl)-4-(4-pyridinylmethyl)-1-phthalazinamine succinate (vatalanib succinate);
29) Compound CC (IDH inhibitor);
30) (R)—N-(4-(chlorodifluoromethoxy)phenyl)-6-(3-hydroxypyrrolidin-1-yl)-5-(1H-pyrazol-5-yl)nicotinamide;
31) Compound EE (cRAF inhibitor);
32) Compound FF (ERK1/2 ATP competitive inhibitor); and
33) 4-((2-(((1R,2R)-2-hydroxycyclohexyl)amino)benzo[d]thiazol-6-yl)oxy)-N-methylpicolinamide.

See, e.g., WO2016/100882, which is incorporated herein by reference in its entirety.

In certain embodiments, exemplary therapeutic agents for conjoint administration are monoclonal antibodies or fragments thereof (see e.g., Bolliger (1993) Proc. Natl. Acad. Sci. USA 90:6444-6448; Poljak (1994) Structure 2:1121-1123). These therapeutic monoclonal antibodies and/or fragments thereof include, but are not limited to, anti-LAG-3 monoclonal antibody, anti-PD-1 antibody, anti-PD-L1 antibody, anti-PD-L2 antibody, anti-TIM-3 antibody, anti-CTLA-4 antibody, anti-TIGIT antibody, anti-OX40 antibody, anti-GITR antibody, adalimumab, afatinib, afutuzumab, alemtuzumab, atezolizumab, avelumab, axitinib, basiliximab, bavituximab, belimumab, bevacizumab, brentuximab, canakinumab, certolizumab, cetuximab, daclizumab, denosumab, durvalamab, eculizumab, efalizumab, elotuzumab, fostamatinib, gemtuzumab ozogamicin, golimumab, ibritumomab tiuxetan, infliximab, ipilimumab, lambrolizumab, lapatinib, lenvatinib, lirilumab, mogamulizumab, motavizumab, mubritinib, natalizumab, nivolumab, obinutuzumab, ofatumumab, omalizumab, palivizumab, panitumumab, pegaptani, pembrolizumab, pertuzumab, pidilizumab, ranibizumab, raxibacumab, rilotumumab, rituximab, tocilizumab, tositumomab-I-13, trastuzumab, tremelimumab, urelumab, ustekinumab, and varlilumab.

Combination therapies can also include administration of bispecific antibodies. Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of PD-1 blockade. Alternatively, antigen may be delivered directly to DCs by the use of bispecific antibodies which bind to tumor antigen and a dendritic cell specific cell surface marker.

Other antibodies which may be used to activate host immune responsiveness can be used in combination with the combination therapies described herein. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with PD-1 antibodies (Ito, N. et al. (2000) Immunobiology 201 (5) 527-40). Antibodies to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), 4-1BB (Mardiana, S. (2017), 15:77(6) 1296-1309), and ICOS (Hutloff, A. et al. (1999) Nature 397: 262-266) may also provide for increased levels of T cell activation.

Immunomodulatory agents and therapies that are suitable for use in the compositions and conjoint methods described herein include, but are not limited to, anti-T cell receptor antibodies such as anti-CD3 antibodies (e.g., Nuvion (Protein Design Labs), OKT3 (Johnson & Johnson) or anti-CD20 antibodies Rituxan (IDEC), antiCD52 antibodies (e.g., CAMPATH 1H (Ilex)), anti-CDlla antibodies (e.g., Xanelim (Genentech)); anti-cytokine or anti-cytokine receptor antibodies and antagonists such as anti-IL-2 receptor antibodies (Zenapax (Protein Design Labs)), anti-IL-6 receptor antibodies (e.g., MRA (Chugai)), and anti-IL-12 antibodies (CNT01275 (Janssen)), anti-TNFalpha antibodies (Remicade (Janssen)) or TNF receptor antagonist (Enbrel (Immunex)), anti-IL-6 antibodies (BE8 (Diaclone)) and siltuximab (CNT032 (Centocor)), and antibodies that immunospecifically bind to tumor-associated antigens (e.g., trastuzimab (Genentech)).

The combination therapies disclosed herein can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173:4919-28). Non-limiting examples of tumor vaccines that can be used include peptides of melanoma antigens, such as peptides of gp100, MAGE antigens, Trp-2, MART1 and/or tyrosinase or tumor cells transfected to express the cytokine GM-CSF.

Compounds disclosed herein can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigens may also be "neo-antigens" expressed in cancer cells because of somatic mutations that alter protein sequence or create fusion proteins between two unrelated sequences (ie. bcr-abl in the Philadelphia chromosome) or idiotype from B cell tumors.

Compounds disclosed herein can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43). In some embodiments, vaccination with immunoglobulin idiotype produced by malignant plasma cells is used. Other therapeutic vaccines include, but are not limited to, sipuleucel-T, gp100 vaccine, HPV-16 vaccination, and GVAX pancreas vaccine.

Other tumor vaccines may include the proteins from viruses implicated in human cancers such a Human Papilloma Viruses (HPV), Hepatitis Viruses (HBV and HCV), Kaposi's Herpes Sarcoma Virus (KHSV) and Preferentially Expressed Antigen In Melanoma (PRAME). In certain embodiments, the vaccine is selected from a viral vector vaccine, bacterial vaccine, cell-based vaccine, DNA vaccine, RNA vaccine, peptide vaccine or protein vaccine. See, e.g., Jeffrey Schlom, "Therapeutic Cancer Vaccines: Current Status and Moving Forward," J Natl Cancer Inst; 104:599-613 (2012). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269: 1585-1588; Tamura, Y. et al. (1997) Science 278:117-120).

Exemplary agents that can be conjointly administered with compounds disclosed herein include a therapeutic cancer vaccine or adoptive T cell therapy. In certain embodiments, the therapeutic cancer vaccine is a dendritic cell vaccine. The dendritic cell vaccine can be composed of autologous dendritic cells and/or allogeneic dendritic cells. In certain embodiments, the autologous or allogeneic dendritic cells are loaded with cancer antigens prior to administration to the subject. In certain embodiments, the autologous or allogeneic dendritic cells are loaded with cancer antigens through direct administration to the tumor. In certain embodiments, the adoptive T cell therapy comprises autologous and/or allogenic T-cells. In certain embodiments, the autologous and/or allogenic T-cells are targeted against tumor antigens.

In certain embodiments, non-limiting examples of cancer vaccines include tumor cell vaccines, antigen vaccines, dendritic cell vaccines, DNA vaccines, and vector based vaccines. Antigen vaccines boost the immune system by using one or more antigens, such as peptides. Antigen vaccines may be specific for a certain type of cancer because each tumor type may be identified by specific antigen profiles. Dendritic cell vaccines are often autologous vaccines, and must often be made individually for each subject. Non-limiting examples of dendritic vaccines are Sipuleucel-T and DCvax. For preparing DNA vaccines, vectors can be engineered to contain specific DNAs that can be injected into a subject which leads to the DNA being taken up by cells. Once the cells take up the DNA, the DNA will program the cells to make specific antigens, which can then provoke the desired immune response.

Pancreatic Cancer

Exemplary agents that that can be used conjointly with compounds disclosed herein for the treatment of pancreatic cancer include, but are not limited to, TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., R05126766); Notch signaling inhibitor (e.g., MK0752); monoclonal antibody-antibody fusion protein (e.g., L19IL2); curcumin; HSP90 inhibitor (e.g., tanespimycin, STA-9090); riL-2; denileukin diftitox; topoisomerase 1 inhibitor (e.g., irinotecan, PEP02); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., R04929097); ribonucleotide reductase inhibitor (e.g., 3-AP); immunotoxin (e.g., HuC242-DM4); PARP inhibitor (e.g., KU-0059436, veliparib); CTLA-4 inhbitor (e.g., CP-675,206, ipilimumab); AdVtk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG 12D LODER; and radiation therapy (e.g., tomotherapy, stereotactic radiation, proton therapy), surgery, and a combination thereof.

Small Cell Lung Cancer

Exemplary agents that that can be used conjointly with compounds disclosed herein to treat small cell lung cancer include, but are not limited to, etoposide, carboplatin, cisplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263), proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS833923); peptide cancer vaccine, and radiation therapy (e.g., intensity-modulated radiation therapy (IMRT), hypofractionated radiotherapy, hypoxia-guided radiotherapy), surgery, and combinations thereof.

Non-Small Cell Lung Cancer

Exemplary agents that that can be used conjointly with compounds disclosed herein to treat non-small cell lung cancer include, but are not limited to, vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafurgimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, R05083945), MET inhibitor (e.g., PF-02341066, ARQ 197), PI3K kinase inhibitor (e.g., XL147, GDC-0941), Raf/MEK dual kinase inhibitor (e.g., R05126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen, sodium), proteasome inhibitor (e.g., bortezomib, carfilzomib, NPI-0052, ixazomid), paclitaxel or a paclitaxel agent, docetaxel, IGF-1 receptor inhibitor (e.g., cixutumumab, MK-0646, OSI906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide-TNF alpha conjugate, dichloroacetate (DCA), HGF inhibitor (e.g., SCH 900105), SAR240550, PPAR-gamma agonist (e.g., CS-7017), gamma-secretase inhibitor (e.g., R04929097), epigenetic therapy (e.g., 5-azacitidine), nitroglycerin, MEK inhibitor (e.g., AZD6244), cyclin-dependent kinase inhibitor (e.g., UCN-01), cholesterol-Fus1, antitubulin agent (e.g., E7389), farnesyl-OHtransferase inhibitor (e.g., lonafarnib), immunotoxin (e.g., BB-10901, SS1 (dsFv) PE38), fondaparinux, vascular-disrupting agent (e.g., A VE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

Ovarian Cancer

Exemplary agents that that can be used conjointly with compounds disclosed herein to treat ovarian cancer include, but are not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024 oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-303), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agnet (e.g., Hu3S 193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., R04929097), Wee-1 inhibitor (e.g., MK-1775), antitubulin agent (e.g., vinorelbine, E7389), immunotoxin (e.g., denileukin diftitox), SB-485232, vascular-disrupting agent (e.g., A VE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy; and combinations thereof.

Myeloma

Exemplary agents that that can be conjointly administered with compounds disclosed herein to treat myeloma include, but are not limited to, thalidomide analogs, (e.g., lenalidomide), HSCT (Cook, R. (2008) J Manag Care Pharm. 14(7 Suppl):19-25), an anti-TIM-3 antibody (Hallett, W H D et al. (2011) J of American Society for Blood and Marrow Transplantation 17 (8): 1133-145), tumor antigen-pulsed dendritic cells, fusions (e.g., electrofusions) of tumor cells and dendritic cells or vaccination with immunoglobulin idiotype produced by malignant plasma cells (reviewed in Yi, Q. (2009) Cancer J. 15(6):502-10).

Renal Cell Carcinoma

Exemplary agents that that can be conjointly administered with compounds disclosed herein to treat renal cell carcinoma include, but are not limited to, interleukin-2 or interferon-α, a targeted agent (e.g., a VEGF inhibitor such as a monoclonal antibody to VEGF, e.g., bevacizumab (Rini, B. I. et al. (2010) J. Clin. Oncol. 28(13):2137-2143)); a VEGF tyrosine kinase inhibitor such as sunitinib, sorafenib, axitinib and pazopanib (reviewed in Pal S. K. et al. (2014) Clin. Advances in Hematology & Oncology 12(2):90-99)); an RNAi inhibitor) or an inhibitor of a downstream mediator of VEGF signaling, e.g., an inhibitor of the mammalian target of rapamycin (mTOR), e.g., everolimus and temsirolimus (Hudes, G. et al. (2007) N. Engl. J. Med. 356(22):2271-2281, Motzer, R. J. et al. (2008) Lancet 372: 449-456).

Chronic Myelogenous Leukemia

Exemplary agents that that can be conjointly administered with compounds disclosed herein to treat chronic myelogenous leukemia (CML) include, but are not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), a dual inhibitor (e.g., dasatinib, bosutinib), multikinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., R05045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

Chronic Lymphocyic Leukemia

Exemplary agents that that can be conjointly administered with compounds disclosed herein to treat chronic lymphocyic leukemia (CLL) include, but are not limited to, a chemotherapeutic agent (e.g., fludarabine, cyclophosph-amide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, R05072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/microparticle-bound anti-CD3/anti-CD28, autologous cytokine induced killer cells (CIK)), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-5016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., R05045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG 186, radiation therapy, bone marrow transplantation, stem cell transplantation, and combinations thereof.

Acute Lymphocyic Leukemia

Exemplary agents that that can be conjointly administered with compounds disclosed herein to treat acute lymphocyic leukemia (ALL) include, but are not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., R05045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, bone marrow transplantation, stem cell transplantation, radiation therapy, and combinations thereof.

Acute Myeloid Leukemia

Exemplary agents that that can be conjointly administered with compounds disclosed herein to treat acute myeloid leukemia (AML) include, but are not limited to, a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT388IL3 fusion protein, HDAC inhibitor (e.g., vorinostat, LBH589), plerixafor, mTOR inhibitor (e.g., everolimus), SRC inhibitor (e.g., dasatinib), HSP90 inhbitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., R05045337), mTOR inhibitor (e.g., everolimus), LY573636-sodium, ZRx-101, MLN4924, lenalidomide, immunotherapy (e.g., AHN-12), histamine dihydrochloride, bone marrow transplantation, stem cell transplantation, radiation therapy, and combinations thereof.

Multiple Myeloma

Exemplary agents that can be conjointly administered with compounds disclosed herein to treat multiple myeloma include, but are not limited to, a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, ixazomid), cancer vaccine (e.g., GVAX), CD-40 targeting agent (e.g., SGN-40, CHIR-12.12), perifosine, zoledronic acid, immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), bone marrow transplantation, stem cell transplantation, radiation therapy, and combinations thereof.

Prostate Cancer

Exemplary agents that can be conjointly administered with compounds disclosed herein to treat prostrate cancer include, but are not limited to, a chemotherapeutic agent (e.g., docetaxel, carboplatin, fludarabine, abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-303, bafetinib, CP-675,206, radiation therapy, surgery or a combination thereof.

Hodgkin's Lymphomas

Exemplary agents that that can be used conjointly with compounds disclosed herein for the treatment of Hodgkin's lymphomas include, but are not limited to, chemotherapeutics such as Doxorubicin (Adriamycin), bleomycin (Blenoxane), vinblastine (Velban, Velsar), dacarbazine, etoposide (Toposar, VePesid), cyclophosphamide (Cytoxan, Neosar), vincristine (Vincasar PFS, Oncovin), procarbazine (Matulane), prednisone, Ifosfamide (Ifex), carboplatin (Paraplatin), Mechlorethamine, Chlorambucil, methylprenisolone (Solu-Medrol), cytarabine (Cytosar-U), cisplatin (Platinol), Gemcitabine (Gemzar), vinorelbine (Navelbine), oxaliplatin (Eloxatin), Lomustine, Mitoxantrone, carmustine, melphalan, Bendamustine, Lenalidomide, and vinorelbine; either alone or in combinations; Brentuximab vedotin (Adcetris—a CD30 anti-body drug conjugate); Iodine$^{131}$-CHT25 antibody conjugate; HDAC inhibitors (e.g., vorinostat); m-TOR inhibitors (e.g., everolimus, temsirolimus); PI3K inhibitors (e.g., CAL-101, BAY80-6946, TGR-1202, BKM-120, AMG-319); JAK/STAT pathway inhibitors; Bcl-2 inhibitors (e.g., venetoclax); Mcl-1 inhibitors; multikinase inhibitors such as BAY 43-9006 (sorafenib); proteasome inhibitors (e.g., bortezomib (Velcade), NPI-0052); dual PI3K/HDAC targeted inhibitors (e.g., CUDC-907); NF-kB inhibitors; anti-PD-1 antibodies (e.g., nivolumab, pembrolizumab); anti-CTLA-4 antibodies (e.g., ipilimumab); anti-CD-20 antibodies (e.g., rituximab); anti-CD40 antibodies; anti-CD80 antibodies; and radiation therapy (e.g., tomotherapy, stereotactic radiation, proton therapy), surgery, and a combination thereof.

Non-Hodgkin's Lymphomas

Exemplary agents that that can be used conjointly with compounds disclosed herein for the treatment of Hodgkin's lymphomas include, but are not limited to, chemotherapeutics such as Doxorubicin (Adriamycin), bleomycin (Blenoxane), vinblastine (Velban, Velsar), dacarbazine, etoposide (Toposar, VePesid), cyclophosphamide (Cytoxan, Neosar), vincristine (Vincasar PFS, Oncovin), procarbazine (Matulane), prednisone, Ifosfamide (Ifex), carboplatin (Paraplatin), Mechlorethamine, Chlorambucil, methylprenisolone (Solu-Medrol), cytarabine (Cytosar-U), cisplatin (Platinol), Gemcitabine (Gemzar), vinorelbine (Navelbine), oxaliplatin (Eloxatin), Lomustine, Mitoxantrone, methotrexate, carmustine, melphalan, Bendamustine, Lenalidomide, and vinorelbine; either alone or in combinations; tyrosine kinase inhibitors (e.g., EGFR inhibitor (e.g., erlotinib, panitumumab, cetuximab, nimotuzumab); HDAC inhibitors (e.g., vorinostat); IRAK-4 inhibitors; HSP90 inhibitors (e.g., tanespimycin, STA-9090, CUDC-305); m-TOR inhibitors (e.g., everolimus, temsirolimus); PI3K inhibitors (e.g., CAL-101, BAY80-6946, TGR-1202, BKM-120, AMG-319); JAK/STAT pathway inhibitors; AKT inhibitors (e.g., RX-0201); Bcl-2 inhibitors (e.g., venetoclax); Mcl-1 inhibitors; multikinase inhibitors such as BAY 43-9006 (sorafenib); proteasome inhibitors (e.g., bortezomib (Velcade), NPI-0052); dual PI3K/HDAC targeted inhibitors (e.g., CUDC-907); NF-kB inhibitors; BTK inhibitors (e.g., ibrutinib); BET bromodomain inhibitors; anti-PD-1 antibodies (e.g., nivolumab, pembrolizumab); anti-CTLA-4 antibodies (e.g., ipilimumab); anti-CD-20 antibodies (e.g., rituximab); anti-CD40 antibodies; anti-CD80 antibodies; anti-CD30 antibodies (e.g. brentuximab vedotin (Adcetris)) and radiation therapy (e.g., tomotherapy, stereotactic radiation, proton therapy), surgery, and a combination thereof.

In certain embodiments, a compound and/or pharmaceutical composition of Formula (I) and a compound and/or pharmaceutical composition Formula (II) of the disclosure may be conjointly administered with non-chemical methods of cancer treatment. In a further embodiment, a compound and/or pharmaceutical composition of Formula (I) and a compound and/or pharmaceutical composition Formula (II) of the disclosure may be conjointly administered with radiation therapy. In a further embodiment, a compound and/or pharmaceutical composition of Formula (I) and a compound and/or pharmaceutical composition Formula (II) of the disclosure may be conjointly administered with surgery, with thermoablation, with focused ultrasound therapy, with cryotherapy or with any combination of these.

In certain embodiments, different compounds of the disclosure may be conjointly administered with one or more other compounds of the disclosure. Moreover, such combinations may be conjointly administered with other therapeutic agents, such as other agents suitable for the treatment of cancer, immunological or neurological diseases, such as the agents identified above. In certain embodiments, conjointly administering one or more additional chemotherapeutic agents with a compound and/or pharmaceutical composition of Formula (I) and a compound and/or pharmaceutical composition Formula (II) of the disclosure provides a synergistic effect. In certain embodiments, conjointly administering one or more additional chemotherapeutics agents provides an additive effect.

Pharmaceutical Compositions

In certain embodiments, the present disclosure provides a pharmaceutical composition comprising a compound of Formula (I) and a compound of Formula (II) as disclosed herein, optionally admixed with a pharmaceutically acceptable carrier or diluent.

The present disclosure also provides methods for formulating the disclosed compounds of Formula (I) and Formula (II) for pharmaceutical administration.

The compositions and methods of the present disclosure may be utilized to treat an individual in need thereof. In certain embodiments, the individual is a mammal such as a human or a non-human mammal. When administered to an animal, such as a human, the composition or the compound is optionally administered as a pharmaceutical composition comprising, for example, a compound of Formula (I) and a compound of Formula (II) of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of Formula (I) and/or a compound of Formula (II) of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of Formula (I) and/or a compound of Formula (II) of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of Formula (I) and/or Formula (II) of the disclosure, with the carrier and, optionally, one or more accessory ingredients. In general, the formulations are prepared by uniformly and intimately bringing into association a compound of the present disclosure with liquid carriers or finely divided solid carriers or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter or by incorporating sterilizing agents in the form of sterile solid compositions that can be dissolved in sterile water or some other sterile injectable medium immediately before use. These compositions may also optionally contain opacifying agents and may be of a composition that they release the active ingredient(s) only or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash or an oral spray or an oral ointment.

Alternatively or additionally, compositions can be formulated for delivery via a catheter, stent, wire or other intraluminal device. Delivery via such devices may be especially useful for delivery to the bladder, urethra, ureter, rectum or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to an active compound, excipients such as lactose, talc, silicic acid, aluminum hydroxide, calcium silicates and polyamide powder or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference in its entirety. If desired, liquid ophthalmic formulations have properties similar to that of lacrimal fluids, aqueous humor or vitreous humor or are compatible with such fluids. A preferred route of administration is local administration (e.g., topical administration, such as eye drops or administration via an implant).

A suppository also is contemplated as being within the scope of this disclosure.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of Formula (I) and the compound of Formula (II) of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Unless defined otherwise, all technical and scientific terms used herein have the same meaning as is commonly understood by one of skill in art to which the subject matter herein belongs. As used herein, the following definitions are supplied in order to facilitate the understanding of the present disclosure.

The term "acyl" is art-recognized and refers to a group represented by the general formula hydrocarbylC(O)—, preferably alkylC(O)—. Acyl groups include —C(O)CH$_3$, —C(O)CH$_2$CH$_3$ and the like.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A C$_1$-C$_6$ straight chained or branched alkyl group is also referred to as a "lower alkyl" group. An alkyl group may be optionally substituted at one or more positions as permitted by valence. Such optional substituents include, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN or the like.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds. A cycloalkyl group may be substituted at one or more positions, as permitted by valence, with any optional substituents described herein. Cycloalkyl groups include but are not limited to cyclopropyl, cyclobutyl, cyclopentyl and cyclohexyl.

The term "carboxy" or "carboxylic acid", as used herein, refers to a group represented by the formula —CO$_2$H. The term "carboxylate" refers to a group represented by the formula —(CO$_2$)$^-$.

The term "guanidino", as used herein, refers to —NH—C(=N)—NH$_2$ group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, indole, 1,2,4-oxadiazole, 1,2,4-thiadiazole, 1,3,4-oxadiazole, 1,3,4-thiadiazole, benzimidazole, pyrimidine, and the like. A heteroaryl group may be substituted at one or more positions, as permitted by valence, with any optional substituents described herein.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, azepane, azetidine, 2,3-dihydrobenzo[b][1,4]dioxine, tetrahydro-2H-pyran, lactones, lactams, and the like. Heterocyclyl groups may be optionally substituted as permitted by valence.

As used herein, the term "hydroxy" or "hydroxyl" refers to —OH group.

The term "lower" when used in conjunction with a chemical moiety, such as, acyl, acyloxy, alkyl, alkenyl, alkynyl or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl or alkoxy substituents defined herein are respectively lower acyl, lower acyloxy, lower alkyl, lower alkenyl, lower alkynyl or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl or an acyl), a thiocarbonyl (such as a thioester, a thioacetate or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

As used herein, a therapeutic that "prevents" a disorder or condition refers to a compound that, in a statistical sample, reduces the occurrence of the disorder or condition in the treated sample relative to an untreated control sample or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate or stabilize the existing unwanted condition or side effects thereof).

The term "prodrug" is intended to encompass compounds which, under physiologic conditions, are converted into the therapeutically active agents of the present disclosure (e.g., a compound of formula (I) or a compound of formula (II)). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present disclosure. In certain embodiments, some or all of the compounds of formula (I) or formula (II) in a formulation represented above can be replaced with the corresponding suitable prodrug, e.g., wherein a hydroxyl in the parent compound is presented as an ester or a carbonate or carboxylic acid present in the parent compound is presented as an ester.

As used herein, the term "comprise" or "comprising" is generally used in the sense of include, that is to say permitting the presence of one or more additional (unspecified) features or components.

As used herein, the term "including" as well as other forms, such as "include", "includes," and "included," is not limiting.

As used herein, the term "amino acid" means a molecule containing both an amino group and a carboxyl group, and includes its salts, esters, combinations of its various salts, as well as tautomeric forms. In solution, at neutral pH, amino and acid groups of an amino acid can exchange a proton to form a doubly ionized, through overall neutral, entity identified as a zwitterion. In some embodiments, the amino acids are $\alpha$-, $\beta$-, $\gamma$- or $\delta$-amino acids, including their stereoisomers and racemates. As used herein, the term "L-amino acid" denotes an $\alpha$-amino acid having the levorotatory configuration around the $\alpha$-carbon, that is, a carboxylic acid of general formula CH(COOH)(NH$_2$)-(side chain), having the L-configuration. The term "D-amino acid" similarly denotes a carboxylic acid of general formula CH(COOH)(NH$_2$)-(side chain), having the dextrorotatory-configuration around the α-carbon. Side chains of L-amino acids can include naturally occurring and non-naturally occurring moieties. Non-naturally occurring (i.e., unnatural) amino acid side chains are moieties that are used in place of naturally occurring amino acid side chains in, for example, amino acid analogs.

An "amino acid residue" as used herein, means a moiety sharing structural similarity to the parent amino acid. An amino acid residue may be covalently bonded to another chemical moiety via the amino group of the residue or the carboxylate group of the residue (i.e., a hydrogen atom of —NH$_2$ or —OH is replaced by a bond to another chemical moiety).

Amino acids include the twenty standard amino acids used by most biological organisms in protein synthesis. Unnatural amino acid residues may be selected from, but are not limited to, alpha and alpha-disubstituted amino acids, N-alkyl amino acids, and natural amino acids substituted with lower alkyl, aralkyl, hydroxyl, aryl, aryloxy, heteroarylalkyl or acyl.

For example, lysine can be substituted to form an unnatural amino acid, e.g., at a carbon atom of its side chain or alternatively by mono- or dialkylation of its terminal NH$_2$ group (e.g., wherein the amino group of the lysine sidechain is taken together with its substituents to form a heterocyclic ring such as piperidine or pyrrolidine). In another example, the terminal amino group of the lysine sidechain can form a ring with the amino acid backbone, as in capreomycidine. Further unnatural derivatives of lysine include homolysine and norlysine. The sidechain of lysine can alternatively be substituted with a second amino group. In another example, the alkyl portion of the lysine side chain can be incorporated into a carbocyclic ring structure to form a semirigid analog, such as, e.g., cyclohexyl or cyclopentyl.

In certain embodiments, the unnatural amino acid can be a derivative of a natural amino acid having one or more double bonds.

In other example embodiments, in threonine, the beta-methyl group can be replaced with an ethyl, phenyl or other higher alkyl group. In histidine, the imidazole moiety can be substituted or alternatively, the alkylene backbone of the side chain can be substituted.

Further examples of unnatural amino acids include homoserine, and homologs of natural amino acids.

In further example embodiments, an unnatural amino acid can be alkylated (e.g., methylated) at the alpha position.

Further examples of unnatural amino acids include alpha, beta- and beta, gamma-dehydroamino amino acid analogs.

Further exemplary amino acids include penicillamine and betamethoxyvaline.

Further examples of unnatural amino acids include the amino acids wherein the side chain comprises amino, alkylamino, acylamino, —COO-alkyl, cycloalkyl, heterocyclyl, heteroaryl, guanidino, (cycloalkyl)alkyl, (heterocyclyl)alkyl and (heteroaryl)alkyl.

"Modified N-terminal amino group" and "modified C-terminal carboxyl group" mean that the amino group or carboxyl group is altered.

Modification of the N-terminal amino group is preferably with the general formula —NR$_x$R$_y$; wherein R$_x$ is hydrogen or alkyl and R$_y$ is alkyl, alkenyl, —C(=NH)NH$_2$, alkynyl or acyl.

Examples of N-terminal modifications include, but are not limited to, are acetylated, formylated or guanylated N-termini.

Modification of the C-terminal carboxyl group is preferably with the general formula COR$_z$ (R$_z$ replaces the hydroxyl group of the last amino acid); wherein R$_z$ is —NR$_b$R$_c$, alkoxy, amino or an imide. For example, the C-terminus may be esterified or amidated.

This disclosure includes pharmaceutically acceptable salts of compounds of the disclosure and their use in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization or adventitious to such solvent.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "stereoisomers" refers to any enantiomers, diastereoisomers or geometrical isomers, such as of the compounds of the disclosure. When compounds of the disclosure are chiral, they can exist in racemic or in optically active form. Since the pharmaceutical activity of the racemates or stereoisomers of the compounds according to the disclosure may differ, it may be desirable to use compounds that are enriched in one of the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline) or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

In certain embodiments, compounds of the disclosure may be racemic. In certain embodiments, compounds of the disclosure may be enriched in one enantiomer. For example, a compound of Formula (I) and/or a compound of Formula (II) of the disclosure may have greater than 30% ee, 40% ee, 50% ee, 60% ee, 70% ee, 80% ee, 90% ee or even 95% or greater ee. In certain embodiments, compounds of the disclosure may have more than one stereocenter. In certain such embodiments, compounds of the disclosure may be enriched in one or more diastereomer. For example, a compound of Formula (I) and/or a compound of Formula (II) of the disclosure may have greater than 30% de, 40% de, 50% de, 60% de, 70% de, 80% de, 90% de or even 95% or greater de.

The term "subject" includes mammals (especially humans) and other animals, such as domestic animals (e.g., household pets including cats and dogs) and non-domestic animals (such as wildlife).

Naturally-occurring amino acids (L-form) are identified throughout the description and claims by the conventional three-letter abbreviations indicated in the below table.

TABLE 7

Amino acid codes

| Name | 3-letter code |
| --- | --- |
| Alanine | Ala |
| Arginine | Arg |
| Asparagine | Asn |
| Aspartic acid | Asp |
| Glutamic acid | Glu |
| Glutamine | Gln |
| Histidine | His |
| Isoleucine | Ile |
| Lysine | Lys |
| Methionine | Met |
| Phenylalanine | Phe |
| Proline | Pro |
| Serine | Ser |
| Threonine | Thr |
| Tyrosine | Tyr |
| Valine | Val |

The abbreviations used in the entire specification may be summarized herein below with their particular meaning.

° C. (degree Celsius); % (percentage); EDTA (Ethylenediaminetetraacetic acid) g or gr (gram); h or hr (Hours); M (Molar); μl (Microlitre); mL (Millilitre); mg (Milligram); min (Minutes); Na (Sodium); PD-1/PD1 (Programmed cell death 1); PD-L1 (Programmed death-ligand 1); PD-L2 (Programmed cell death 1 ligand 2);

EXAMPLES

The invention now being generally described, it will be more readily understood by reference to the following examples which are included merely for purposes of illustration of certain aspects and embodiments of the present invention, and are not intended to limit the invention.

Example 1: Preparation of Exemplary Compounds

The synthetic procedures for the preparation of exemplary inhibitors were described WO2016142833 A1 and WO2015033299 A1, which are incorporated by reference in their entirety.

Example 2: Immune Efficacy Study of the Effect of Cmd 1 and Cmd 32 in the CT-26 Syngeneic (Balb/c Female) Mouse Tumor Model The purpose of this study is to determine the effect of Cmd 1 and Cmd 32 on growth inhibition (efficacy) in CT-26 tumor bearing mice when administered once daily by oral gavage as single agents or in combination. Cmd 1 and Cmd 32 are small molecule immune modulating agents for treatment of cancer.

Study Animals

Female Balb/c Mice from Charles River Labratories—20-25 grams; 9-10 weeks old; Strain code: 028.

Dosing and Materials

TABLE 8

Compounds and Dosing

| Test Agent | Dose | Frequency | Route of administration |
| --- | --- | --- | --- |
| Cmd 1 | 100 mpk or 250 mpk | QD | PO |
| Cmd 32 | 50 mpk | QD | PO |
| PD-1 antibody (29F.1A12 clone) | 100 μg/mouse | QD; 2x/week | IP |
| Rat IgG2a Isotype control (RTK2758 clone) antibody | 100 μg/mouse | QD; 2x/week | IP |

TABLE 9

Reagents and Materials

| Reagent | Clone | Source | Stock concentration |
| --- | --- | --- | --- |
| anti-mouse CD279 (PD-1) Antibody | 29F.1A12 | BioLegend | 2.45 mg/mL |
| Rat IgG2a Isotype control | RTK2758 | BioLegend | 2.7 mg/mL |
| PE Hamster Anti-mouse VISTA | MH5A | BioLegend | 0.2 mg/mL |
| PE anti-mouse CD366 (Tim-3) | B8.2C12 | BioLegend | 0.2 mg/mL |
| PE/Cy7 anti-mouse CD279 (PD-1) | 29F.1A12 | BioLegend | 0.2 mg/mL |

CT-26 Tumor Cell Culture, Cell Passaging and Cell Harvesting

CT-26 cells were expanded in T225 tissue culture treated flasks in RPMI-1640 medium supplemented with 10% FBS (complete DMEM medium) and cultured at 37° C. (5% $CO_2$) in a humidified cell culture incubator. Cells were passaged every 3-4 days by detachment with 1× Trypsin/EDTA. Cells were re-plated on 5 flasks in complete RPMI1640 medium.

Inoculation Administration

On the day of implantation, the cells were collected from flasks washed with phosphate buffer solution and detached with Trypsin/EDTA and washed once in phosphate buffer solution with no additives. Cells were resuspended in serum free DMEM at a final concentration of $1 \times 10^6$ cells/mL and kept on ice until administered to mice. The cells were kept on ice for no more than 1 hour before administration to the mice. Animals were shaved on the right flank the day before implantation. On day of implantation animals were wiped with an alcohol wipe and injected in the right flank with $1 \times 10^5$ cells in 100 uL of media. Animals were grouped around day 7-15 once found to have viable tumors that could be well palpated around 100-200 mm$^3$. They were randomized by tumor volume and treatment started with Cmd 1 the following day. Tumor volumes were collected when tumors were palpable by use of the LabCat software (In-Life & Tumor). Using Calipers a length and width measurement was collected and used to calculate tumor volume by the calculation Tumor Length*Tumor Width*Tumor Width*0.5.

Grouping

TABLE 10

Efficacy Groups (Dosing starts after Randomization)

| Group | N | Dosing Details (dosing schedule in parentheses) | |
|---|---|---|---|
| 1 | 20 | Vehicle: Water (QD) | |
| 2 | 15-18 | Cmd 1 100 mpk (QD) | |
| 3 | 15-18 | Cmd 1 250 mpk (QD) | |
| 4 | 10-12 | Cmd 32 50 mpk (QD) | |
| 5 | 10-12 | Cmd 1 100 mpk (QD) | Cmd 32 50 mpk (QD) |
| 6 | 5 | Rat IgG2a Isotype control (RTK2758 clone) antibody 100 µg/mouse; QD; 2x/week | |
| 7 | 5 | PD-1 antibody (29F.1A12 clone) 100 µg/mouse; QD; 2x/week | |

Study Schedule and Analysis

Figure 1B:
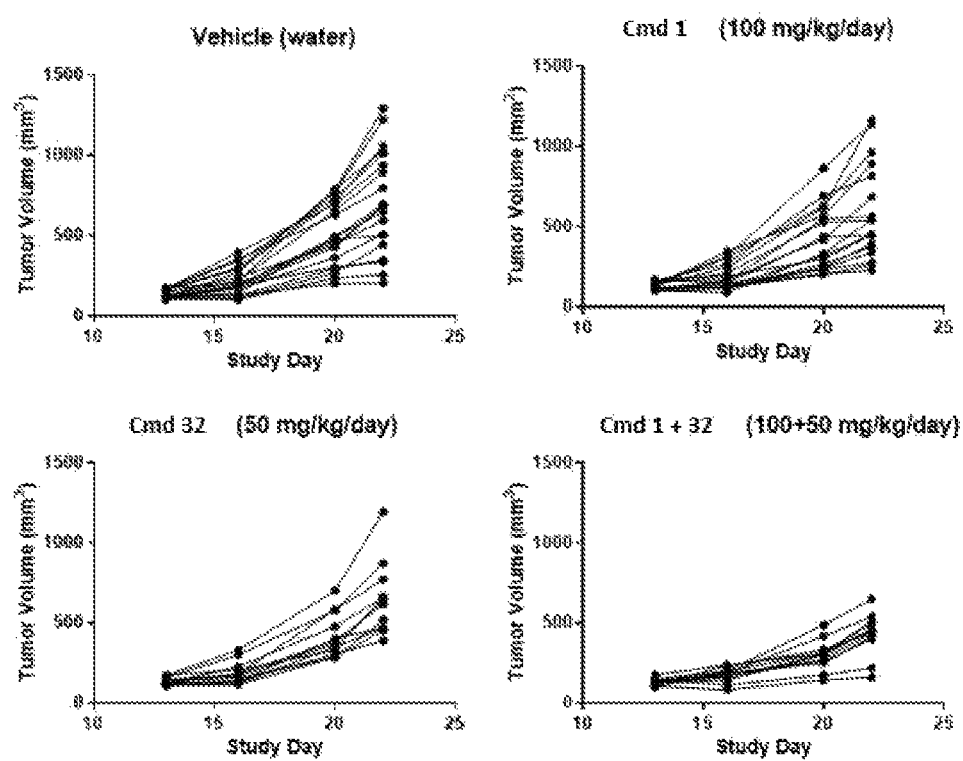
FIG. 1B. Change in tumor volume (mm$^3$) during treatments with water, Cmd 1 (100 mg/kg/day), Cmd 32 (50 mg/kg/day) and conjoint administration of Cmd 1 and 32 (100 and 50 mg/kg/day respectively), FIG. 2A. Tumor CD8$^+$: Treg ratio post treatments with Cmd 1 (100 mg/kg), Cmd 32 (50 mg/kg), conjoint administration of Cmd 1 and Cmd 32 (100 and 50 mg/kg respectively), and anti-PD-1 antibody.
Figure 2A:
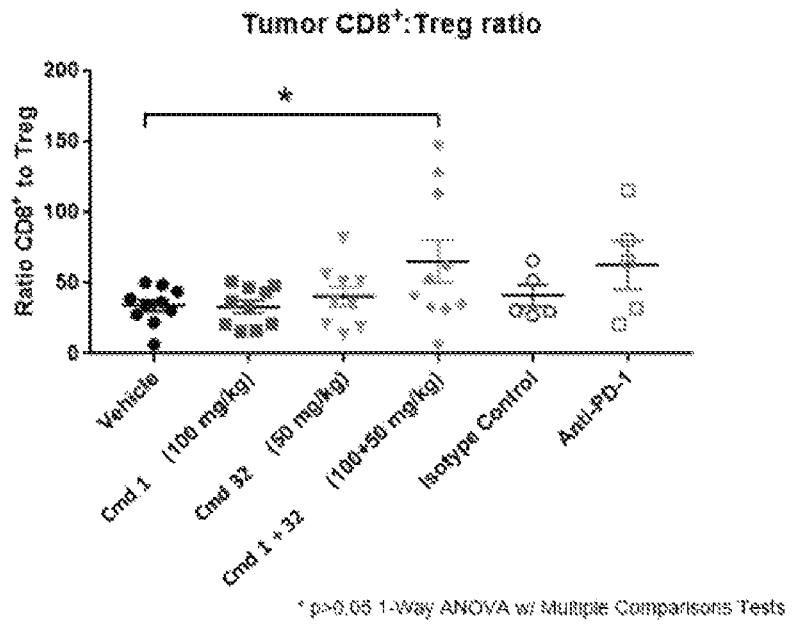
FIG. 2B. Tumor Granzyme-B$^+$ PD-1$^+$TIM-3$^+$: as a percent of CD8 post treatments with Cmd 1 (100 mg/kg), Cmd 32 (50 mg/kg), conjoint administration of Cmd 1 and Cmd 32 (100 and 50 mg/kg respectively).
FIG. 2C. Tumor Granzyme-13$^+$ PD-1$^+$TIM-3$^-$: as a percent of CD8 post treatments with Cmd 1 (100 mg/kg), Cmd 32 (50 mg/kg), conjoint administration of Cmd 1 and Cmd 32 (100 and 50 mg/kg respectively).
Figure 2B:
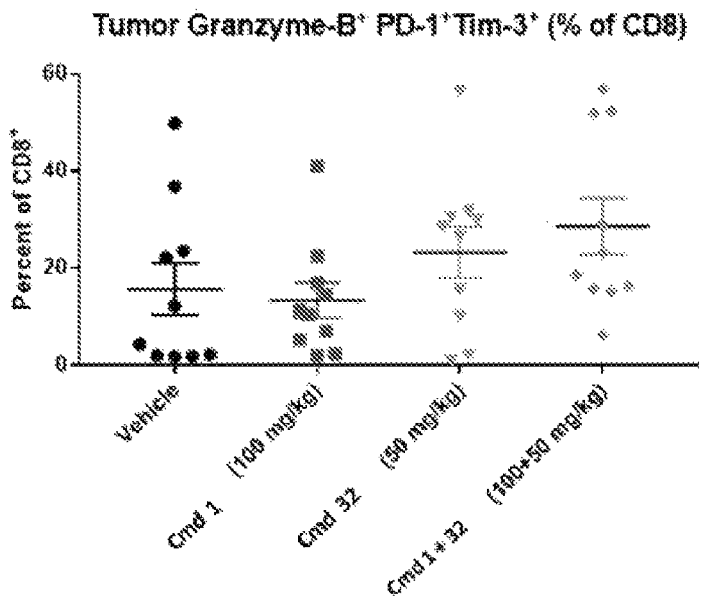
Figure 2C:
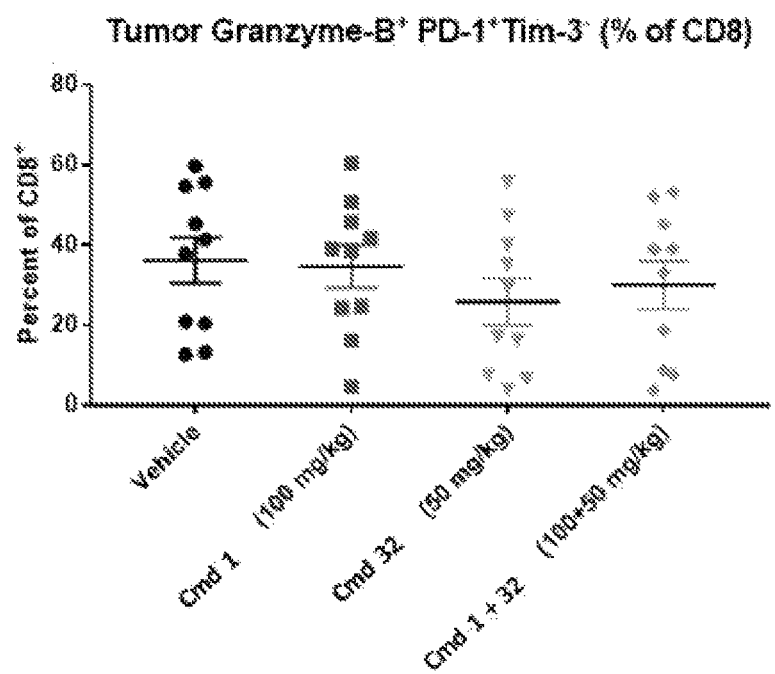

Animals were monitored until tumors were palpable and were then measured until tumor volume reached 100-200 mm$^3$. They were then randomized into groups using LabCat software and dosing started the following day. Blood was collected in EDTA tubes and kept on ice. Tumor were collected in 15 mL tubes with RPMI-1640 w/10% FBS on ice. Tumors proceeded to the Miltenyi Biotec mouse tumor dissociation kit. Tumor cells were counted on a MACSQuant Analyzer with propidium iodide (PI) for live/dead discrimination. Percent tumor growth inhibition on Day 20 is tabulated below (Table 11). Tumor volume of individual animals on day 20 and the tumor growth over the course of the study are represented in FIG. 1A and FIG. 1B respectively. Cell-surface marker assays were used to identify intratumoral T cell populations and calculate CD8+ (CTL; cytotoxic T-cell):Treg (regulatory T cell) ratio. Combined treatment with Cmd 1 and Cmd 32 (i.e., group 5) promoted anti-tumor activity (i.e., increased CD8+: Treg) as effectively as PD-1 blockade (positive control, Anti-PD-1), as represented in FIG. 2A. Cmd 32 effectively blocks the TIM-3 pathway allowing the survival of active CD8+, intratumoral T cells, observed by the increase in granzyme-B+/PD-1+/Tim-3$^+$ T cells and concomitant decrease in granzyme-B+/PD-1+/Tim-3$^-$ T cells. Moreover, administering Cmd 1 and Cmd 32 in combination synergistically promotes active, intratumoral, CD8+ CTLs (see FIGS. 2B and 2C).

TABLE 11

Percent tumor growth inhibition (TGI)

| | % TGI (Day 20) | | |
|---|---|---|---|
| | Cmd 1 (100 mg/kg) | Cmd 32 (50 mg/kg) | Cmd 1 and 32 (100 and 50 mg/kg respectively) |
| Vehicle (H$_2$O) | 23 | 24 | 56 |

Example 3: Efficacy of Cmd 32 in Combination with Cmd 1 in MC38 Syngenic Model

Study Materials

Cmd 32 and Cmd 1 were stored in −16 to −20° C. until formulation preparation. Fresh formulations were prepared every day prior to dosing.

Female C57BL/6 mice bred in-house were used in this efficacy study in the MC38 model. Animals were 6-8 weeks-old and weighed between 13 and 21 g. Animals were marked individually with tail marks and kept in cages that were identified by a cage card showing the study code, date of experimentation, sex and number of animals. During the experiment, the animals were weighed daily.

Tumor cells were cultured according to the procedure explained in the literature (U.S. Pat. No. 9,333,256; A. Filatenkov et al., J. Immunol., 2009. 183(11): 7196-7203). Tumor cells were ensured mycoplasma free by performing mycoplasma detection with MYCOALERT® Mycoplasma Detection Kit (Lonza) in accordance with manufacturer instructions. MYCOALERT® Assay is a selective biochemical test that exploits the activity of mycoplasmal enzymes. Viable mycoplasma would be lysed and enzymes react with MYCOALERT® substrate, catalyzing the conversion of ADP to ATP. By measuring the level of ATP in a sample both before and after the addition of MYCOALERT® substrate, a ratio can be obtained which is indicative of the presence or absence of mycoplasma. Mycoplasma test was assayed in duplicate from the culture supernatants of the cell lines and compared to negative and positive controls (MYCOALERT® Assay Control Set). U.S. Pat. No. 9,333,256 is hereby incorporated by reference in its entirety.

Mortality/morbidity of animals, body weight loss and clinical symptoms were monitored. During study period all moribund animals were sacrificed and animals losing >20% of their body weight were also sacrificed. Body weights were recorded every day and clinical signs of toxicity were recorded once a day. Survival was recorded every day. A 15-20% loss of the body weight and/or animal death was considered as the criteria for toxicity. Behavioural, nesting and gross observations for clinical signs were made at least once every day during the course of the study.

Functional grade anti-mouse PD-1 antibody (J43 clone) in aqueous PBS buffer with low endotoxin (azide free) was procured from BioXcell (catalog number: BE0033-2, lot number 5729/0915). Functional grade anti-TIM 3 antibody (RMT.3.23 clone), in aqueous PBS buffer with low endotoxin (azide free) was procured from BioXcell (catalog number: BE0115, lot number 5956-1/1215).

Experimental Procedure

MC38 cells were cultured according to the information in published literature (A. Filatenkov et al., J. Immunol., 2009. 183(11): 7196-7203; S. F. Ngiow et al., Cancer Res., 2011. 71(10): 3540-3551). MC38 cells were grown and 0.5×10$^6$ cells were injected in complete culture medium to the right flank position of female C57BL/6 mice on day 0. Ten animals were included in each treatment group. Dosing volume for all groups were 10 ml/kg body weight. Cells were injected on day −4, dosing started on day 1 and continued to day 15. Tumor volumes were measured 3 times a week, body weight and clinical signs were monitored every day. 1% Tween80+10% Capmul+89% of 5% HPCD+ 0.1 M Citric acid+0.1% EDTA was used as vehicle for Cmd 32 for dosing by oral route (PO). Water was used as vehicle for Cmd 1 for dosing by oral route. Functional grade anti-TIM 3 antibody (RMT.3.23 clone), in aqueous PBS buffer with low endotoxin (azide free) was dosed intraperitoneally at 10 mg/kg twice every week (Days 1, 4, 8 and 11).

TABLE 12

Treatment groups

| Treatment/dose group | Number of animals | Route | Dosing frequency |
|---|---|---|---|
| 1% Tween80 + 10% Capmul + 89% of 5% HPCD + 0.1M Citric acid + 0.1% EDTA | 10 | Oral | Once a day |
| Anti-PD-1 (J43) 100 µg/animal | 10 | IP | Once a week |
| Anti-Tim3 ab (10 mg/kg) | 10 | IP | twice a week |
| Cmd 32, 10 mg/kg | 10 | Oral | Once a day |
| Cmd 1, 10 mg/kg | 10 | Oral | Once a day |
| Cmd 32, 3 mg/kg + Cmd 1, 1 mg/kg | 10 | Oral | Once a day |
| Cmd 32, 3 mg/kg + Cmd 1, 3 mg/kg | 10 | Oral | Once a day |
| Cmd 32, 3 mg/kg + Cmd 1, 10 mg/kg | 10 | Oral | Once a day |
| Cmd 32, 10 mg/kg + Cm 1, 3 mg/kg | 10 | Oral | Once a day |
| Cmd 32, 10 mg/kg + Cmd 1, 10 mg/kg | 10 | Oral | Once a day |

At the end of the study (30 min after the last dose), animals were examined externally for possible abnormalities, weighed and sacrificed by $CO_2$ asphyxiation.

Data Analysis

All statistical analyses were performed using GRAPHPAD PRISM® 7. Statistical analyses of mean body weights, metastatic counts were performed using the Dunnett's test (ANOVA comparison) and Student's t test. All groups were compared with each other. A p value less than 0.05 was considered as significant.

Results

Figure 3:
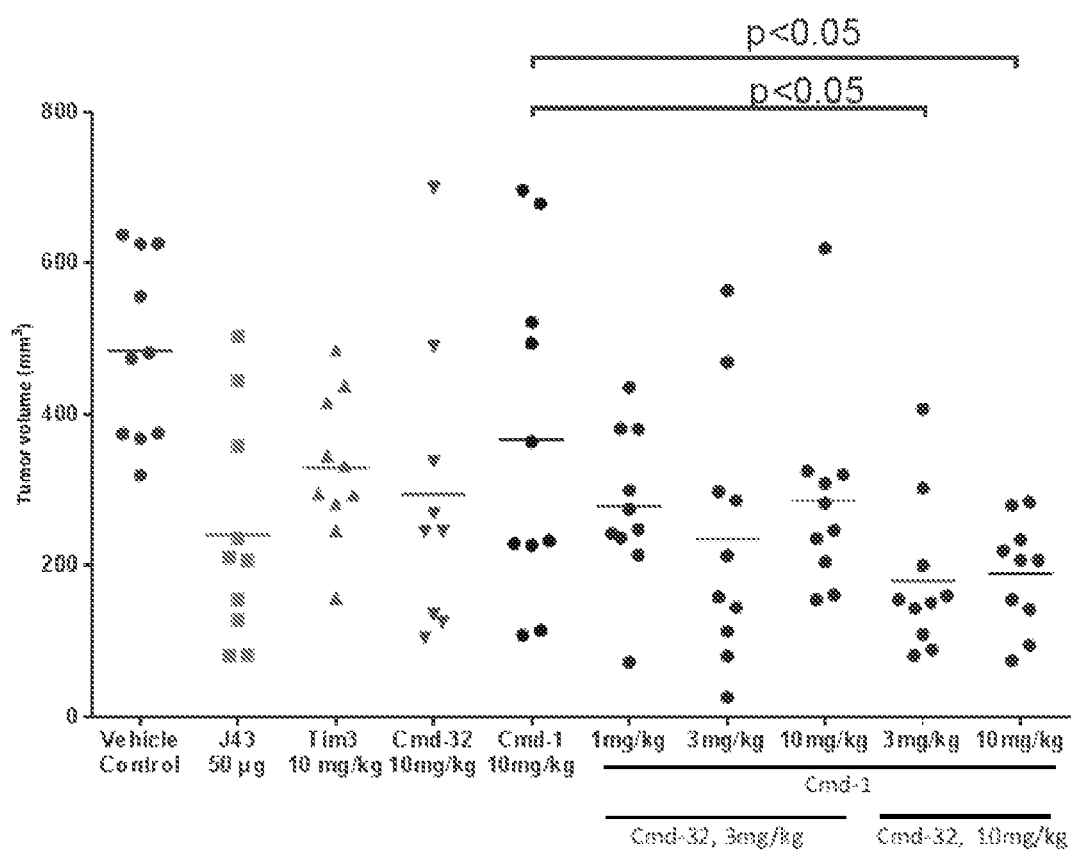
FIG. 3. In vivo efficacy of Cmd 32 in combination with Cmd 1 in MC38 mouse model. Significant additive efficacy was observed when 3 or 10 mg/kg of Cmd 1 was conjointly administered with 10 mg/kg of Cmd 32.

Animals showed no treatment-related body weight changes upon dosing. No treatment related clinical signs were observed in any of the groups. Two animals (one in the vehicle control group and another in Cmd 32, 10 mg/kg group) were found dead. No gross pathology observations were noted upon necropsy and hence mortalities couldn't reliably be attributed to treatment. Percent tumor growth inhibition is tabulated in the table below (Table 13) and tumor volume of individual animals are represented in FIG. 3.

TABLE 13

Percent tumor growth inhibition (TGI)

| | | MC38 SC Cmd 32 dose (mg/kg) | |
|---|---|---|---|
| Model | 0 mg/kg | 3 mg/kg | 10 mg/kg |
| Cmd 1 | 0 mg/kg | 0 | | 40 |
| | 1 mg/kg | | 44 | |
| | 3 mg/kg | | 53 | 65 |
| | 10 mg/kg | 25 | 42 | 63 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of modulating an immune response in a subject, comprising administering to the subject an effective amount of an inhibitor of the VISTA pathway and an effective amount of an inhibitor of the TIM-3 pathway, wherein the inhibitor of the VISTA pathway is a compound of formula (I) or a pharmaceutically acceptable salt thereof:

Formula (I)

further wherein:

G represents hydrogen or $(C_1$-$C_6)$alkyl;

$R_a$ represents $(C_1$-$C_6)$alkyl substituted with —OH, —C(O)$NR_xR_y$, —$NR_xR_y$, guanidino, carboxylic acid, heteroaryl, or aryl-OH;

$R_{a'}$ represents hydrogen; or $R_a$ and $R_{a'}$ taken together with the atom to which they are attached form a 5- to 6-membered ring;

$R_b$ represents $(C_1$-$C_6)$alkyl, optionally substituted with —OH, —C(O)$NR_xR_y$, —$NR_xR_y$, carboxylic acid, or heteroaryl; wherein the heteroaryl is optionally further substituted with hydroxyl;

$R_c$ represents hydrogen; or $R_b$ and $R_c$ taken together with the atoms to which they are attached form a 5- to 6-membered ring;

$R_d$ represents H, $(C_1$-$C_6)$alkyl substituted with —OH, —$NR_xR_y$, or carboxylic acid;

$R_e$ represents hydrogen; or $R_d$ and $R_e$ taken together with the atoms to which they are attached form a 5- to 6-membered ring optionally containing 1 to 3 heteroatoms selected from O, NH or S; and $R_x$ and $R_y$ independently represent hydrogen, $(C_1$-$C_6)$ alkyl, $(C_2$-$C_6)$acyl, or $(C_1$-$C_6)$cycloalkyl; or $R_x$ and $R_y$ taken together with the atom to which they are attached form a 5- to 6-membered ring; and the inhibitor of the TIM-3 pathway is a compound of formula (II) or a pharmaceutically acceptable salt thereof:

Formula (II)

wherein:

Z represents —OH or —NH-G';

G' represents hydrogen or $(C_1$-$C_6)$alkyl;

Y represents hydrogen or a group represented by the following structural formula

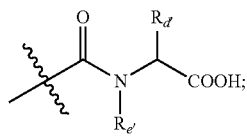

$R_{a''}$ represents $(C_1-C_6)$alkyl substituted with —OH, —$NR_xR_y$, —$SR_x$, carboxylic acid, guanidino, or aryl, wherein the aryl group is optionally further substituted with hydroxyl; or $R_a$ and G taken together with the atom to which they are attached form a 5- to 6-membered ring containing 1 to 3 heteroatoms selected from O, N or S;

$R_{a'''}$ represents hydrogen; or $R_{a''}$ and $R_{a'''}$ taken together with the atom to which they are attached form a 5- to 6-membered ring, optionally containing 1 to 3 heteroatoms selected from O, N or S;

$R_{b'}$ represents $(C_1-C_6)$alkyl, optionally substituted with —$C(O)NR_xR_y$, —$NR_xR_y$, or carboxylic acid;

$R_{c'}$ represents hydrogen; or $R_{b'}$ and $R_{c'}$ taken together with the atoms to which they are attached form a 5- to 6-membered ring containing 1 to 3 heteroatoms selected from O, N or S, wherein the 5- to 6-membered ring is optionally further substituted with hydroxyl;

$R_{d'}$ represents $(C_1-C_6)$alkyl, optionally substituted with —$OR_x$, carboxylic acid, or aryl-OH; $R_{e'}$ represents hydrogen; or $R_{d'}$ and $R_{e'}$ taken together with the atoms to which they are attached form a 5- to 6-membered ring containing 1 to 3 heteroatoms selected from O, N or S; and $R_{x'}$ and $R_{y'}$ independently represent hydrogen, $(C_1-C_6)$ alkyl or $(C_2-C_6)$acyl.

2. The method of claim 1, wherein G represents hydrogen or methyl.

3. The method of claim 1, wherein $R_a$ represents —$(CH_2)_2C(O)OH$ or $(C_1-C_4)$alkyl, wherein $(C_1-C_4)$alkyl is substituted with —OH, —$C(O)NR_xR_y$, —$NR_xR_y$, guanidino, heteroaryl, or aryl-OH.

4. The method of claim 1, wherein $R_a$ and $R_{a'}$ taken together with the atoms to which they are attached form a cyclopentyl ring or cyclohexyl ring.

5. The method of claim 1, wherein $R_b$ represents —$CH_2C(O)OH$ or $(C_1-C_6)$alkyl, wherein $(C_1-C_6)$alkyl is optionally substituted with —OH, —$C(O)NR_xR_y$, or heteroaryl, wherein the heteroaryl is optionally further substituted with hydroxyl.

6. The method of claim 1, wherein $R_b$ and $R_c$ taken together with the atoms to which they are attached form a pyrrolidine ring.

7. The method of claim 1, wherein $R_d$ represents —$CH_2OH$, —$CH(CH_3)OH$, —$(CH_2)_4$—$NH_2$, or —$CH_2C(O)OH$.

8. The method of claim 1, wherein $R_d$ and $R_e$ taken together with the atoms to which they are attached form a pyrrolidine ring.

9. The method of claim 1, wherein:
G represents hydrogen or $(C_1-C_6)$alkyl;
$R_a$ represents —$(CH_2)_2C(O)OH$ or $(C_1-C_4)$alkyl, wherein $(C_1-C_4)$alkyl is substituted with —OH, —$C(O)NR_xR_y$, —$NR_xR_y$, guanidino, heteroaryl, or aryl-OH;

$R_{a'}$ represents hydrogen; or $R_a$ and $R_{a'}$ taken together with the atom to which they are attached form a 5- to 6-membered ring;

$R_b$ represents —$CH_2C(O)OH$ or —$(C_1-C_6)$alkyl, wherein $(C_1-C_6)$alkyl is optionally substituted with —OH, —$C(O)NR_xR_y$, —$NR_xR_y$, heteroaryl; wherein the heteroaryl is optionally further substituted with hydroxyl;

$R_c$ represents hydrogen; or $R_b$ and $R_c$ taken together with the atoms to which they are attached form a 5- to 6-membered ring;

$R_d$ represents H, —$(C_1-C_6)$alkyl substituted with —OH, —$NR_xR_y$, or carboxylic acid;

$R_e$ represents hydrogen; or $R_d$ and $R_e$ taken together with the atoms to which they are attached form a 5- to 6-membered ring optionally containing 1 to 3 heteroatoms selected from O, NH or S; and $R_x$ and $R_y$ independently represent hydrogen, $(C_1-C_6)$ alkyl or $(C_2-C_6)$acyl.

10. The method of claim 1, wherein the inhibitor of the VISTA pathway is selected from:

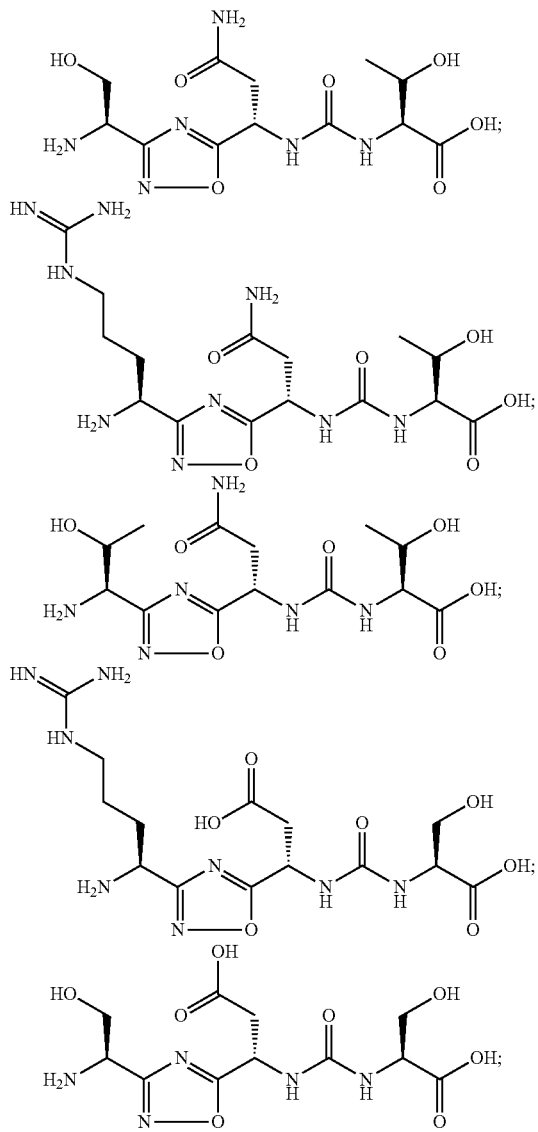

83
-continued
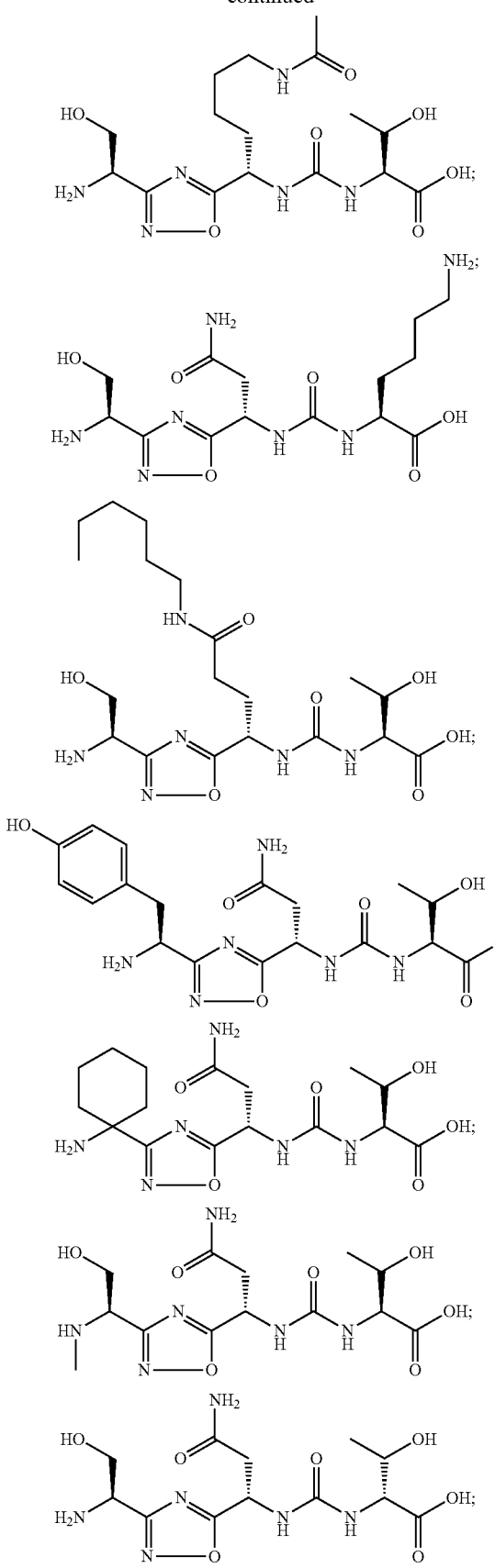
84
-continued
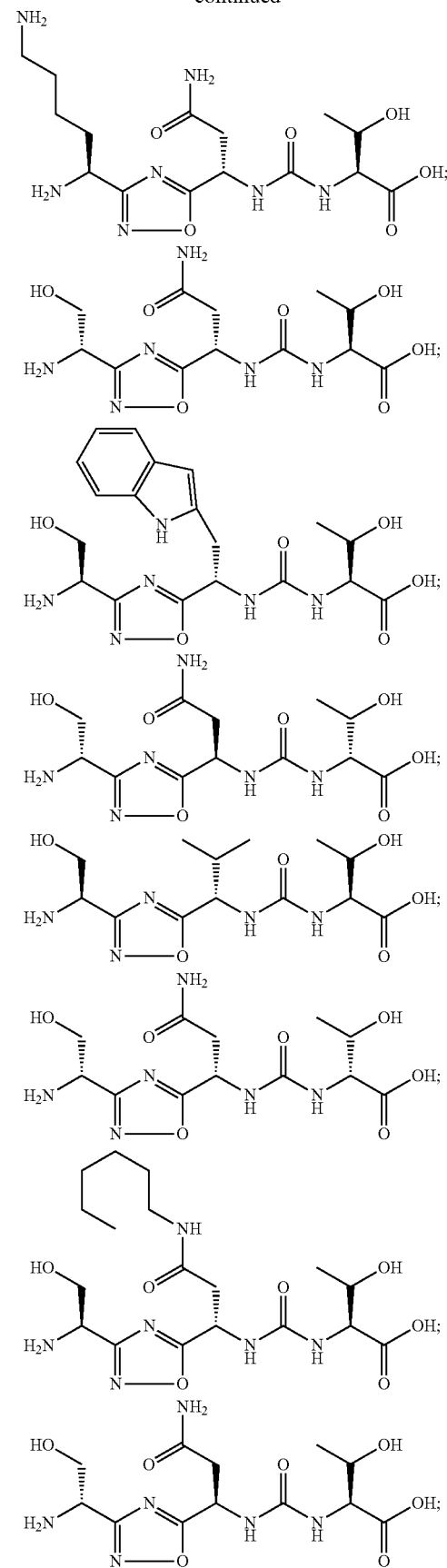

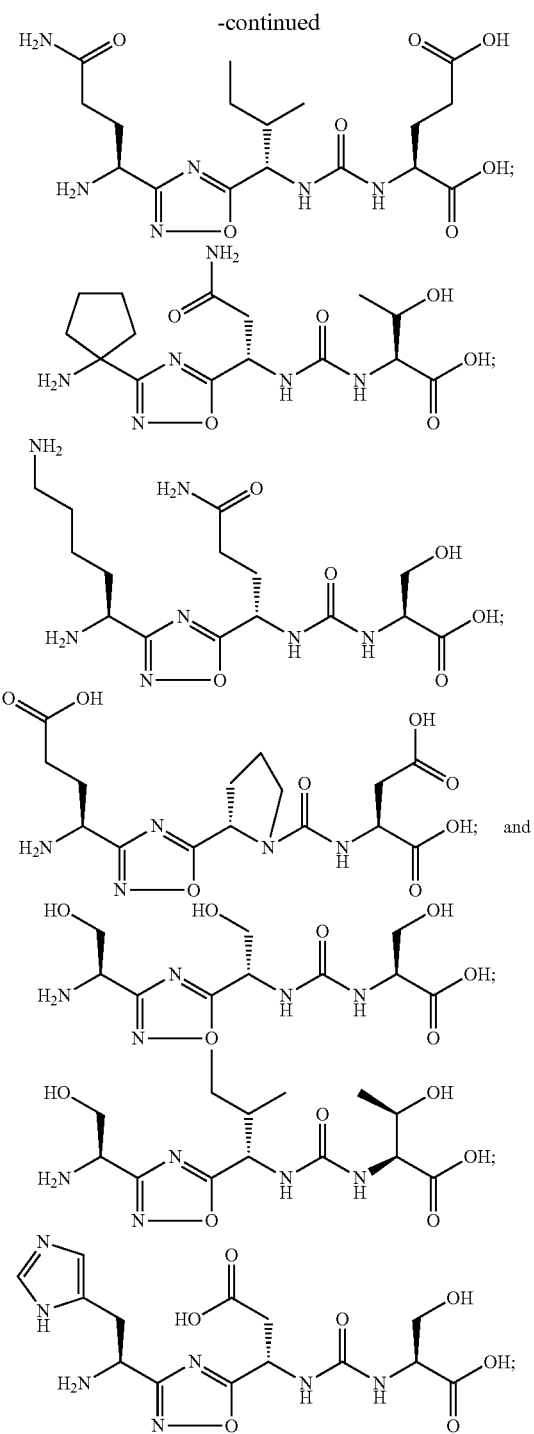

a pharmaceutically acceptable salt thereof.

11. The method of claim 1, wherein Z represents —NH-G'.

12. The method of claim 1, wherein G' represents hydrogen or methyl.

13. The method of claim 1, wherein Z represents —OH.

14. The method of claim 1, wherein $R_{a''}$ represents $(C_1-C_4)$alkyl substituted with —OH, —$NR_xR_y$, —NH—C(=NH)—$NH_2$, —$SR_x$, carboxylic acid, or aryl, wherein the aryl group is optionally further substituted with hydroxyl.

15. The method of claim 1, wherein $R_{a''}$ and G' taken together with the atoms to which they are attached form a 5- to 6-membered ring containing 1 to 3 heteroatoms selected from O, N or S.

16. The method of claim 1, wherein $R_{a''}$ and $R_{a'''}$ taken together with the atoms to which they are attached form a 5- to 6-membered ring, optionally containing 1 to 3 heteroatoms selected from O, N or S.

17. The method of claim 1, wherein $R_{b'}$ represents $(C_1-C_4)$alkyl optionally substituted with —C(O)$NR_xR_y$, —$NR_xR_y$, or carboxylic acid.

18. The method of claim 1, wherein $R_{b'}$ and $R_{c'}$ taken together with the atoms to which they are attached form a 5- to 6-membered ring containing 1 to 3 heteroatoms selected from O, N or S, wherein the 5- to 6-membered ring is optionally further substituted with hydroxyl.

19. The method of claim 1, wherein Y represents a group represented by the following structural formula

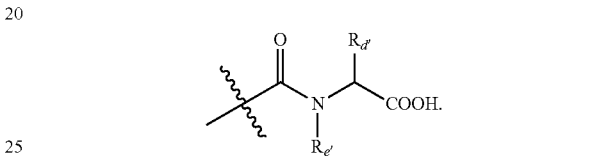

20. The method of claim 1, wherein $R_{d'}$ represents $(C_1-C_4)$alkyl, optionally substituted with —OH, —$OCH_3$, —C(O)OH, or p-OH(phenyl); and $R_{e'}$ represents hydrogen.

21. The method of claim 1, wherein $R_{d'}$ and $R_{e'}$ taken together with the atoms to which they are attached form a 5- to 6-membered ring containing 1 to 3 heteroatoms selected from O, N or S.

22. The method of claim 1, wherein Y represents hydrogen.

23. The method of claim 1, wherein:
Z represents —OH, or —NH-G';
G' represents hydrogen or $(C_1-C_6)$alkyl;
Y represents a group represented by the following structural formula

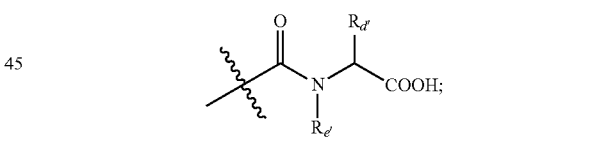

$R_{a''}$ represents $(C_1-C_6)$alkyl substituted with —OH, —$NH_2$, carboxylic acid, guanidino, or aryl;

$R_{a'''}$ represents hydrogen; or $R_{a''}$ and $R_{a'''}$ taken together with the atom to which they are attached form a 5- to 6-membered ring, optionally containing 1 to 3 heteroatoms selected from O, N or S;

$R_{b'}$ represents $(C_1-C_6)$alkyl, optionally substituted with —C(O)$NR_xR_y$, or carboxylic acid;

$R_{c'}$ represents hydrogen; or $R_{b'}$ and $R_{c'}$ taken together with the atoms to which they are attached form a 5- to 6-membered ring containing 1 to 3 heteroatoms selected from O, N or S;

$R_{d'}$ represents $(C_1-C_6)$alkyl, optionally substituted with —$OR_x$;

$R_{e'}$ represents hydrogen; or $R_{d'}$ and $R_{e'}$ taken together with the atoms to which they are attached form a 5- to 6-membered ring containing 1 to 3 heteroatoms selected from O, N or S; and $R_{x'}$ and $R_{y'}$ independently represent hydrogen, $(C_1-C_6)$ alkyl or $(C_2-C_6)$acyl.
24. The method of claim 1, wherein the compound that inhibits the TIM-3 pathway is selected from:
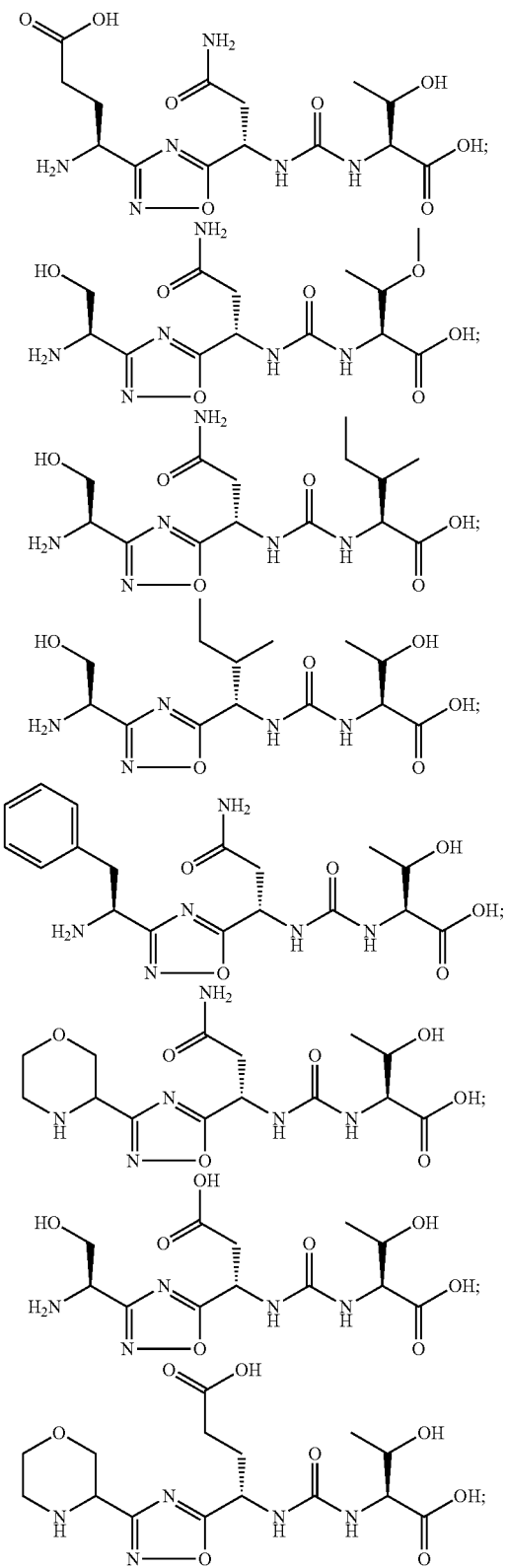
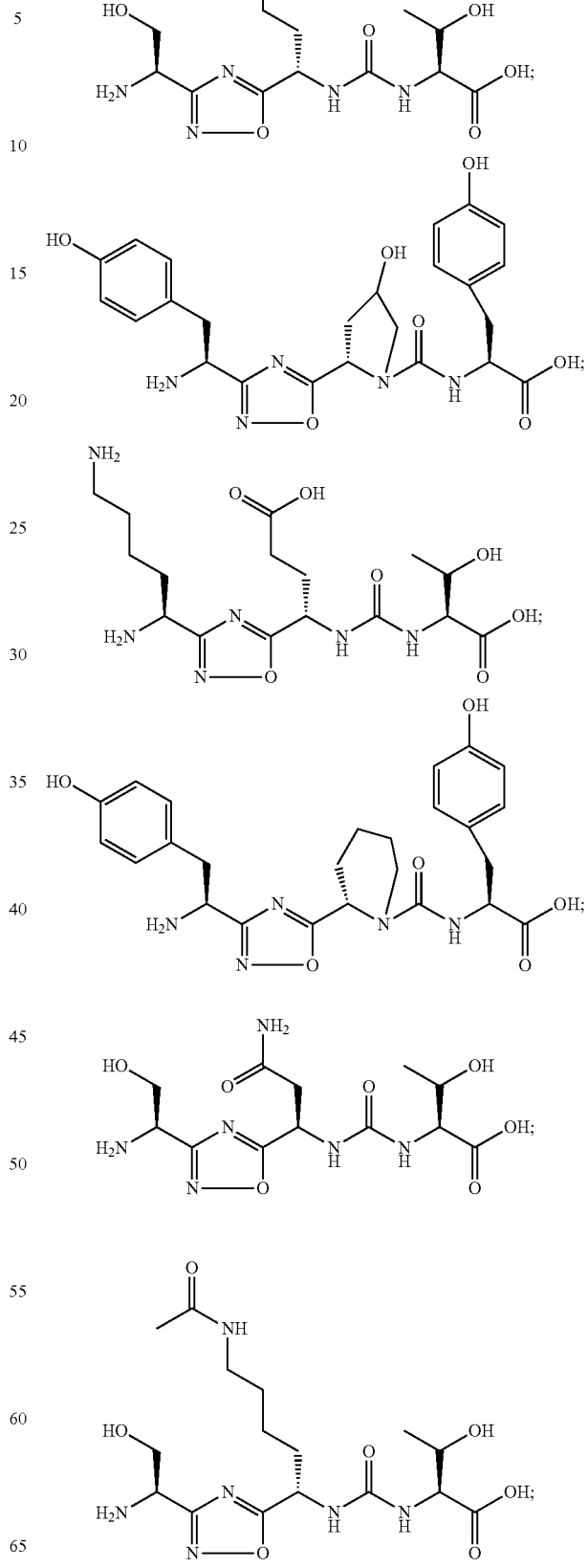

a pharmaceutically acceptable salt thereof.
25. The method of claim 1, wherein the compound that inhibits the VISTA pathway is
or a pharmaceutically acceptable salt thereof.

26. The method of claim 1, wherein the compound that inhibits the TIM-3 pathway is

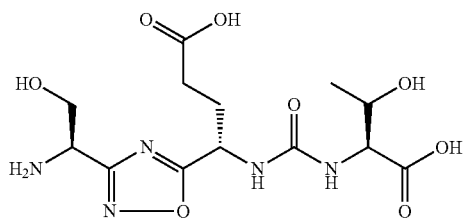 [SMILES: CC(O)[C@H](NC(=O)N[C@@H](CCC(=O)O)c1nc([C@@H](N)CO)no1)C(=O)O]

or a pharmaceutically acceptable salt thereof.

27. The method of claim 1, wherein the subject is suffering from a disease or disorder selected from cancer, immune disorders, immunodeficiency disorders, inflammatory disorders, infectious diseases, and transplant rejection; and the method treats the disease or disorder.

28. The method of claim 27, wherein the disease or disorder is cancer.

29. The method of claim 28, wherein the cancer is selected from small cell lung cancer, multiple myeloma, bladder carcinoma, primary ductal carcinoma, ovarian carcinoma, Hodgkin's lymphoma, gastric carcinoma, acute myeloid leukemia, and pancreatic cancer.

30. The method of claim 28, wherein the cancer is selected from blastoma, breast cancer, epithelial cancer, colon cancer, lung cancer, melanoma, prostate cancer, renal cancer, bone cancer, pancreatic cancer, skin cancer, cancer of the head or neck, uterine cancer, ovarian cancer, colorectal cancer, rectal cancer, cancer of the anal region, cancer of the peritoneum, stomach cancer, testicular cancer, carcinoma of the fallopian tubes, carcinoma of the endometrium, cervical cancer, vaginal cancer, vulval cancer, cancer of the esophagus, cancer of the small intestine, cancer of the endocrine system, cancer of the thyroid gland, cancer of the parathyroid gland, cancer of the adrenal gland, sarcoma, cancer of the urethra, cancer of the penis, chronic or acute leukemia, solid tumors of childhood, Hodgkin's lymphoma, non-Hodgkin's lymphoma, mesothelioma, thymic carcinoma, myeloma, cancer of the bladder, cancer of the ureter, carcinoma of the renal pelvis, liver cancer, pancreatic cancer, post-transplant lymphoproliferative disorder (PTLD), neoplasm of the central nervous system (CNS), tumor angiogenesis, spinal axis tumor, brain stem glioma, pituitary adenoma, epidermoid cancer, salivary gland carcinoma, squamous cell cancer, abnormal vascular proliferation associated with phakomatoses, Meigs' syndrome, Merkel cell carcinoma, and environmentally induced cancers.

31. The method of claim 1, wherein the compound that inhibits the VISTA pathway is

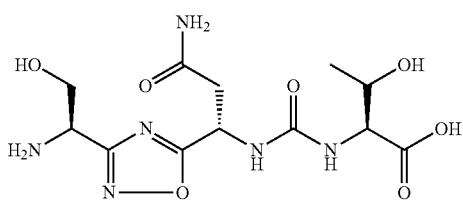 [SMILES: CC(O)[C@H](NC(=O)N[C@@H](CC(N)=O)c1nc([C@@H](N)CO)no1)C(=O)O]

or a pharmaceutically acceptable salt thereof; and the compound that inhibits the TIM-3 pathway is

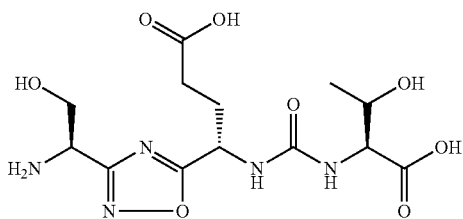 [SMILES: CC(O)[C@H](NC(=O)N[C@@H](CCC(=O)O)c1nc([C@@H](N)CO)no1)C(=O)O]

or a pharmaceutically acceptable salt thereof.

* * * * *

UNITED STATES PATENT AND TRADEMARK OFFICE
CERTIFICATE OF CORRECTION

PATENT NO. : 11,497,735 B2
APPLICATION NO. : 16/761964
DATED : November 15, 2022
INVENTOR(S) : Pottayil Govindan N. Sasikumar et al.

Page 1 of 1

It is certified that error appears in the above-identified patent and that said Letters Patent is hereby corrected as shown below:

In the Claims

In Claim 10, appearing at Column 82, Lines 35-40, please replace:

"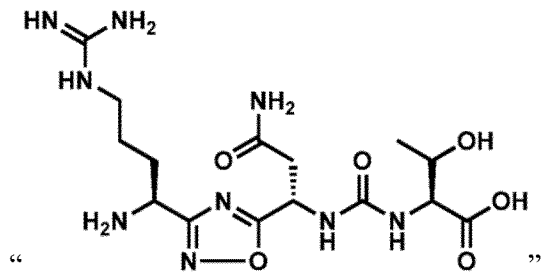"

With:

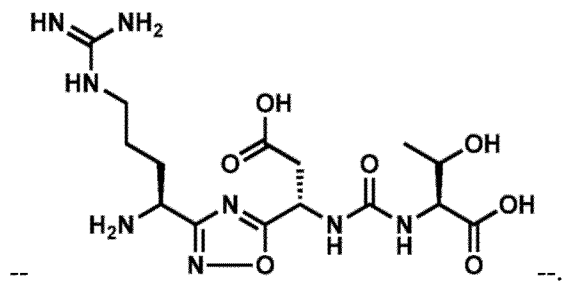
--                                                             --.

Signed and Sealed this
Ninth Day of May, 2023

Katherine Kelly Vidal
*Director of the United States Patent and Trademark Office*